United States Patent
Boveja et al.

(10) Patent No.: US 7,369,897 B2
(45) Date of Patent: ***May 6, 2008

(54) METHOD AND SYSTEM OF REMOTELY CONTROLLING ELECTRICAL PULSES PROVIDED TO NERVE TISSUE(S) BY AN IMPLANTED STIMULATOR SYSTEM FOR NEUROMODULATION THERAPIES

(75) Inventors: Birinder R. Boveja, Milwaukee, WI (US); Angely R. Widhany, Milwaukee, WI (US)

(73) Assignee: Neuro and Cardiac Technologies, LLC, Milwaukee, WI (US)

( * ) Notice: Subject to any disclaimer, the term of this patent is extended or adjusted under 35 U.S.C. 154(b) by 379 days.

This patent is subject to a terminal disclaimer.

(21) Appl. No.: 10/730,513

(22) Filed: Dec. 7, 2003

(65) Prior Publication Data

US 2005/0131493 A1    Jun. 16, 2005

Related U.S. Application Data

(63) Continuation-in-part of application No. 09/837,565, filed on Apr. 19, 2001, now Pat. No. 6,662,052.

(51) Int. Cl.
*A61N 1/08* (2006.01)
(52) U.S. Cl. .................................. 607/60; 607/61
(58) Field of Classification Search ............ 607/2, 607/32–34, 60–61
See application file for complete search history.

(56) References Cited

U.S. PATENT DOCUMENTS

| | | | |
|---|---|---|---|
| 5,630,836 A * | 5/1997 | Prem et al. ............... 607/61 |
| 5,759,199 A | 6/1998 | Snell et al. ................... 607/60 |
| 5,978,713 A | 11/1999 | Prutchi ........................ 607/60 |
| 5,997,476 A | 12/1999 | Brown ....................... 600/300 |
| 6,270,457 B1 | 8/2001 | Bardy ......................... 600/300 |
| 6,418,346 B1 | 7/2002 | Nelson et al. ................ 607/59 |
| 6,442,432 B2 * | 8/2002 | Lee ............................... 607/59 |
| 6,443,891 B1 | 9/2002 | Grevious .................... 600/302 |
| 6,539,947 B2 * | 4/2003 | Boies et al. ................ 128/899 |
| 7,082,333 B1 * | 7/2006 | Bauhahn et al. .............. 607/60 |
| 7,181,505 B2 * | 2/2007 | Haller et al. ................ 709/219 |
| 7,191,012 B2 * | 3/2007 | Boveja et al. ................ 607/60 |

* cited by examiner

*Primary Examiner*—Mark Bockelman

(57) ABSTRACT

A method and system of remotely controlling an implanted stimulator for providing electrical pulses to nerve tissue, comprises an implantable stimulator, an interface unit, and a mobile device such as a modified PDA/cell phone (or pocket PC/cell phone). The implanted stimulator may be for vagus nerve(s), sacral plexus, spinal cord or the like. The implanted stimulator comprises an implanted pulse generator (IPG) and a stimulus-receiver module. Interrogation and programming of the implanted stimulator may be performed remotely via a modified PDA/cell phone over a wide area network. The interface unit at the patient end comprises a telemetry module, and may be part of an external stimulator or a programmer. In one aspect of the invention, in addition to remote interrogation and programming, a patient's clinical data/information, report, and invoicing information can be retrieved from a server, reviewed, and updated on the modified PDA/cell phone over a wide area network.

31 Claims, 45 Drawing Sheets

FIG. 35

METHOD AND SYSTEM OF REMOTELY CONTROLLING ELECTRICAL PULSES PROVIDED TO NERVE TISSUE(S) BY AN IMPLANTED STIMULATOR SYSTEM FOR NEUROMODULATION THERAPIES

This application is a continuation-in-part of U.S. patent application Ser. No. 09/837,565 entitled "METHOD AND SYSTEM FOR NEUROMODULATION THERAPY USING EXTERNAL STIMULATOR WITH WIRELESS COMMUNICATION CAPABILITIES", filed Apr. 19, 2001 now U.S. Pat. No. 6,662,052. Priority is claimed from this application, and the prior application being incorporated herein by reference.

FIELD OF THE INVENTION

The present invention relates to remotely controlling an implanted stimulator, more specifically for remotely interrogating and programming an implanted stimulator through an interface device using a modified PDA/c II phone. The implanted stimulator being used for neuromodulation therapy.

BACKGROUND OF THE INVENTION

Neuromodulation therapy using pulsed electrical stimulation is usually provided by an implanted stimulator or an external stimulator coupled to an implanted stimulus-receiver. The parent application, Ser. No. 09/837,565 is generally directed to wireless communications capability of an external stimulator designed to operate with an implanted stimulus-receiver. This disclosure is directed to wireless communication capability of an implanted stimulator via an interface device, as is depicted in FIGS. 1A-1E The implanted stimulator of the current invention is used to provide electrical pulses or neuromodulation therapy for urological, neurological, neuropsychiatric disorders, obesity and eating disorders, and spinal cord related pain disorders.

Background of Neuromodulation Therapy

Urinary Incontinence

In considering first, the background of urinary urge incontinence. FIG. 2A shows a sagittal section of the human female pelvis showing the bladder 10 and urethra 13, in relation to other anatomic structures. Urinary continence requires a relaxed bladder during the collecting phase and permanent closure of the urethra 13, whereas at micturition (urination), an intravesical pressure above the opening pressure of the simultaneously relaxing urethra has to be generated. These functions of the bladder 10 and urethra 13 are centrally coordinated and non-separable. At bladder filling, the sensation of urge is mediated by slowly adapting mechanoreceptors in the bladder wall and the same receptors provide the triggering signal for micturition and the main driving force for a sustained micturition contraction. The mechanoreceptors are, technically speaking, tension receptors. It has been found that they respond equally well to tension increases induced passively by bladder filling and those induced actively by a detrusor contraction. These receptors have high dynamic sensitivity and are easily activated by external pressure transients, as may occur during coughing or tapping of the abdominal wall. Their faithful response to active changes in bladder pressure is well illustrated.

When sufficiently activated, the mechanoreceptors trigger a coordinated micturition reflex via a center in the upper pons 88, as depicted schematically in FIG. 2B. The reflex detrusor 89 (muscle in the wall of the urinary bladder) contraction generates an increased bladder pressure and an even stronger activation of the mechanoreceptors. Their activity in turn reinforces the pelvic motor output to the bladder 10, which leads to a further increase in pressure and more receptor activation and so on. In this way, the detrusor 89 contraction is to a large extent self generating once initiated. Such a control mechanism usually is referred to as a positive feedback, and it may explain the typical all-or-nothing behavior of the parasympathetic motor output to the bladder 10. Once urine enters the urethra, the contraction is further enhanced by reflex excitation from urethral receptors. Quantitatively, the bladder receptors are most important.

A great advantage of the positive feedback system is that it ascertains a complete emptying of the bladder 10 during micturition. As long as there is any fluid left in the lumen, the intravesical pressure will be maintained above the threshold for the mechanoreceptors and thus provide a continuous driving force for the detrusor 89. A drawback with this system is that it can easily become unstable. Any stimulus that elicits a small burst of impulses in mechanoreceptor afferents may trigger a fullblown micturition reflex. To prevent this from happening during the filling phase, the neuronal system controlling the bladder is equipped with several safety devices both at the spinal and supraspinal levels.

The best-known spinal mechanism is the reflex control of the striated urethral sphincter 87, which increases its activity in response to bladder mechanoreceptor activation during filling. An analogous mechanism is Edvardsen's reflex, which involves machanoreceptor activation of inhibitory sympathetic neurons to the bladder. The sympathetic efferents have a dual inhibitory effect, acting both at the postganglionic neurons in the vesical ganglia and directly on the detrusor muscle of the bladder 89. The sphincter and sympathetic reflexes are automatically turned off at the spinal cord level during a normal micturition. At the supraspinal level, there are inhibitory connections from the cerebral cortex and hypothalamus to the pontine micturition center. The pathways are involved in the voluntary control of continance. Other inhibitory systems seem to originate from the pontine and medullary parts of the brainstem with at least partly descending connections.

Bladder over-activity and urinary urge incontinence may result from an imbalance between the excitatory positive feedback system of the bladder 10 and inhibitory control systems causing a hyperexcitable voiding reflex. Such an imbalance may occur aft r macroscopic lesions at many sites in the nervous system or after minor functional disturbances of the excitatory or inhibitory circuits. Urge incontinence due to detrusor instability seldom disappears spontaneously. The symptomatic pattern also usually is consistent over long periods.

The sensory disturbance of these subjects is not in the periphery, at the level of bladder mechanoreceptors, as the micturition reflex occurs at normal or even small bladder volumes. More likely, the supraspontine sensory projection to the cortex is affected. Such a site is consistent with the coordinated micturition and the lack of voluntary control. The uninhibited overactive bladder is present in neurogenic dysfunction. Electrostimulation is a logical alternative in mixed stress and urge incontinence, since the method improves urethral closure as well as bladder control Neuromodulation is a technique that uses electrical stimulation of the sacral nerves 85, (a general diagram of spinal cord and sacral nerves 85 is shown in FIG. 3). The aim of this treatment modality is to achieve detrusor 89 inhibition by chronic electrical stimulation of afferent somatic sacral nerve fibers 85 via implanted electrodes connected to a subcutaneously placed pulse generation means.

In neuromodulation, the entire innervation system should be intact. As shown schematically in FIG. 4, the procedure consists of placing electrodes 61, 62 in one of the sacral foramen as close to the pelvic plexus and pudendal nerve as possible and connecting the lead 59 with a means for electrical stimulation 75. An anchoring sleeve 15 may be used for securing the lead.

The hypothesis behind neuromodulation of the sacral roots (sensory and motor) is to correct, by the use of regulating electrical impulses, the dys-synergic activities of the cholinergic, adrenergic, and motor reflex pathways that initiate vesical storage and micturition. Although some theories have been developed that explain the effects of neuromodulation, most of the results are based on empiric findings in human studies. Some animal experiments and electrophysiologic studies in humans show there is a spinal inhibitory action through the afferent branches of the pelvic and pudendal nerves. It is not clear whether neuromodulation primarily influences the micturiction center located near the thalamus 25. Some maintain that there is a direct correction of the dys-synergis of the pelvic floor (pudendal nerve) by influencing the abnormal contractility of the pelvic floor.

Neuromodulation also acts on neural reflexes but does so internally by stimulation of the sacral nerves 85. Sacral nerve 85 stimulation is based on research dedicated to the understanding of the voiding reflex as well as the role and influence of the sacral nerves 85 on voiding behavior. This research led to the development of a technique to modulate dysfunctional voiding behavior through sacral nerve stimulation. It is thought that sacral nerve stimulation induces reflex mediated inhibitory effects on the detrusor 89 through afferent and/or efferent stimulation of the sacral nerves 85.

In summary, the rationale for neuromodulation in the treatment of such patients is the observation that stimulation of the sacral nerves via electrical stimulation can inhibit inappropriate neural reflex behavior.

Neurological and Neuropsychiatric Disorders

Moving now to the background of neurological disorders. Adjunct therapy for neurological disorders such as partial complex epilepsy, generalized epilepsy, depression, Alzheimer's disease, and several other disorders related to neuromodulation of the vagus nerve. Biological research has shown beneficial medical effects of vagus nerve stimulation (VNS) for patients with the above disorders.

Vagus nerve stimulation, and the profound effects of electrical stimulation of the vagus nerve on central nervous system (CNS) activity, extends back to the 1930's. Medical studies in clinical neurobiology have advanced our understanding of anatomic and physiologic basis of the beneficial neurologic effects of chronic vagus nerve stimulation.

Some of the somatic interventions for the treatment of depression and the like, include electroconvulsive therapy (ECT), transcranical magnetic stimulation, vagus nerve stimulation, and deep brain stimulation. The vagus nerve 54 is the 10th cranial nerve, and is a direct extension of the brain. FIG. 5, shows a diagram of the brain and spinal cord, with its relationship to the vagus nerve 54 and the nucleus tractus solitarius 14. FIG. 6 shows a diagram of base of the brain, showing the relationship of the vagus nerve with the other eleven cranial nerves.

Vagus nerve stimulation is a means of directly affecting central function and is less invasive than deep brain stimulation (DBS). As shown in FIG. 7, cranial nerves have both afferent pathway 19 (inward conducting nerve fibers which convey impulses toward the brain) and efferent pathway 21 (outward conducting nerve fibers which convey impulses to an effector). The vagus nerve 54 is composed of 80% afferent sensory fibers carrying information to the brain from the head, neck, thorax, and abdomen. The sensory afferent cell bodies of the vagus reside in the nodose ganglion and relays information to the nucleus tractus solitarius (NTS).

As shown schematically in FIG. 8, the nucleus of the solitary tract 14 relays this incoming sensory information to the rest of the brain through three main pathways; 1) an autonomic feedback loop, 2) direct projection to the reticular formation in the medulla, and 3) ascending projections to the forebrain largely through the parabrachial nucleus 20 (PBN) and the locus ceruleius 22 (LC). The PBN sits adjacent to the LC (FIG. 5). The PBN/LC sends direct connections to every level of the forebrain, including the hypothalamus 26, and several thalamic regions that control the insula and orbito-frontal 28 and prefrontal cortices. Perhaps important for mood regulation, the PBN/LC has direct connections to the amygdala 27 and the bed nucleus of the stria terminalis—structures that are implicated in emotion recognition and mood regulation.

In sum, incoming sensory (afferent) connections of the vagus nerve 54 provide direct projections to many of the brain regions implicated in neurologic and neuropsychiatric disorders. These connections reveal how vagus nerve 54 stimulation is a portal to the brainstem and connected regions. These circuits likely account for the beneficial neurologic and neuropsychiatric effects of the vagus nerve stimulation.

Increased activity of the vagus nerve 54 is also associated with the release of more serotonin in the brain. Much of the pharmacologic therapy for treatment of migraines is aimed at increasing the levels of serotonin in the brain. Therefore, non-pharmacologic therapy of electrically stimulating the vagus nerve 54 would have benefits for adjunct treatment of migraines also.

The vagus nerve 54 provides an easily accessible, peripheral route to modulate central nervous system (CNS) function. Other cranial nerves can be used for the same purpose, but the vagus nerve 54 is preferred because of its easy accessibility. In the human body there are two vagus nerves (VN), the right VN and the left VN. Each vagus nerve is encased in the carotid sheath along with the carotid artery and jugular vein. The innervation of the right and left vagus nerves is different. The innervation of the right vagus nerve is such that stimulating it results in profound bradycardia (slowing of the heart rate). The left vagus nerve has some innervation to the heart, but mostly innervates the visceral organs such as the gastrointestinal tract. It is known that stimulation of the left vagus nerve does not cause any significant deleterious side effects.

Most nerves in the human body are composed of thousands of fibers, of different sizes designated by groups A, B and C, which carry signals to and from the brain. The vagus nerve 54, for example, may have approximately 100,000 fibers of the three different types, each carrying signals. Each axon or fiber (shown in FIG. 9A) of that nerve conducts only in one direction, in normal circumstances. The A and B fibers are myelinated (i.e., have a myelin sheath, constituting a substance largely composed of fat, as shown in FIG. 9B), whereas the C fibers are unmyelinated.

A commonly used nomenclature for peripheral nerve fibers, using Roman and Greek letters, is given in the table below:

| Group | External Diameter (μm) | Conduction Velocity (m/sec) |
| --- | --- | --- |
| Myelinated Fibers | | |
| Aα or IA | 12-20 | 70-120 |
| Aβ: IB | 10-15 | 60-80 |
| II | 5-15 | 30-80 |
| Aγ | 3-8 | 15-40 |
| Aδ or III | 3-8 | 10-30 |
| B | 1-3 | 5-15 |
| Unmyelinted fibers | | |
| C or IV | 0.2-1.5 | 0.5-2.5 |

The diameters of group A and group B fibers include the thickness of the myelin sheaths. Group A is further subdivided into alpha, beta, gamma, and delta fibers in decreasing order of size. There is some overlapping of the diameters of the A, B, and C groups because physiological properties, especially the form of the action potential, are taken into consideration when defining the groups. The smallest fibers (group C) are unmyelinated and have the slowest conduction rate, whereas the myelinated fibers of group B and group A exhibit rates of conduction that progressively increase with diameter. Group B fibers are not present in the nerves of the limbs; they occur in white rami and some cranial nerves.

Compared to unmyelinated fibers, myelinated fibers are typically larger, conduct faster, have very low stimulation thresholds, and exhibit a particular strength-duration curve or respond to a specific pulse width versus amplitude for stimulation. The A and B fibers can be stimulated with relatively narrow pulse widths, from 50 to 200 microseconds (μs), for example. The A fiber conducts slightly faster than the B fiber and has a slightly lower threshold. The C fibers are very small, conduct electrical signals very slowly, and have high stimulation thresholds typically requiring a wider pulse width (300-1,000 μs) and a higher amplitude for activation. Selective stimulation of only A and B fibers is readily accomplished. The requirement of a larger and wider pulse to stimulate the C fibers, however, makes selective stimulation of only C fibers, to the exclusion of the A and B fibers, virtually unachievable inasmuch as the large signal will tend to activate the A and B fibers to some extent as well.

The vagus nerve is composed of somatic and visceral afferents and efferents. Usually, nerve stimulation activates signals in both directions (bi-directionally). It is possible, however, through the use of special electrodes and waveforms, to selectively stimulate a nerve in one direction only (unidirectionally). The vast majority of vagus nerve fibers are C fibers, and a majority are visceral afferents having cell bodies lying in masses or ganglia in the skull. The central projections terminate largely in the nucleus of the solitary tract 14 which sends fibers to various regions of the brain (e.g., the hypothalamus 26, thalamus 25, and amygdala 27).

In summary the basic premise of vagus nerve 54 stimulation for relief of neurological disorders is that vagus visceral afferents have a diffuse central nervous system (CNS) projection, and activation of these pathways has a widespread effect on neuronal excitability.

Obesity

In 1988 it was reported in the *American Journal of Physiology*, that the afferent vagal fibers from the stomach wall increased their firing rate when the stomach was filled. One way to look at this regulatory process is to imagine that the drive to eat, which may vary rather slowly with the rise and fall of hormone Leptin, is inhibited by satiety signals that occur when we eat and begin the digestive process (i.e., the prandial period). As shown schematically in the top part of FIG. 9, these satiety signals both terminate the meal and inhibit feeding for some time afterward. During this post-absorptive (fasting) period, the satiety signals slowly dissipate until the drive to eat again takes over The regulation of feeding behavior is a complex process, and involves the concentrated action of several satiety signals such as gastric distention, the release of the gastrointestinal peptide cholecystokinin (CCK), and the release of the pancreatic hormone insulin. The stomach wall is richly innervated by mechanosensory axons, and most of these ascend to the brain via the vagus nerve 54. The vagus sensory axons activate neurons in the Nucleus of the Solitary Tract in the medulla of the brain (described later in this application). These signals inhibit feeding behavior. In a related mechanism, the peptide CCK is released in response to stimulation of the intestines by certain types of food, especially fatty ones. CCK reduces frequency of eating and size of meals. As shown schematically in FIG. 9, both gastric distension and CCK act synergistically to inhibit feeding behavior.

Accordingly, appropriate extra-physiologic electrical stimulation of a vagus nerve 54 or both vagus nerves, from just above the stomach level, should produce appetite suppression by causing the patient to experience satiety. This is shown schematically in FIG. 10 in the form of subdiaphramatic bilateral stimulation. In one aspect, upon experiencing the compulsive craving, the obese patient can voluntarily activate the stimulus generator by activating a predetermined program. In another aspect, the patient receives chronic stimulation according to a predetermined program whereby stimulation is on for a period of time, followed by off-time in repeating cycles Cardiovascular Indications and Nervous Control of the Heart The principle control of heart rate is via the autonomic nervous system. Normally, the average heart rate is approximately 70 beats per minute at rest. During sleep the heart rate diminishes by 10 to 20 beats per minute, but during emotional excitement or muscular activity it may accelerate to rates considerably above 100. In well-trained athletes at rest, the rate is usually only about 50 beats per minute.

The sinoatrial (SA) node of the heart is usually under the tonic influence of both divisions of the autonomic nervous system. The sympathetic system enhances automaticity, by increasing the phase 4 depolarization of the pacemaker cells in the sinus node. The parasympathetic system inhibits the automaticity (such as with right vagus nerve stimulation). Changes in heart rate (HR) usually involve a reciprocal action of the two divisions of the autonomic nervous system. Thus an increased heart rate is produced by a diminution of parasympathetic activity and concomitant increase in sympathetic activity, and deceleration is usually achieved by the opposite mechanisms. Under certain conditions the heart rate may change by selective action of just one division of the autonomic nervous system, rather than by reciprocal changes in both divisions.

Ordinarily, during rest parasympathetic influences preponderate over sympathetic effects at the SA node. Abolition of parasympathetic influences by administration of atropine usually increases heart rate substantially, whereas abolition of sympathetic effects by administration of propranolol usually decreases heart rate only slightly. When both divisions of the autonomic nervous system are blocked, the heart rate averages about 100 beats per minute. The rate that prevails after complete autonomic blockade is the intrinsic heart rate.

The cardiac parasympathetic fibers originate in the medulla oblongata (of the brain), in cells that lie in the dorsal motor nucleus of the vagus or in the nucleus ambiguus. Efferent vagal fibers pass inferiorly through the neck as the cervical vagus nerves, which lie close to the common carotid arteries. They then pass through the mediastinum to synapse with postganglionic cells on the epicardial surface or within the walls of the heart itself (shown schematically in FIG. 11). Most of the cardiac ganglion cells are located near the SA node and atrio-ventricular (AV) conduction tissue. The right and left vagi are distributed differentially to the various cardiac structures. The right vagus nerve affects the SA node predominantly. Stimulation slows SA nodal firing or may even stop it for several seconds. The left vagus nerve mainly inhibits AV conduction tissue, to produce various degrees of AV block. However, the distributions of the efferent vagal fibers overlap, such that left vagal stimulation also depresses the SA node and right vagal stimulation impedes AV conduction.

Neuromodulation of the vagal nerve fibers exert their influence on refractory hypertension via Afferent stimulation. And, neuromodulation of the vagal nerve fibers exert their influence on atrial fibrillation and in Inappropriate Sinus Tachycardia Syndrome via Efferent stimulation of the left and right vagus nerve respectively.

Spinal Cord Stimulation for Pain

Spinal cord stimulation (SCS) using implantable stimulator provides therapy for reducing pain in certain populations of patients. The implantable stimulator generates electrical pulses that are delivered to the dorsal column fibers with the spinal cord through the electrodes which are implanted along the dura of the spinal cord.

Clinically pain is classified as somatic or visceral. Somatic pain arising from the skin, muscles, or joints, can be either superficial or deep. Superficial somatic pain is a sharp, pricking pain that often causes us to cry out. Localizable to the skin deidermis or mucosae, it tends to be brief. This type of pain is tranmitted alon finely myelinated A delta (δ) fibers at the rate if 12 to 80 m/s (up to 250 ft/s). Deep somatic pain is more likely to be burning, itching, or aching pain; it results for stimulation of pain receptors in the deep skin layers, muscles, or joints. Deep somatic pain is both more diffuse and longer lasting than superfical somatic pain, and it slways indicates tissue destruction. Impulses from the deep pain receptors are transmitted slowly (0.4 to over 1 m/s, or up to 3.5 ft/s) along the small, unmyelinated C fibers.

Viceral pain results form noxious stimulation of receptors in the organs of the thorax and abdominal cavity. Like deep somatic pain, it is usually a dull ache, a buring feeling, or gnawing pain. Important stimuli of visceral pain are extreme stretching of tissue, ischemia, irritating chemicals, and muscle spasms. Because viceral pian inputs follow the same pathways as somatic pain (convergence), projection by the brain may cause visceral pain to be perceived as somatic in origin. Both the superfical somatic pain fibers and deep somatic/visceral pain fibers synapse with interneurons in the dorsal horns of the spinal cord.

One of the most significant advances in the understanding and management of pain was the publication of Malzack and Wall's gate control theory of pain in the 1960's. It suggested that: 1) A pain "gate" exists in the dorsal horn (substantia gelatinosa) where impulses from small unmyelinated pain fibers and large touch (A beta) fibers enter the cord. 2) If impulses along the pain fibers outnumber those transmitted along the touch fibers, the gate opens and pain impulses are transmitted. If the reverse is true, the gate is closed by enkephalin-releasing interneurons in the spinal cord that inhibit transmission of both touch and pain impulses, thus reducing pain perception.

It fostered a generation of pain research, and some of its clinical predictions are useful. For example, it's been found that 1) threshold stimulation of the large touch fibers as by massage) results in a burst of firing in the sustantia gelatinosa cells, followed by a brief period of inhibited pain transmission (it does close the pain "gate"), and 2) it has been amply proven that direct electrical stimulation of dorsal column fibers provides extended pain relief.

Prior Art

Prior art wireless communication for medical stimulation devices includes, U.S. Pat. No. 5,759,199 (Snell et al) which is directed to ambulatory monitoring and programming of an implantable medical device. The system disclosed enables wireless communication between the programmer/analyzer and the implantable medical device.

U.S. Pat. No. 5,978,713 (Prutchi) is primarily directed to telemetry of information from an implant that is generated from atrial and ventricular endocardial leads to an external programmer.

U.S. Pat. No. 5,997,476 (Brown) is directed to communicating information to an individual and for remotely monitoring the individual. The system of the '476 patent includes a server and a remote interface for entering in the server a set of queries to be answered by the individual. The disclosed system includes a remotely programmable apparatus connected to the server via a communication network.

U.S. Pat. No. 6,418,346 B1 (Nelson et al.) is generally directed to transferring data into and out of medical devices wherein a personal data manager (PDM) is used in a web-based network. In the system of the Nelson '346 B1 patent, the PDM co-operates with a programmer to enhance remote monitoring of implanted medical devices on a chronic basis.

U.S. Pat. No. 6,270,457 (Bardy) is generally directed to system and method for automated collection and analysis of regularly retrieved patient information for remote patient care. In the system of this patent, a set of collected measures retrieved on a substantially regular bases is periodically received from a medical device having a sensor for monitoring at least one physiological measure of an individual patient.

U.S. Pat. No. 6,443,891 B1 (Grevious) is generally directed to a telemetry system that automatically selects a symmetric modulation protocol configuration for telemetry communication between medical devices and programmers used in providing patient treatment.

SUMMARY OF THE INVENTION

In the method and system of this invention, an implantable system provides electrical pulses for neurostimulation/neuromodulation to the vagus nerve to provide therapy for neurological and neuropsychiatric disorders, neurostimulation to the sacral plexus to provide therapy for urinary incontinence, neurostimulance of the vagus nerve at around the diaphramatic level to provide therapy for obesity, neurostimulation of a right vagus nerve to provide therapy for cardiovascular disorders, and neurostimulation of the spinal cord to provide therapy for chronic pain. The implantable neurostimulation system comprising means for two-way communication with a remote device via an external interface unit. Said two-way communication utilizing a wireless wide area network.

In another aspect of the invention a physician can interrogate an imlanted neurostimulation system from a remote site utilizing a wireless wide area network.

In another aspect of the invention a physician can program an implanted neurostimulation system from a remote site utilizing a wireless wide area network.

In another aspect of the invention a physician can update the billing using PDA and send a copy to the office, over a wide area network.

In another aspect of the invention a physician can update a patient's relevant medical history on a PDA over a wide area network.

BRIEF DESCRIPTION OF THE DRAWINGS

For the purpose of illustrating the invention, there are shown in accompanying drawing, forms which are presently preferred, it being understood that the invention is not intended to be limited to the precise arrangement and instrumentalities shown.

FIGS. 34 and 35 are sample screens on the modified PDA/cell phone

DETAILED DESCRIPTION OF THE INVENTION

The following description is of the current embodiment for carrying out the invention. This description is not to be taken in a limiting sense, but is made merely for the purpose of describing the general principles of the invention. The scope of the invention should be determined with reference to the claims.

Figure 13:
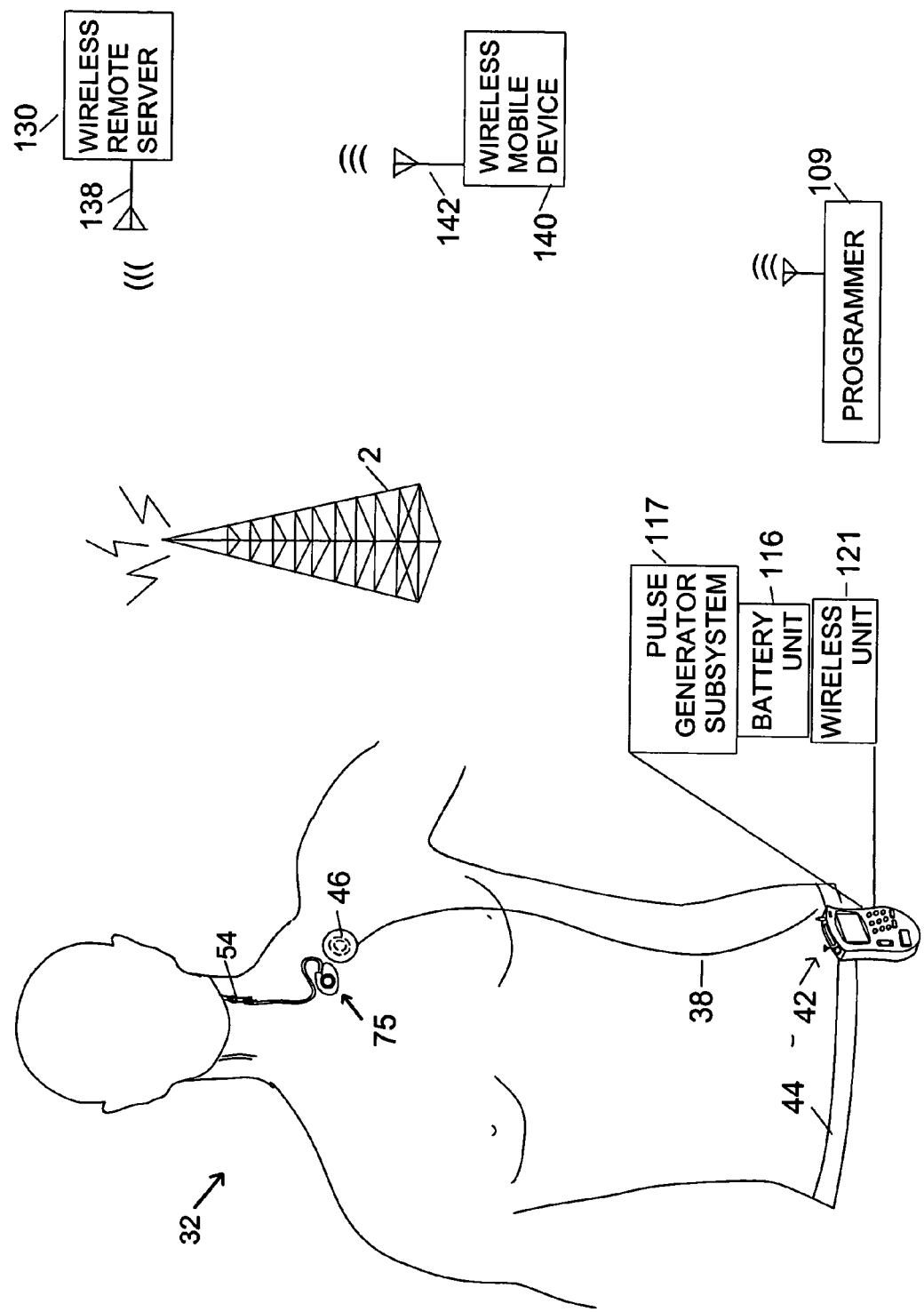
FIG. 13 is a simplified schematic and block diagram showing the implanted stimulator, interface unit, and remote mobile device for communication.

The concept of this invention is depicted in conjunction with FIG. 13. An implantable neurostimulator 75 is implanted in a patient 32 at the appropriate site. The implantable neurostimulator 75 comprises two assemblies, an implanted pulse generator (IPG) module 70 and a stimulus-receiver module 68, as described later. The stimulus-receiver module is inductively coupled to an external stimulator. The external stimulator also comprises two modules, an external stimulator module 117 and a wireless unit 121 module. The combination of these two assemblies is referred to as interface unit/stimulator or IU/stim 42 in this disclosure. The hardware and software of IU/stim 42 is configured to communicate and exchange data over the Internet. A physician situated remotely is able to interrogate and program the IU/stim 42, from any geographical location where cellular service is available, thereby remotely controlling a patient's implanted neurostimulator 75. Further, since the IU/stim 42, the physician's mobile device 140, a remote server, and a programmer 109 are all networked, information can be exchanged between these devices.

Figure 1A:
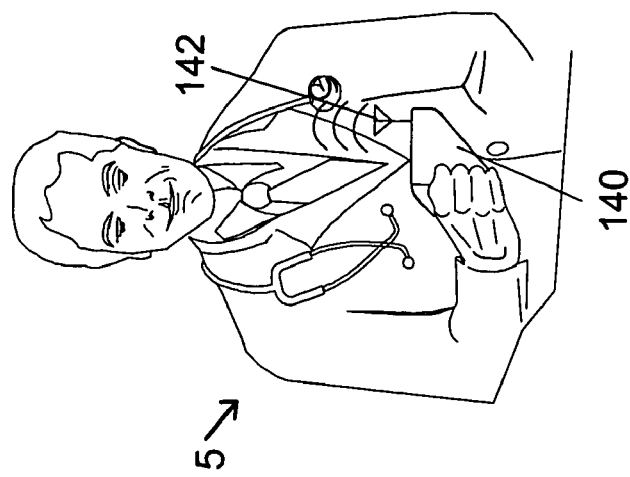
FIGS. 1A-1E diagrammatically show a physician communicating with a remote patient implanted with a neurostimulator.
Figure 1A:
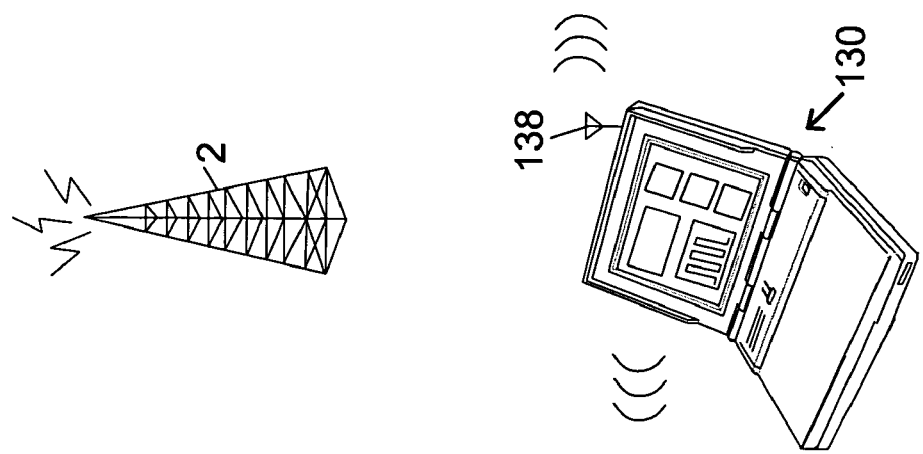
Figure 1A:
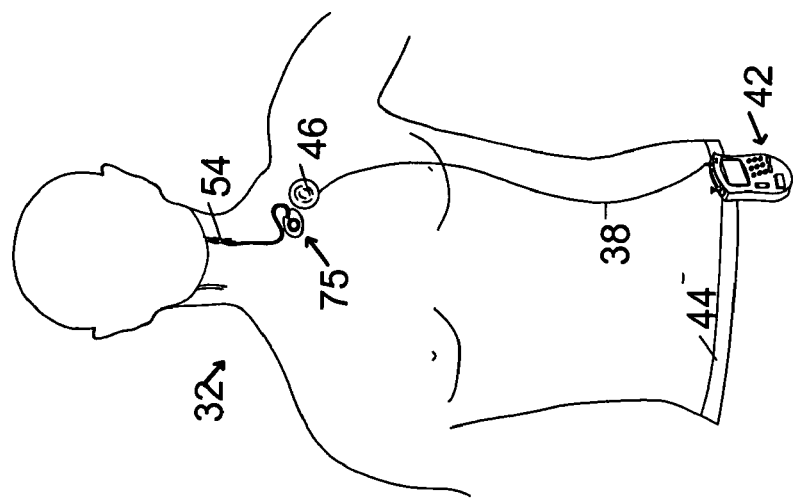
Figure 1B:
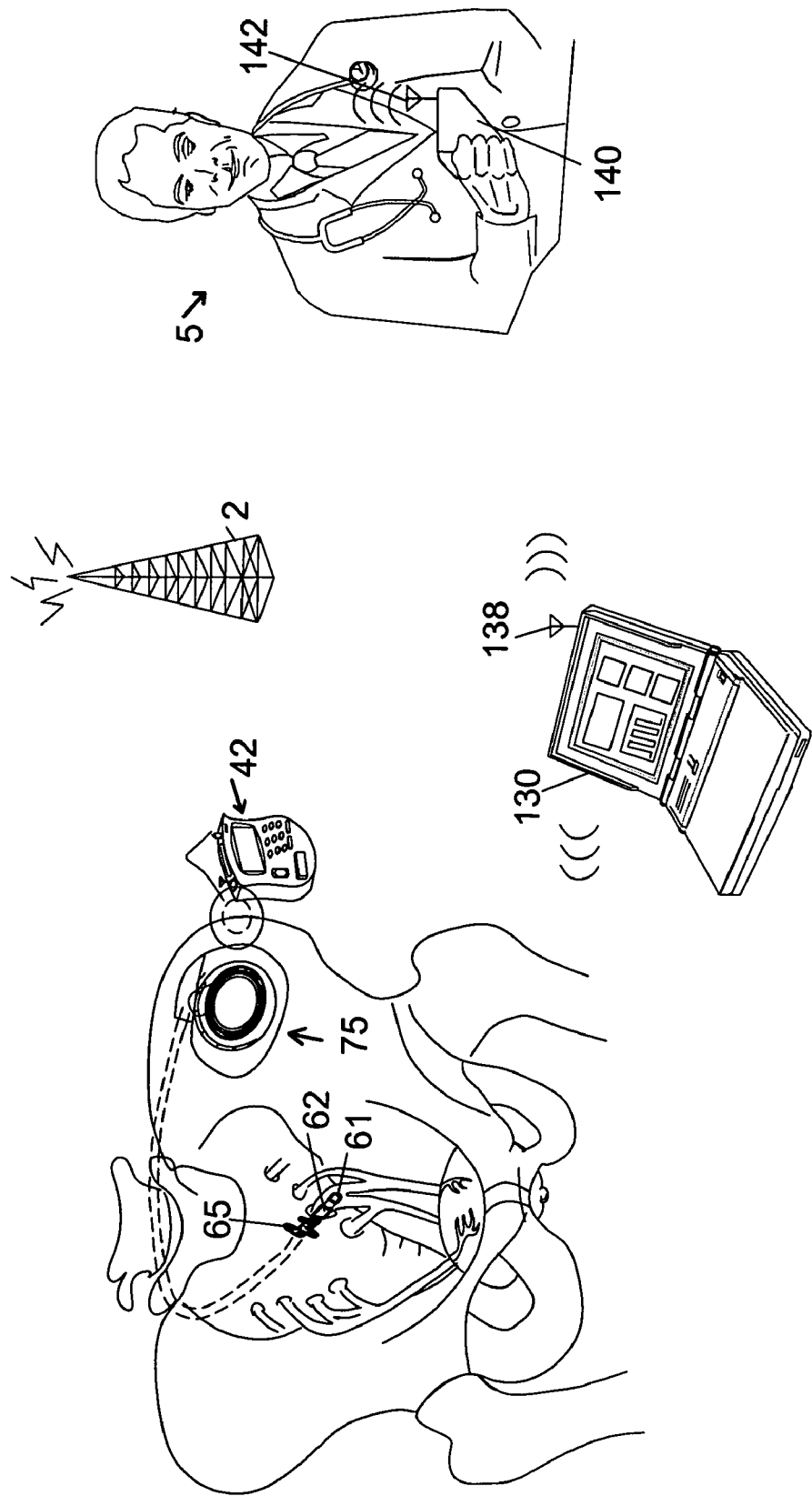
Figure 1C:
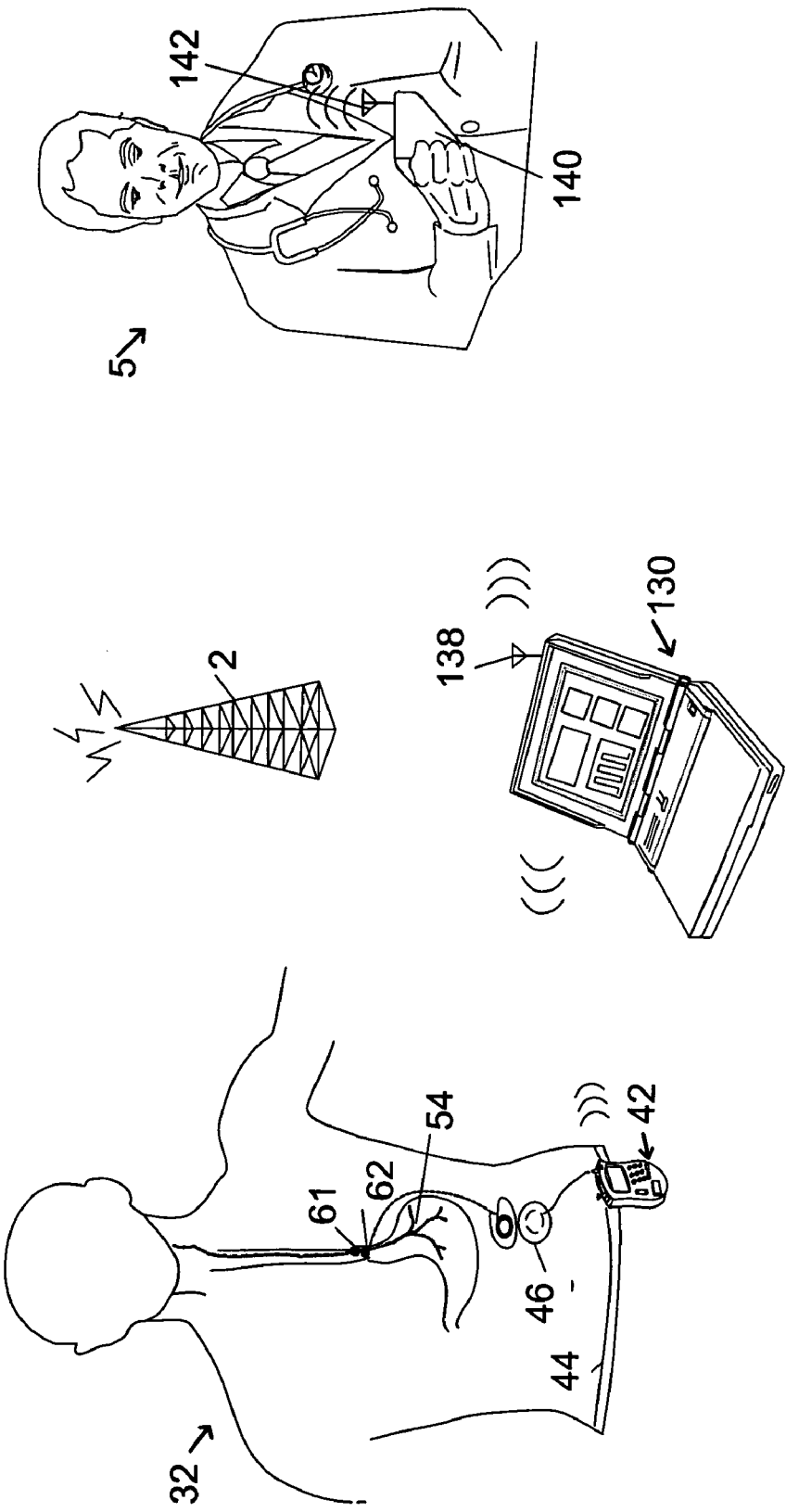
Figure 1D:
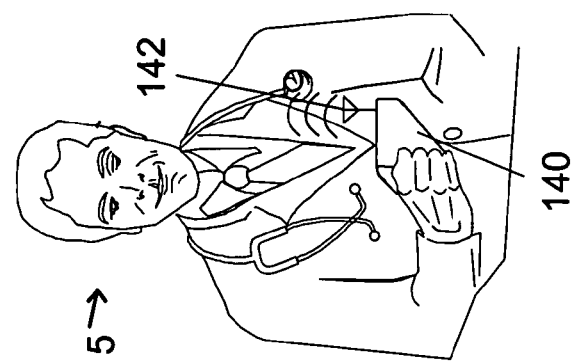
Figure 1D:
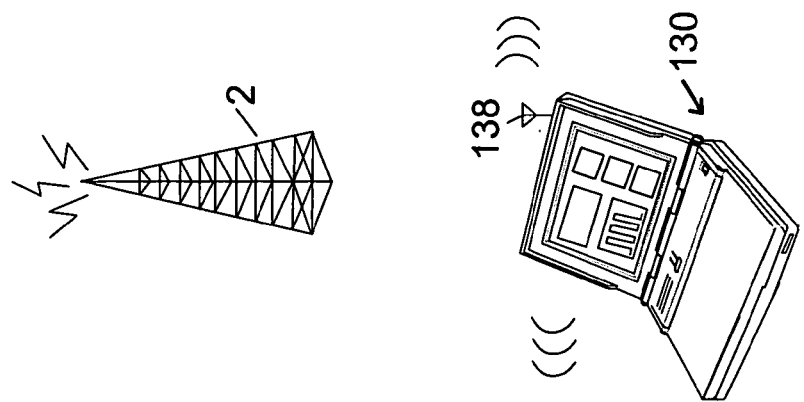
Figure 1D:
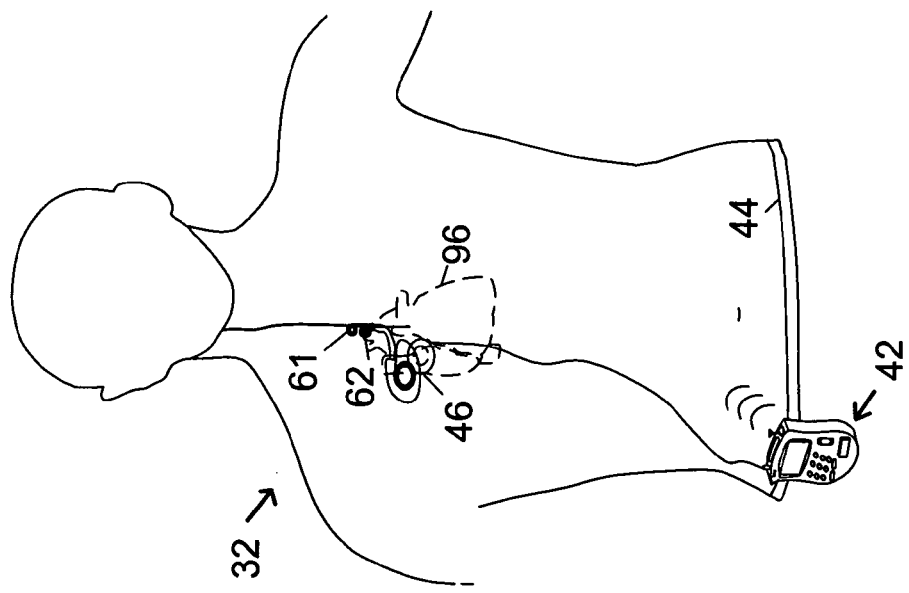
Figure 1E:
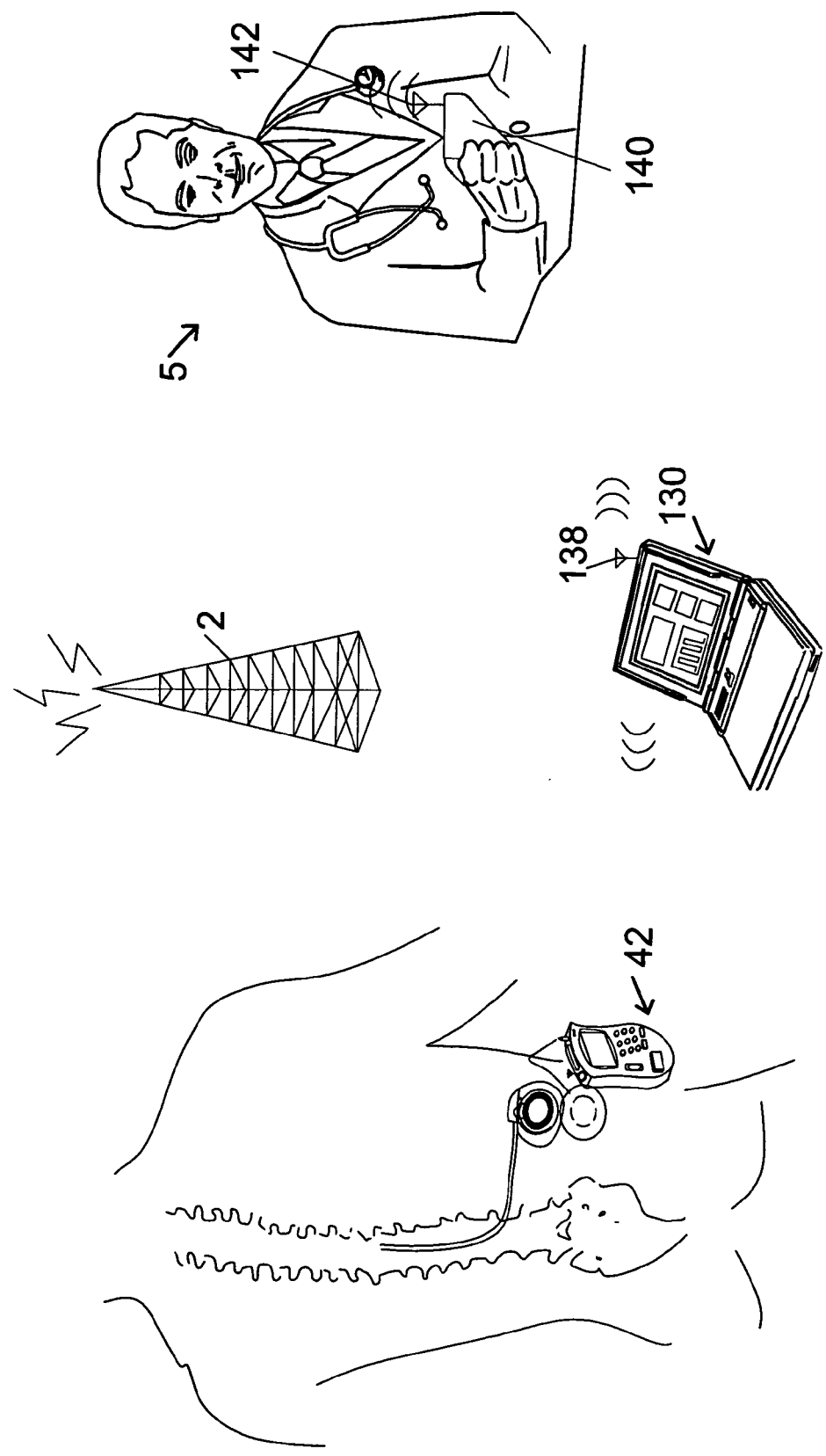
Figure 2A:
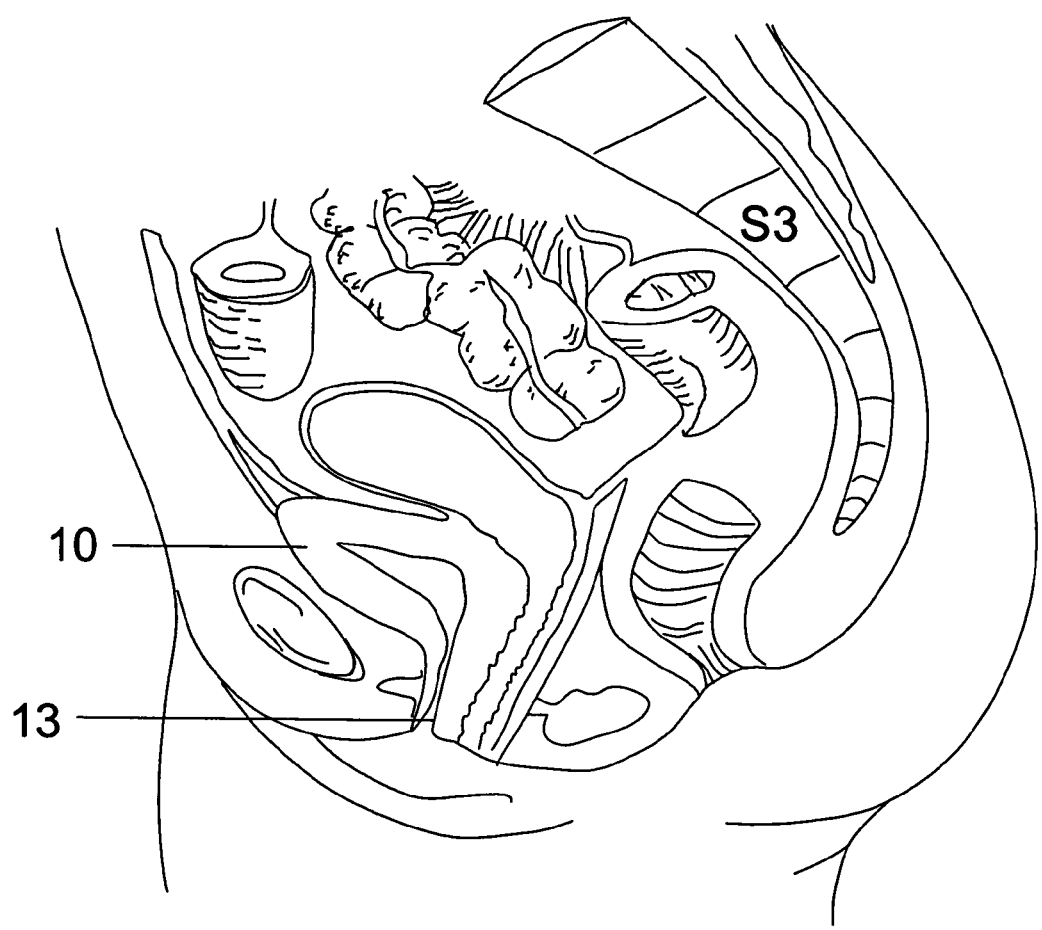
FIG. 2A is a diagram of the sagital section of the female pelvis, showing the relationship between various anatomic structures.
Figure 2B:
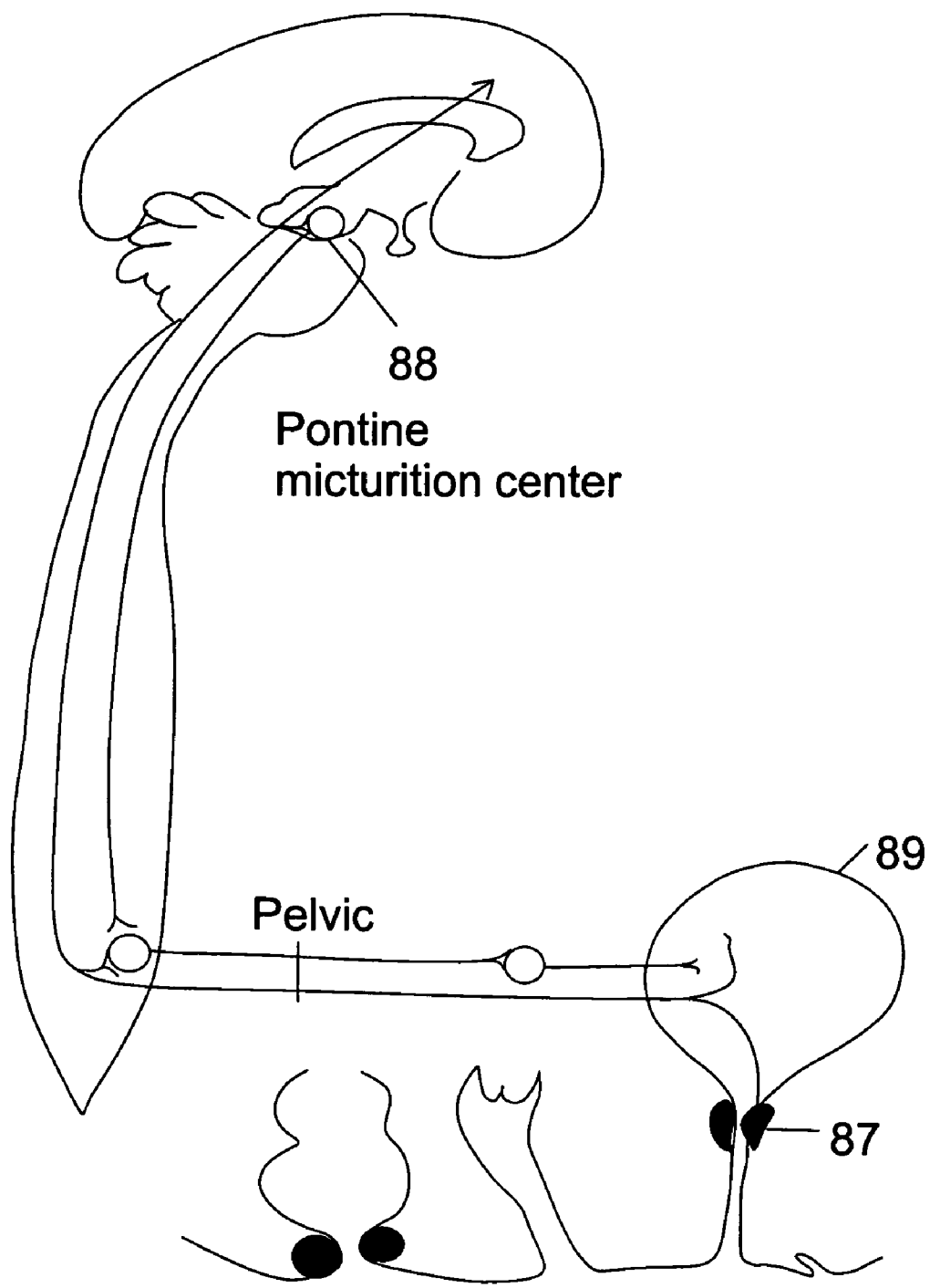
FIG. 2B is a schematic diagram showing physiological control of micturition.
Figure 3:
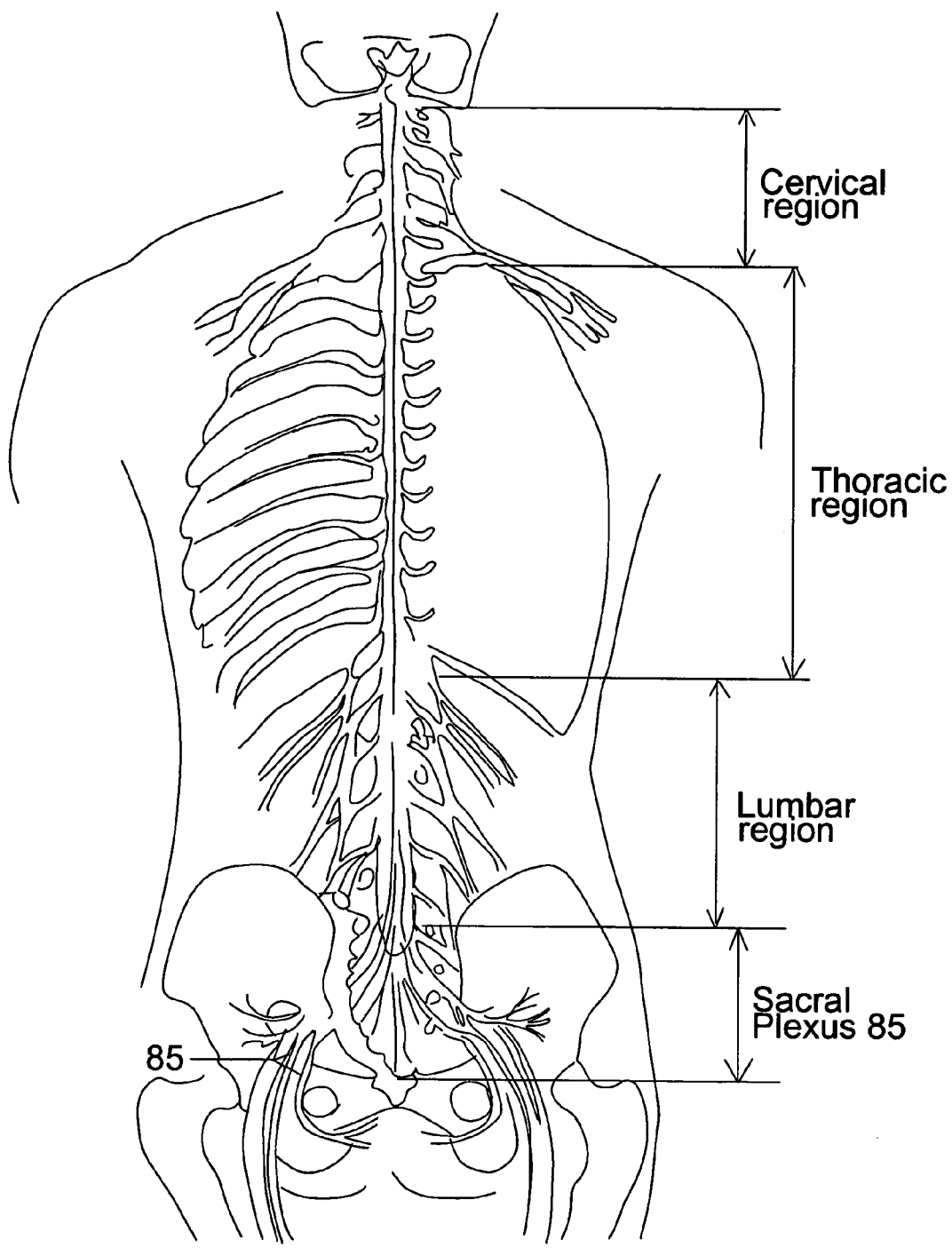
FIG. 3 is a diagram showing anatomic relationships of the spinal nerves and sacral plexus.
Figure 4:
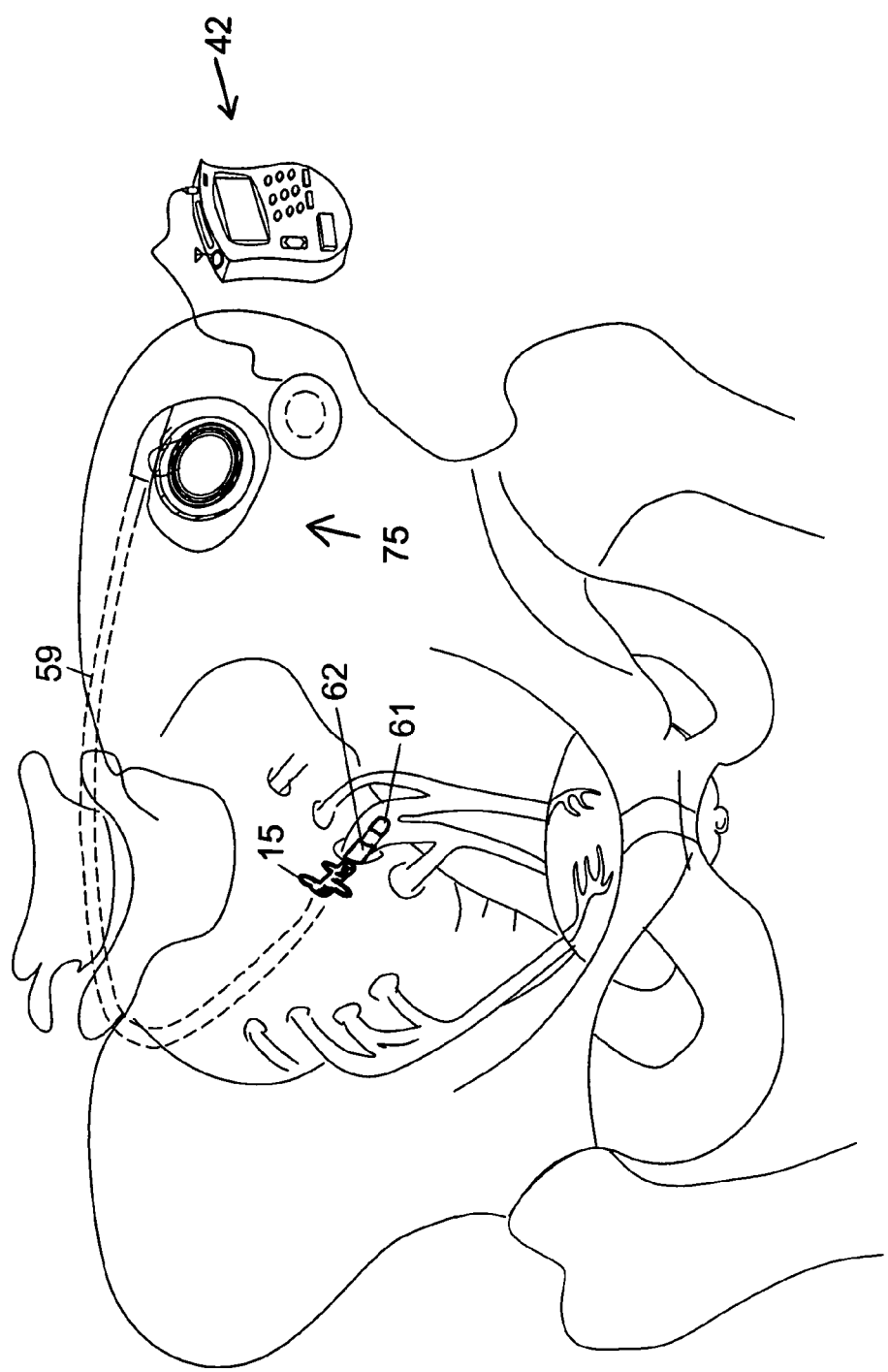
FIG. 4 is a schematic diagram of the sacral region showing electrodes in sacral foraman, and placement of the implanted stimulator.
Figure 5:
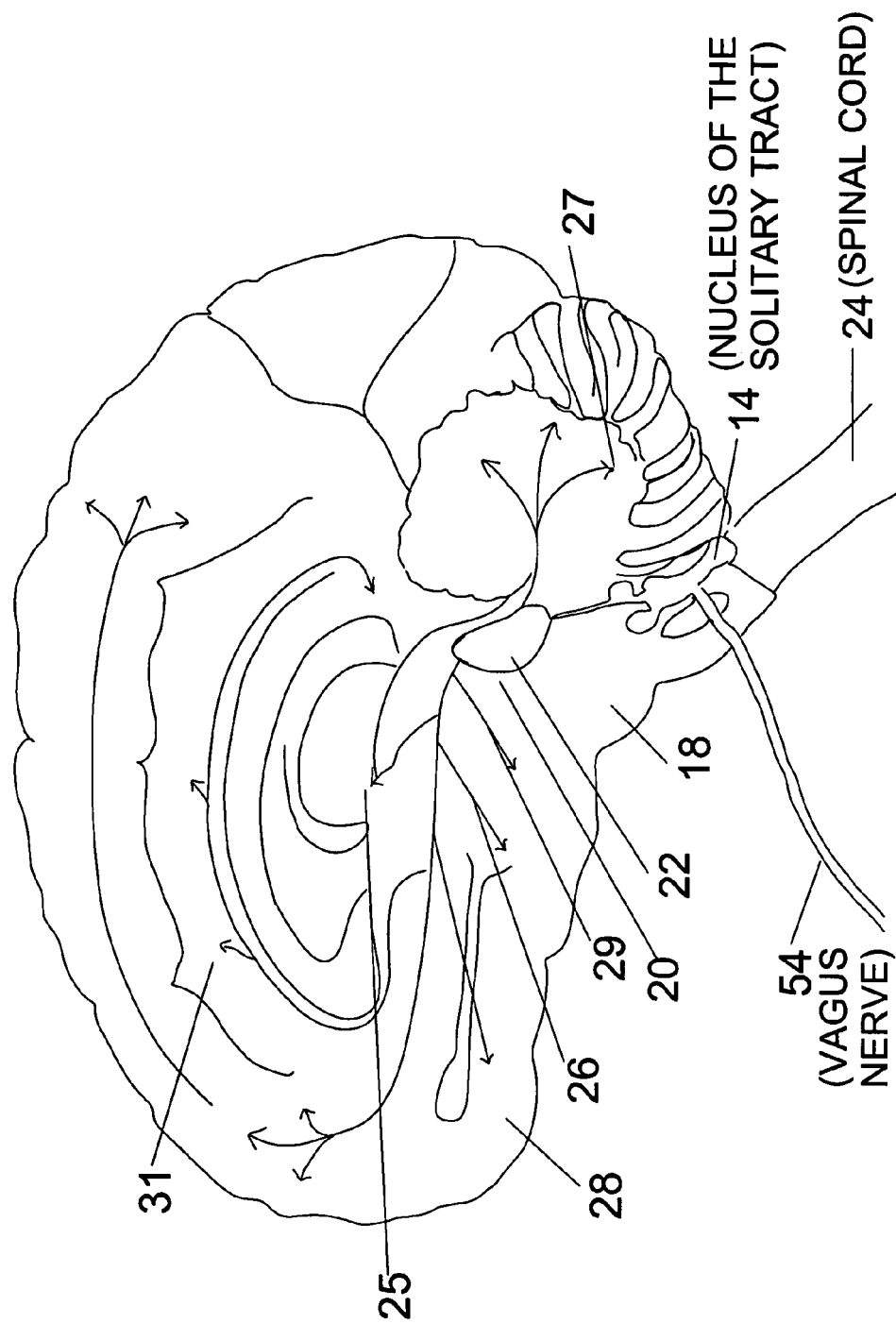
FIG. 5 is a diagram of the lateral view of the brain and spinal cord, with its relationship to the vagus nerve.
Figure 6:
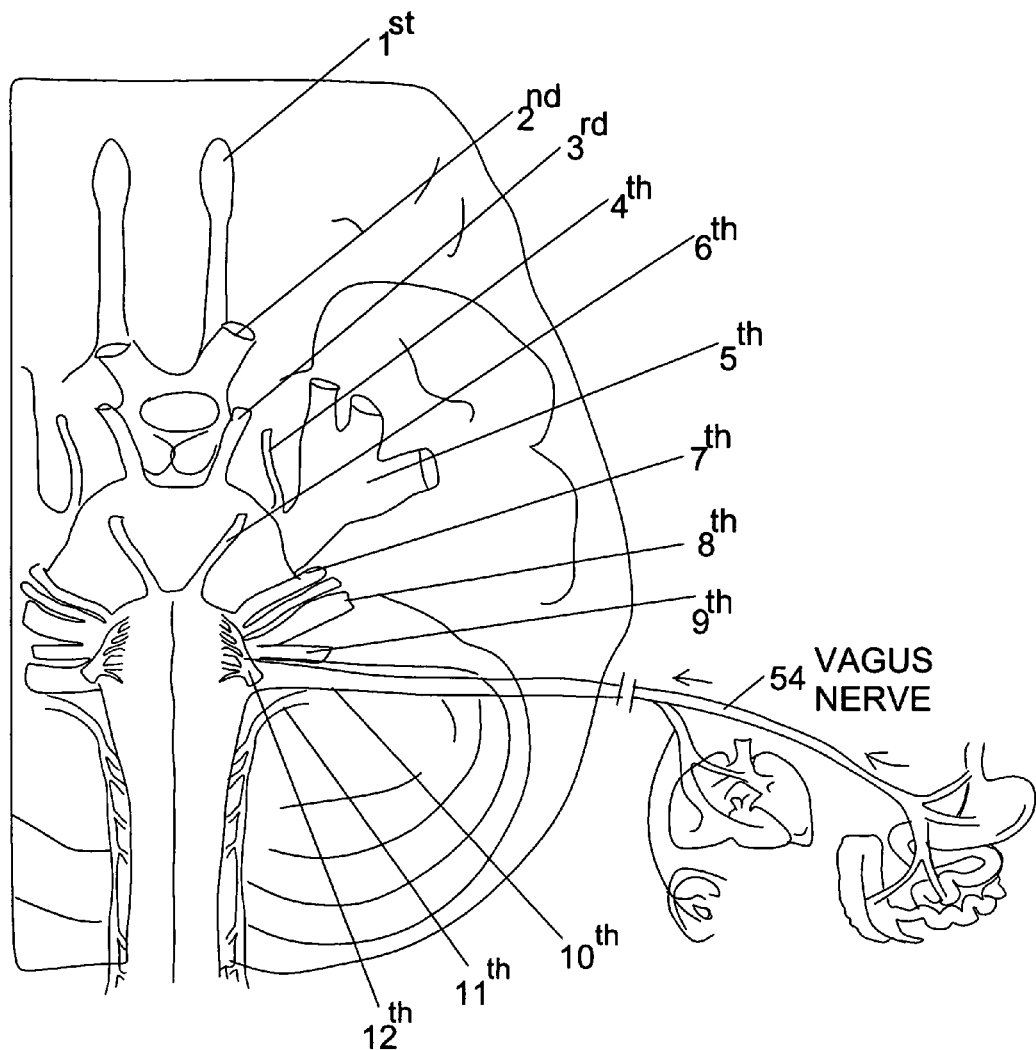
FIG. 6 is a diagram of the base of brain showing the relationship of vagus nerve to the other cranial nerves.
Figure 7:
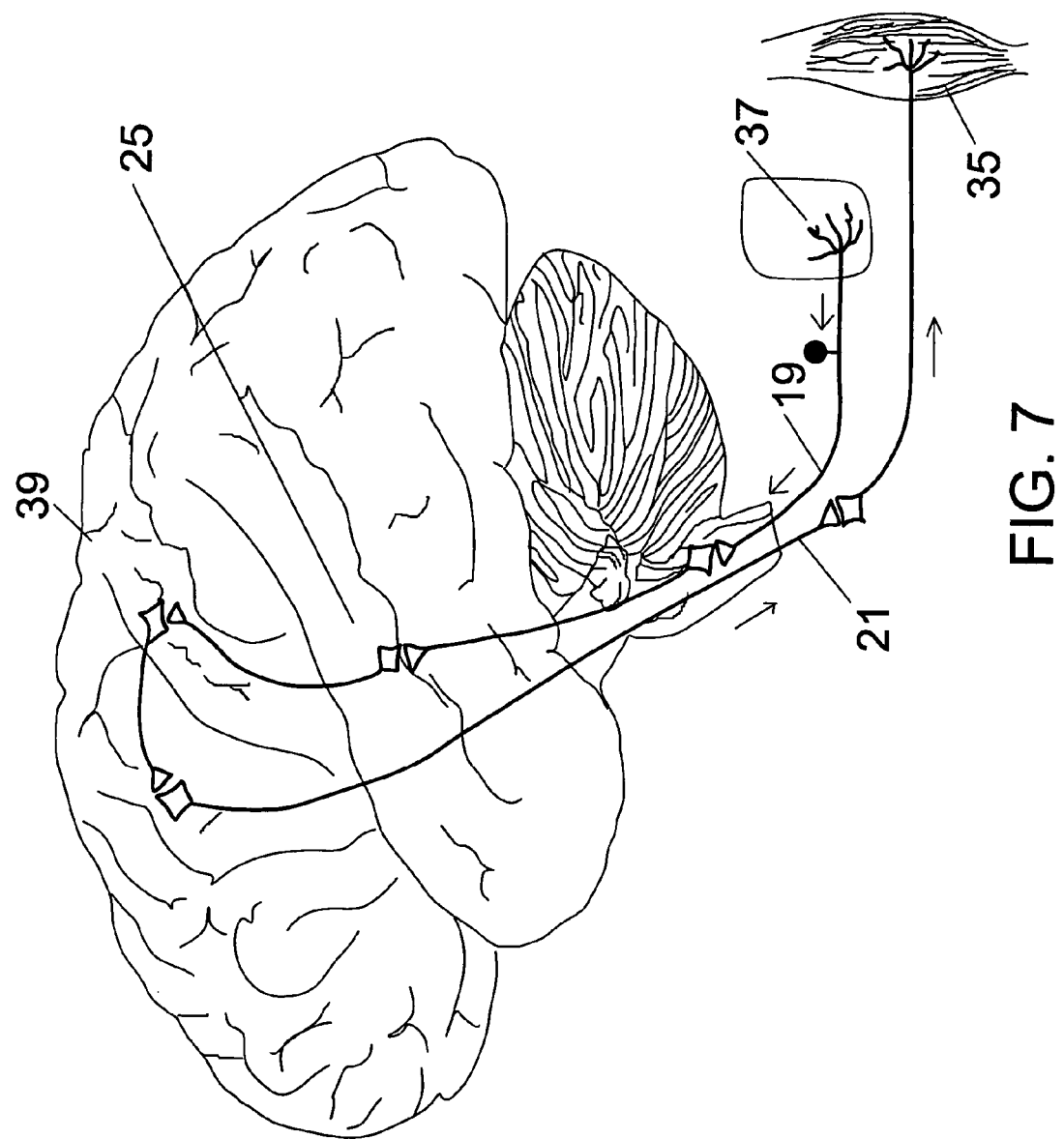
FIG. 7 is a diagram of the brain showing afferent and efferent pathways.
Figure 8:
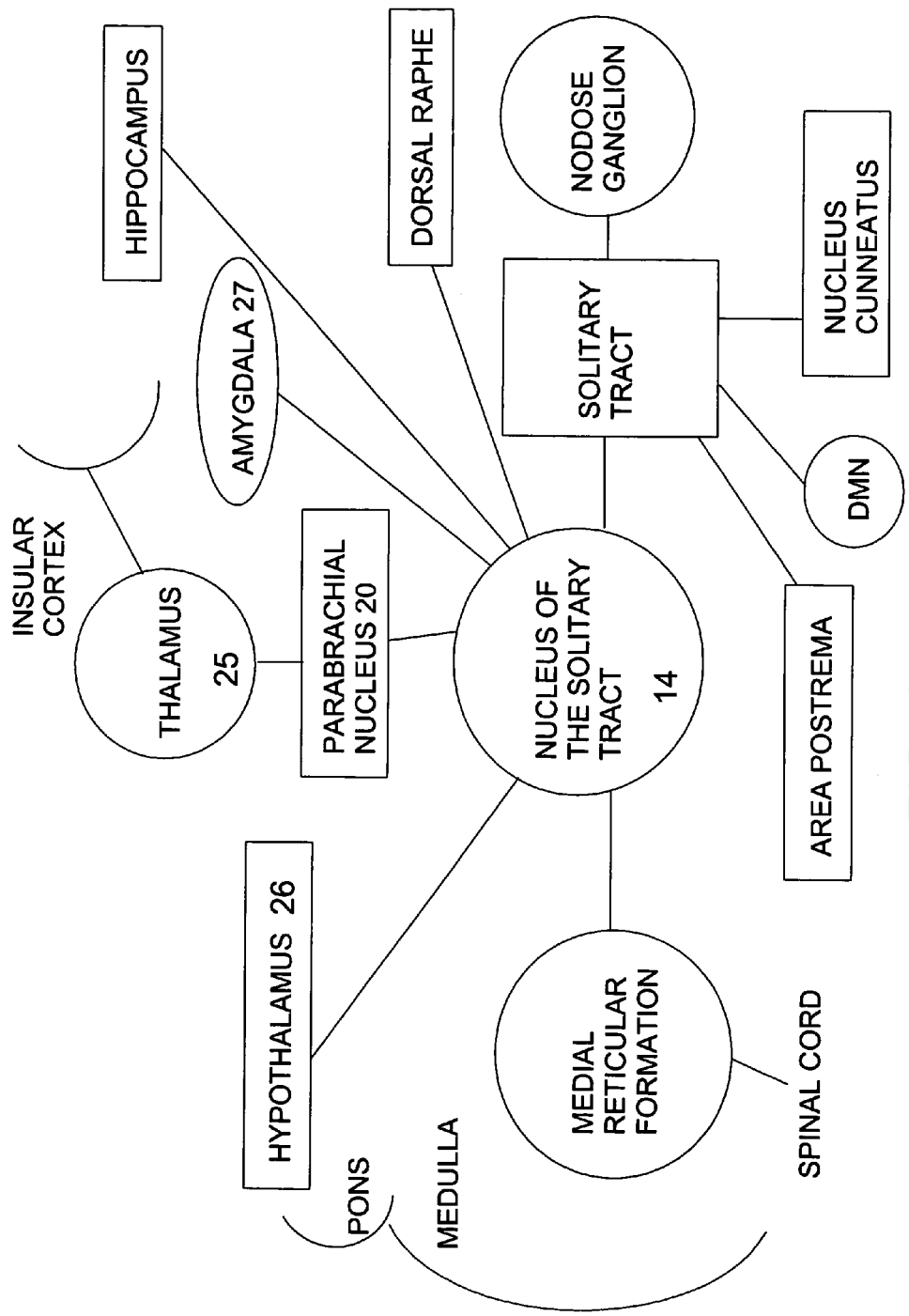
FIG. 8 is a schematic diagram showing relationship of Nucleus of the Solitary Track and how it relays information to other parts of the brain.
Figure 9:
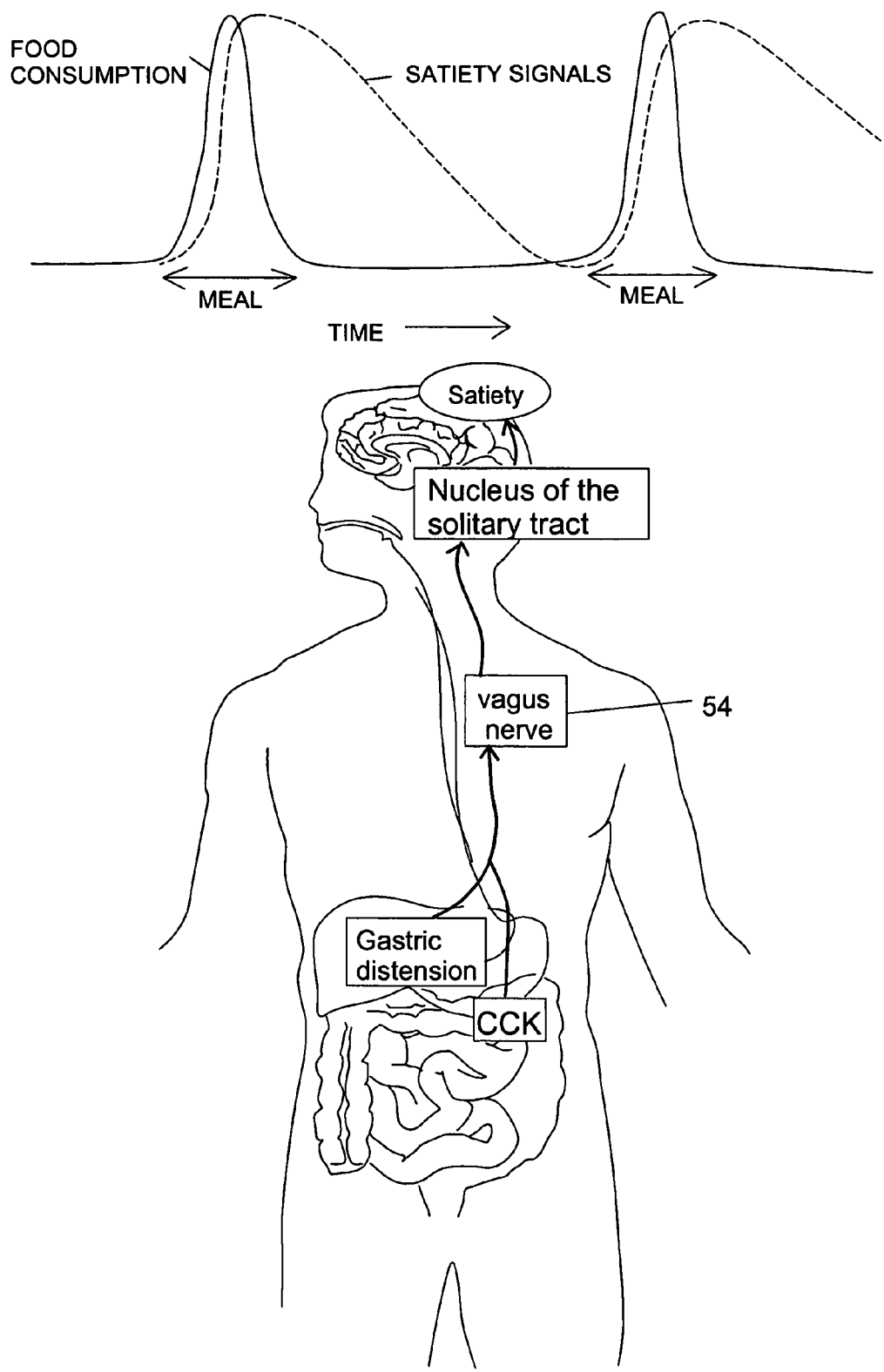
FIG. 9 is a diagram showing the relationship of food consumption and afferent signals for satiety being carried over the vagus nerve in a patient.
Figure 10:
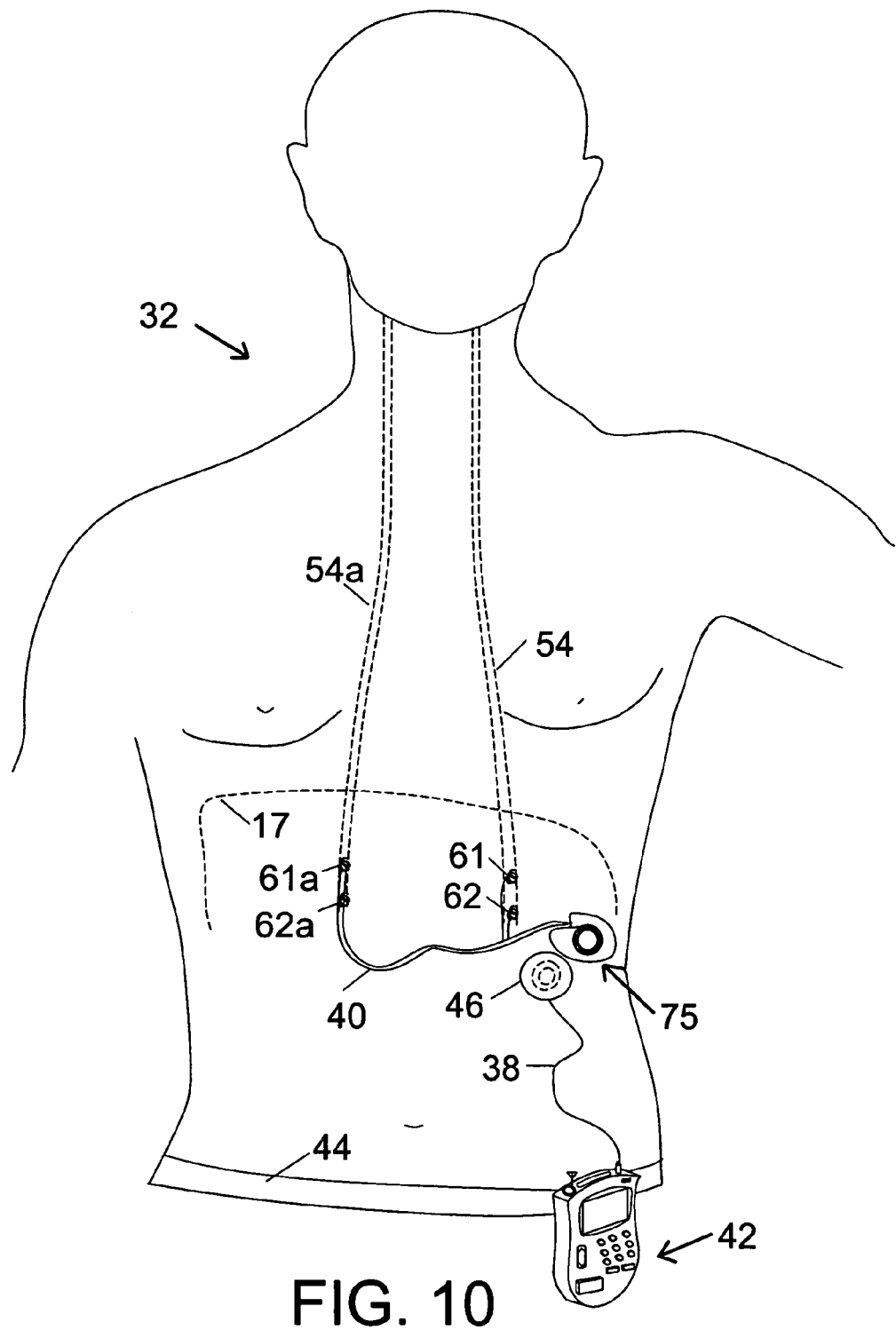
FIG. 10 is a diagram showing bilateral vagus nerve stimulation.
Figure 11:
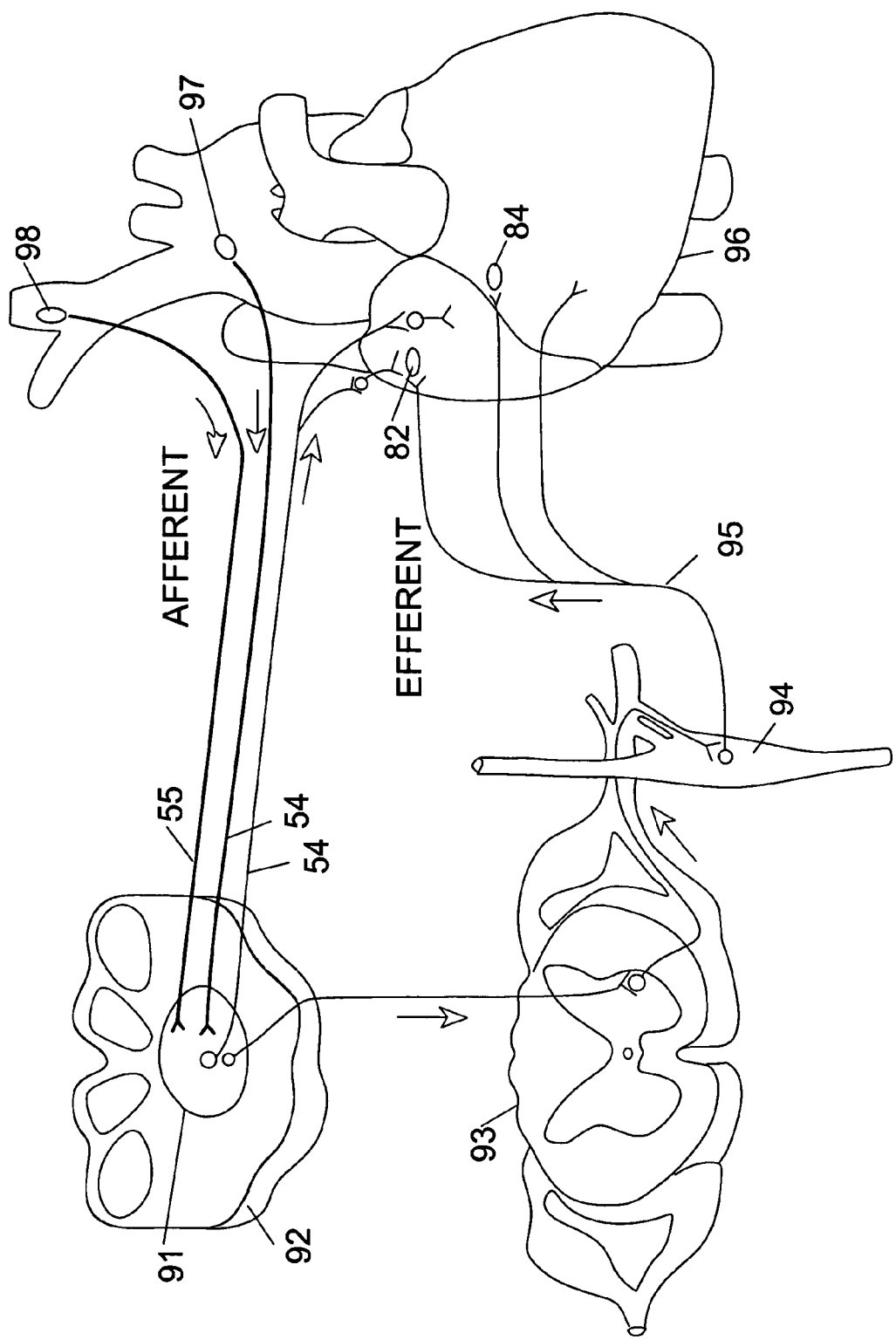
FIG. 11 is a simplified schematic diagram showing nervous control of the heart.
Figure 12:
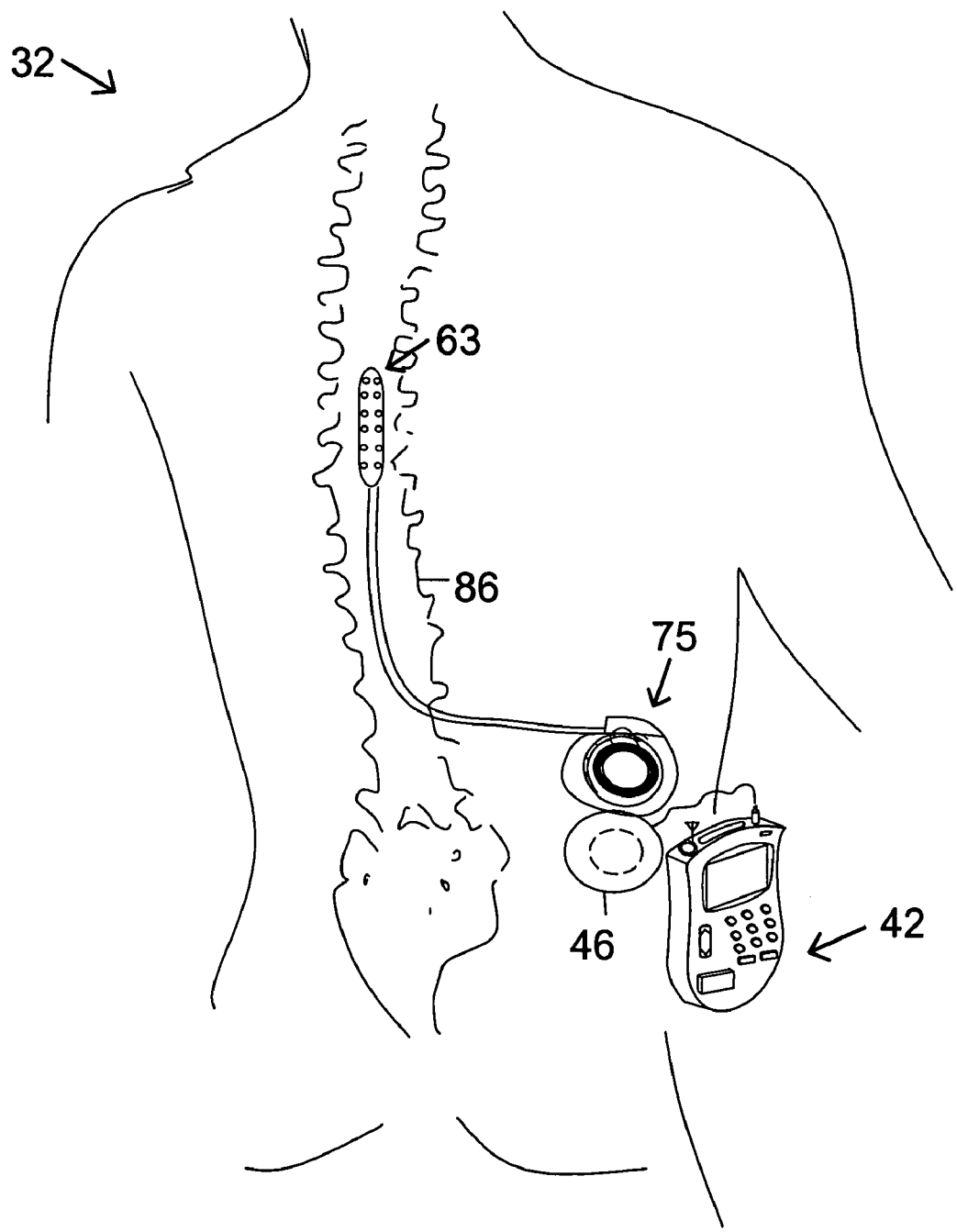
FIG. 12 is a diagram showing lead, implanted stimulator, and interface unit for spinal cord stimulation.

The implanted stimulator 75 can be used to provide neuromodulation therapy for a host of medical disorders. FIG. 1A, depicts an implantable stimulator 75 for providing pulsed electrical stimulation to the left vagus nerve, for providing neuromodulation therapy for neurological and neuropsychiatric disorders such as epilepsy, depression, anxiety disorders, Alzheimer's disease and the like. FIG. 1B, depicts an implantable stimulator 75 for providing pulsed electrical stimulation to the sacral plexus, for providing neuromodulation therapy for urinary incontinence and the like. FIG. 1C, depicts an implantable stimulator 75 for providing pulsed electrical stimulation to the vagus nerve at around the diaphramatic level, for providing neuromodulation therapy for obesity and obsessive eating disorders. FIG. 1D, depicts an implantable stimulator 75 for providing pulsed electrical stimulation to the right vagus nerve, for providing neuromodulation therapy for cardiovascular disorders including atrial fibrillation, congestive heart failure and the like. FIG. 1E, depicts an implantable stimulator 75 for providing pulsed electrical stimulation to the spinal cord, for providing neuromodulation therapy for intractable pain.

Figure 18A:
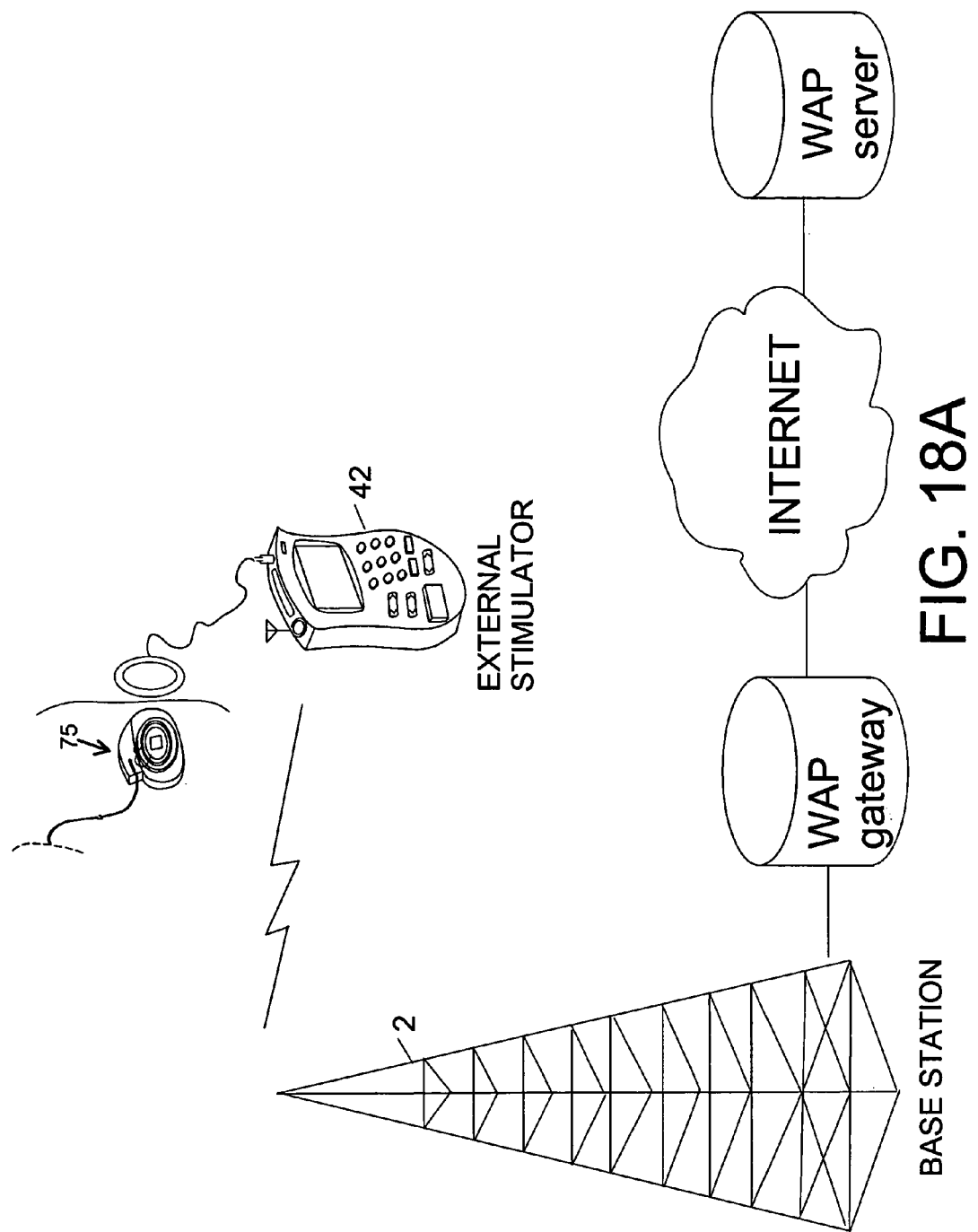
FIG. 18A is a diagram showing communication of the external stimulator over the internet.
Figure 18B:
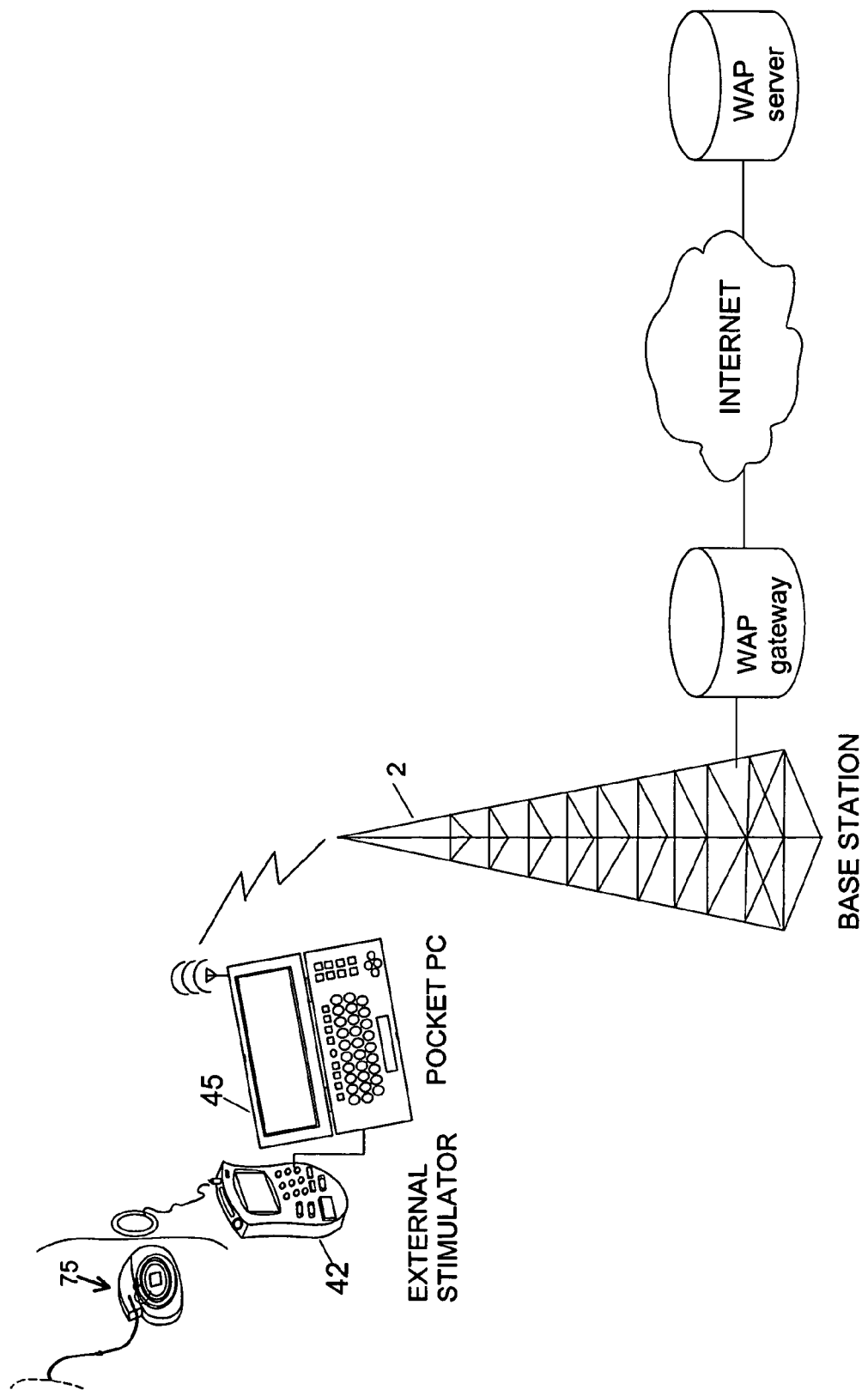
FIG. 18B is a diagram showing internet communication of the external stimulator, via a portable PC.

In each case, the IU/stim 42 (FIGS. 1A-1E, 13) comprises telemetry module for communication and data exchange with a mobile device 140 (modified PDA/cell phone 140). The IU/stim 42 is inductively coupled to the implanted stimulator 75. In an alternative embodiment, the telemetry module may be separate, and may be connected to the external stimulator via a cable, as is shown in FIG. 18B. In this disclosure the terms mobile device (MD) 140 and modified PDA/cell phone 140 are used interchangeably.

Figure 14:
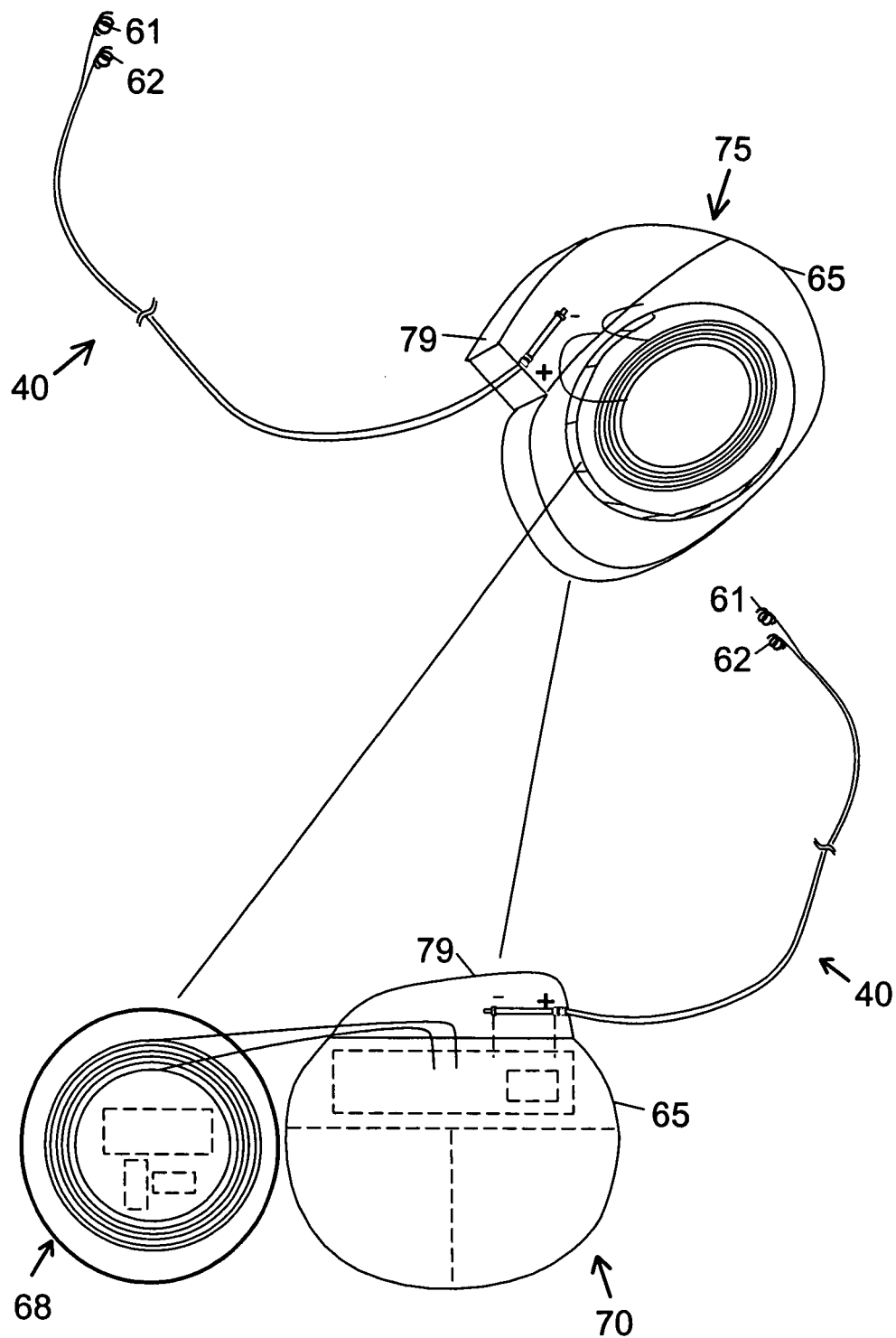
FIG. 14 is a diagram showing the two modules of the implanted stimulator.

FIG. 14 shows a close up view of the implanted stimulator 75, showing the two subassemblies 68, 70. The two subassemblies are the stimulus-receiver module 68 and the battery operated pulse generator module 70. The stimulus-receiver module 68 works in conjunction with an IU/stim 42. The IU/stim 42 (FIGS. 1A-1E, 13) and a programmer are remotely controllable from a distant location via the Internet. Controlling circuitry within the implanted stimulator 75, makes the inductively coupled stimulator and the IPG operate in harmony with each other. For example, when stimulation is applied via the inductively coupled system, the battery operated portion of the stimulator is triggered to go into the "sleep" mode. Conversely, when programming pulses (which are also inductively coupled) are being applied to the implanted battery operated pulse generator, the inductively coupled stimulation circuitry is disconnected.

Figure 15:
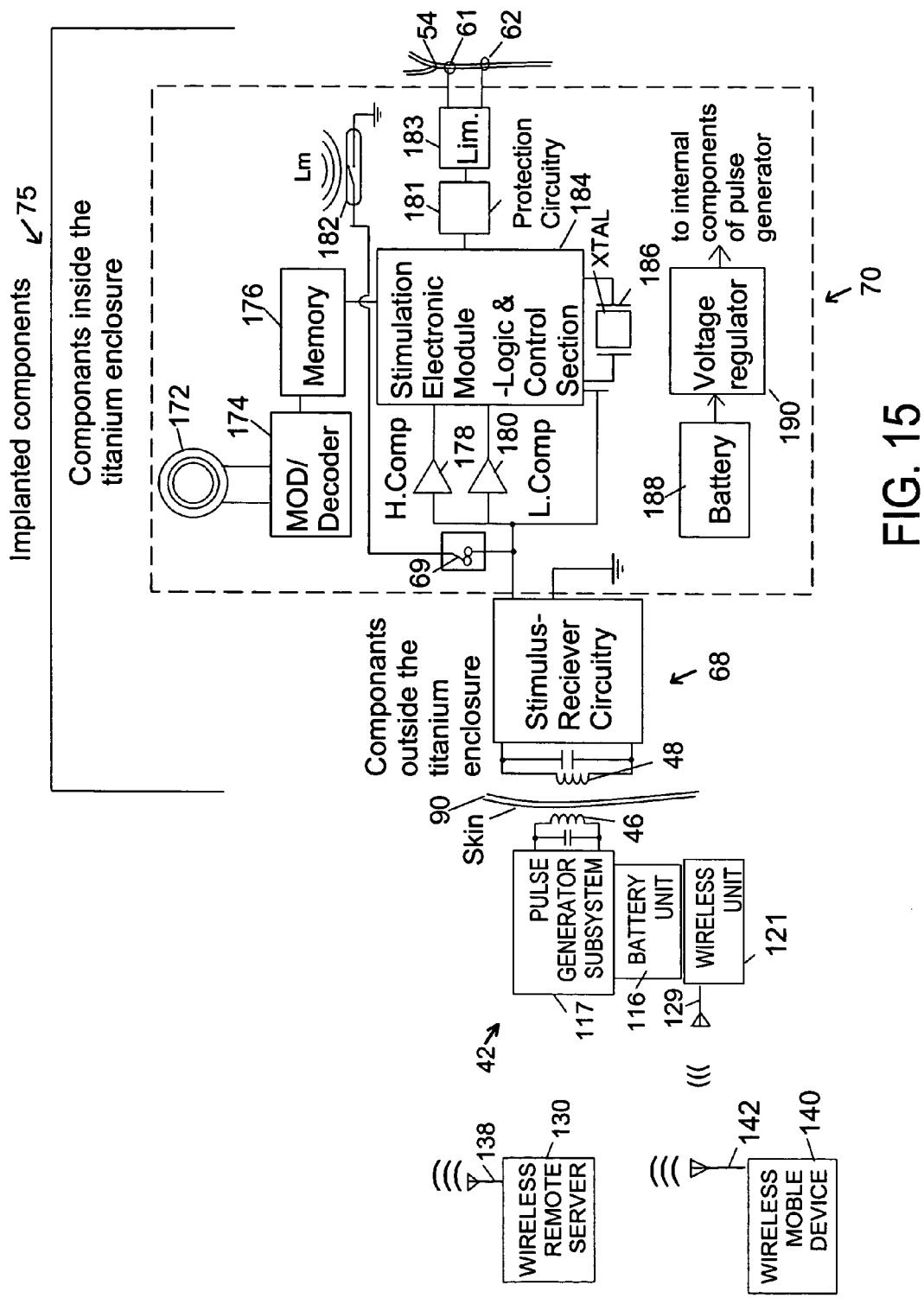
FIG. 15 shows details of implanted pulse generator.

A simplified schematic and block diagram of the implantable stimulator 75 is shown in FIG. 15. The inductively coupled stimulus-receiver module 68 is shown on the left part of the implanted components, and the battery-operated portion 70 is shown on right side of the diagram. The battery-operated portion 70 is also referred to as IPG 70, implanted pulse generator 70, stimulator subassembly 70, and battery-operated module 70 in this disclosure. Much of the circuitry included within this embodiment of the IPG 70 is realized on a single application specific integrated circuit (ASIC). This allows the overall size of the IPG 70, to be quite small and readily housed within a suitable hermetically-sealed case, such as one made of titanium. Using CMOS technology and monolithic design, the analog and digital functions are integrated on a silicon chip approximately 5 mm×5 mm in size. Hybrid technology being used as a reliable connection technology for the wiring of the IC with non-integrated discrete components (like quartz oscillators, tantalum capacitors, coils of transmission, reed contacts, etc).

Figure 16:
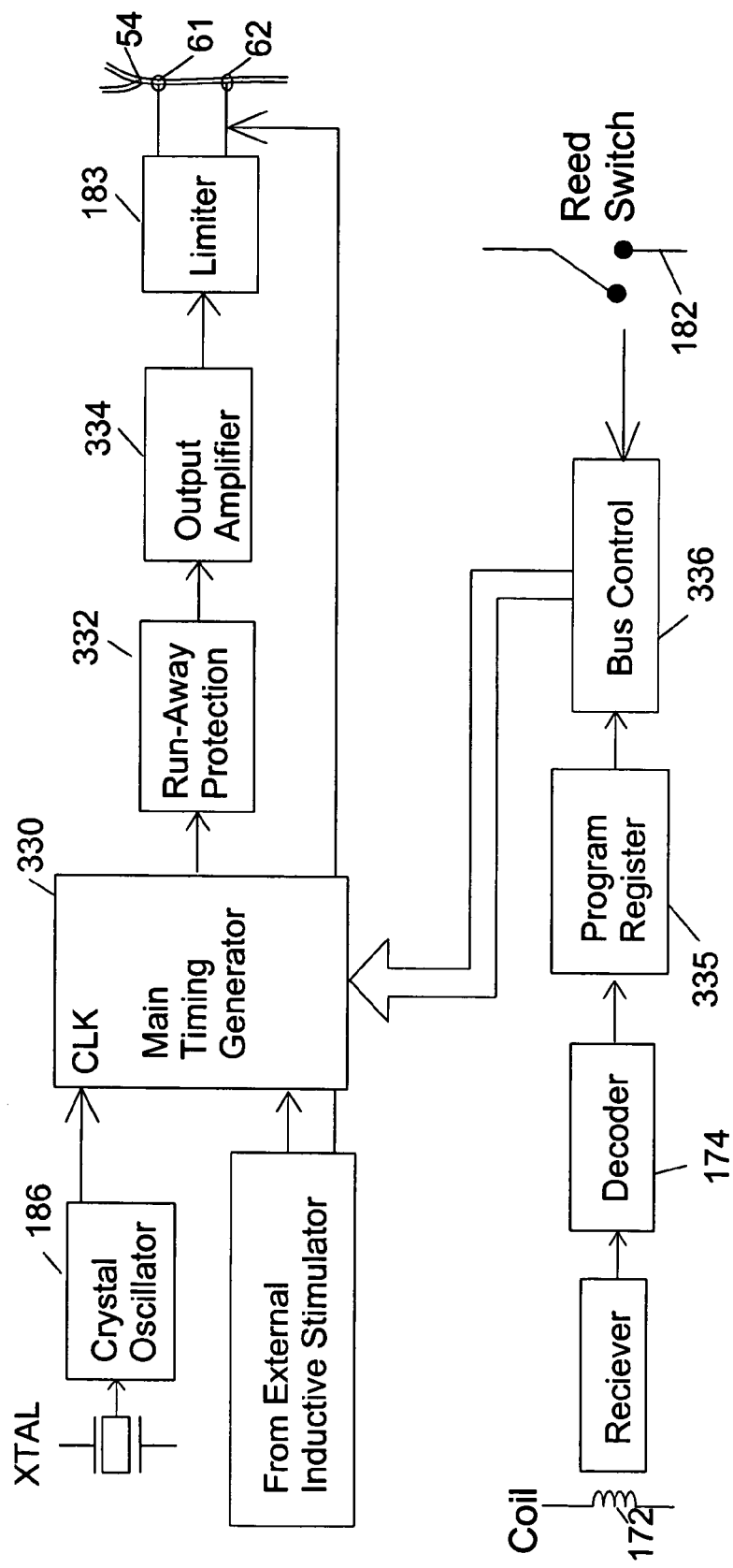
FIG. 16 shows details of digital components of the implantable circuitry.
Figure 17:
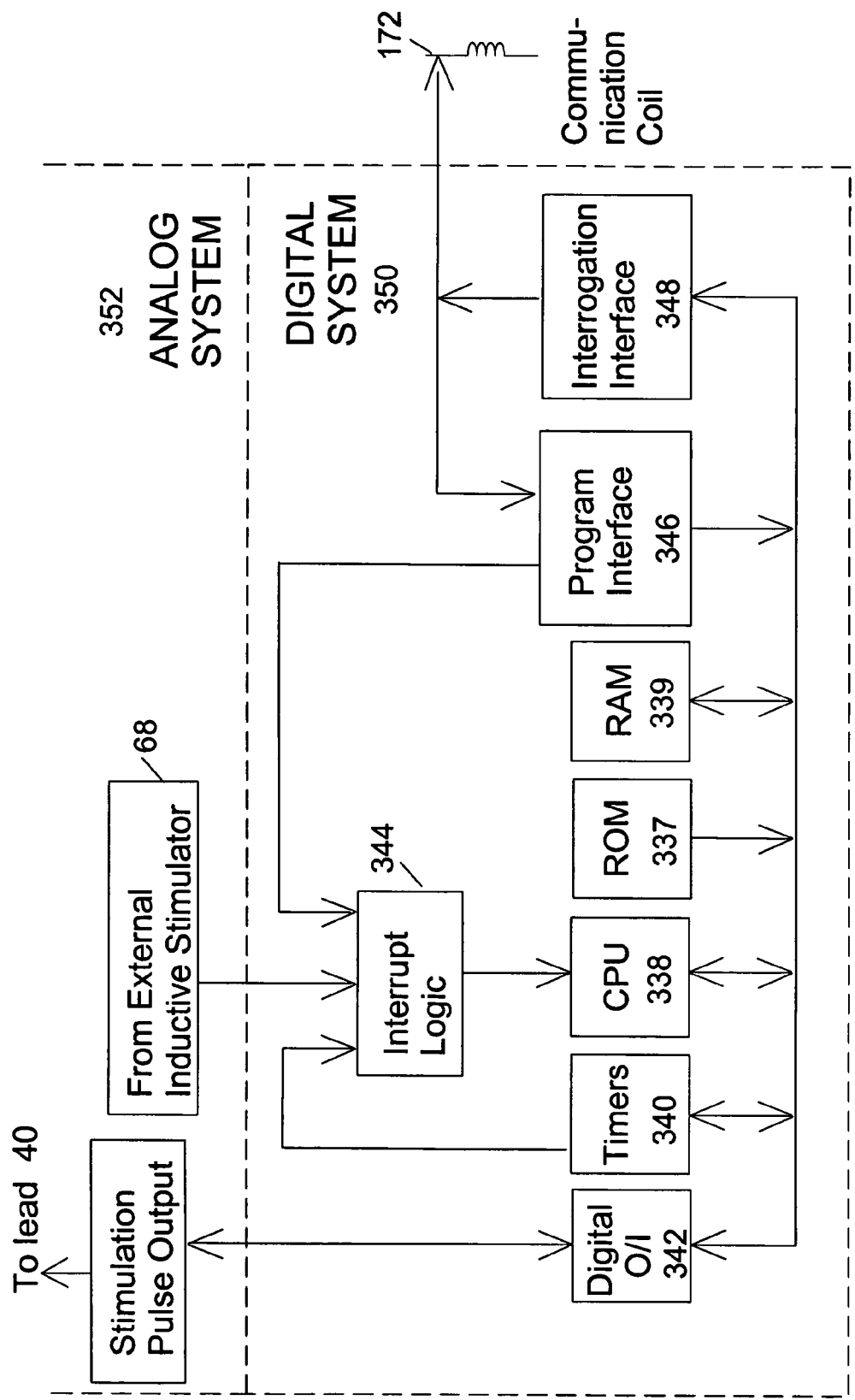
FIG. 17 shows details of the analog and digital systems.

The battery-operated portion of the system 70 shown on the right side of FIG. 15 is described in conjunction with FIGS. 16 and 17. The stimulation electronic module 184 comprises both digital and analog circuits. The main timing generator 330 (shown in FIG. 16), controls the timing of the analog output circuitry for delivering neuromodulating pulses to the nerve tissue, via output amplifier 334. Limiter 183 prevents excessive stimulation energy from getting into the nerve tissue. The main timing generator 330 receiving clock pulses from crystal oscillator 186. Main timing generator 330 also receiving input from inductively coupled circuitry 68, and programmer 109 via coil 172. FIG. 17 highlights other portions of the digital system such as CPU 338, ROM 337, RAM 339, program interface 346, interrogation interface 348, timers 340, and digital O/I 342.

Most of the digital functional circuitry 350 is on a single chip (IC). This monolithic chip along with other IC's and components such as capacitors and the input protection diodes are assembled together on a hybrid circuit. As well known in the art, hybrid technology is used to establish the connections between the circuit and the other passive components. The integrated circuit is hermetically encapsulated in a chip carrier. A coil situated under the hybrid substrate is used for bi-directional telemetry. For the implanted battery portion 70, the hybrid and battery 188 are encased in a titanium can 65. This housing is a two-part titanium capsule that is hermetically sealed by laser welding. Alternatively electron-beam welding can also be used. The header 79 (FIG. 14) is a cast epoxy-resin with hermetically sealed feed-through, and form the lead 40 connection block. The stimulus-receiver assembly 68 is then also assembled on to the pulse generator 70 to finish the complete implanted stimulator 75.

The implantable stimulator 75 is implanted in a patient, in the usual fashion by making an incision to expose the nerve tissue for placement of the stimulating electrodes. One pair of electrodes is placed for unilateral stimulation or two pairs of electrodes are placed (using 2 leads) for bilateral stimulation indications. A second incision is made for making a subcutaneous pocket for the implantable stimulator 75. The lead is subcutaneously tunneled and connected to the implantable stimulator 75. The single lead 40 or both leads are connected to the pulse generator 75. The pulse generator 75 is placed in a bluntly dissected pocket. The incisions are closed in layers in the usual manner, and stimulation can begin after the tissues are healed (approximately 2 weeks).

Once implanted, in the system and method of this invention, pulsed electrical stimulation to the nerve tissue can be performed either via an IU/stim 42 in conjunction with the stimulus-receiver module 68, or via the implanted pulse generator 70 according to parameters which are programmed via an external programmer. The IU/stim 42 has a telemetry module and can be controlled remotely via the Internet. A physician or medical personnel situated remotely is able to interrogate and selectively program the IU/stim 42 via a modified PDA/cell phone 140. As shown in FIGS. 18A and 18B, the telemetry module within the external stimulator wirelessly communicates with a base station 2, either directly as shown in FIG. 18A, or via an attachment as shown in FIG. 18B.

Figure 19:
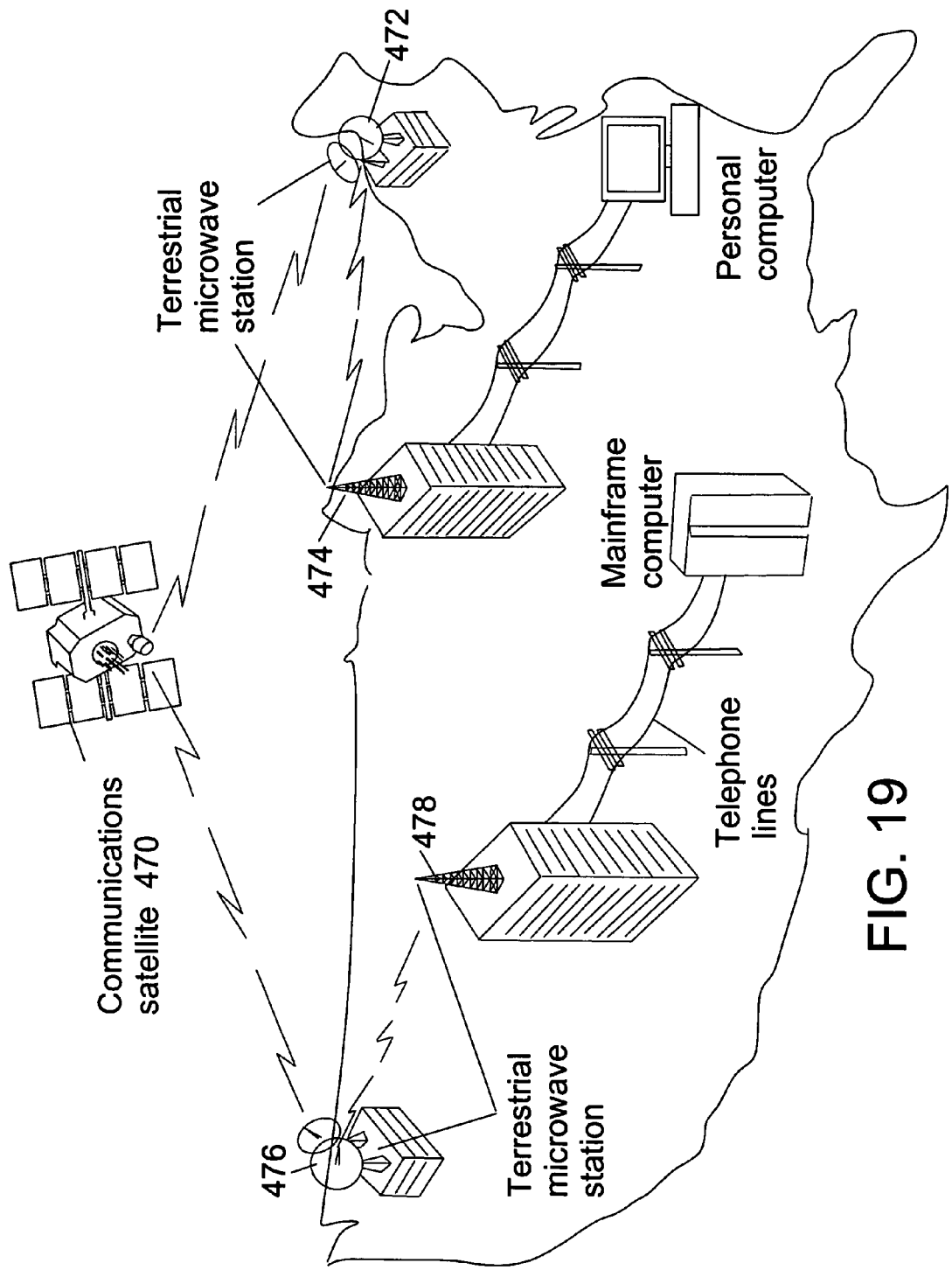
FIG. 19 is a diagram showing the interrelationship of satellite, microwave, and telephone lines communications.
Figure 20:
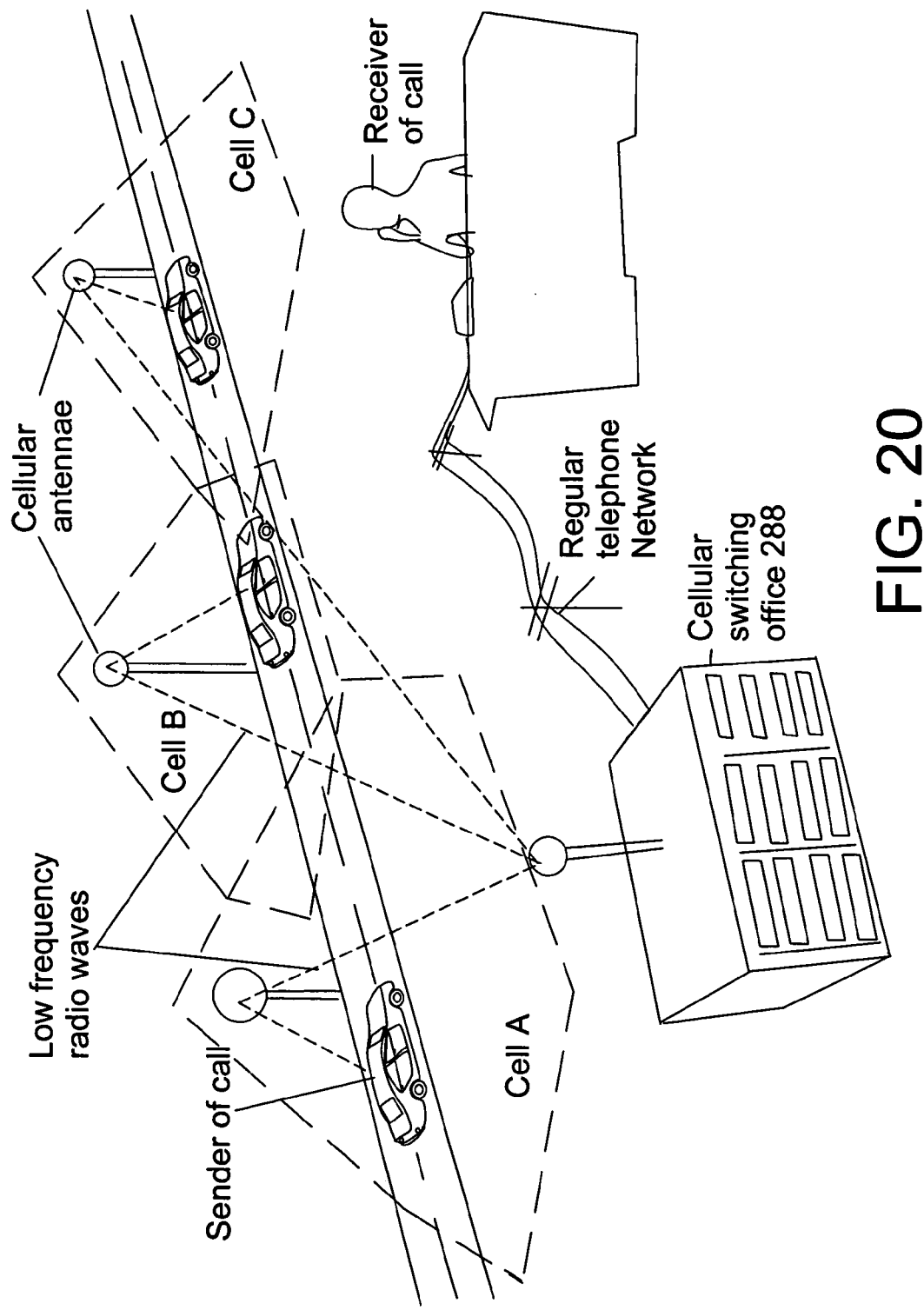
FIG. 20 is a diagram showing the relationship of cellular and telephone network communications.

The communications technology used may be microwave and satellite technology (shown in FIG. 19), or may be cellular technology (shown in FIG. 20). In microwave and satellite technology, all types of data can be converted to microwave impulses and transmitted through the air. As shown in FIG. 19, microwaves signals can be sent in two ways: via microwave stations or via satellites. Both can transmit data in large quantities and at high speeds, and are ideal for Internet downloads.

Terrestrial (earth-based) microwave station can communicate with each other directly over distances of no more than about 30 miles or so. The stations use line-of-sight transmission. Communications satellites which are placed into orbit around the earth to receive and transmit microwave signals to and from terrestrial microwave stations. Traditional satellites maintain a geosynchronous orbit. Such satellites are so far above the surface of the earth that it takes only two or three of them to blanket the entire planet. Such geosynchronous satellites are excellent for transmitting data. In addition Low earth orbit (LEO) satellite systems, which were developed for telephone communication may also be used.

Shown in conjunction with FIG. 20, cellular technology which is widely used for cellular phones. Cellular phones of course keep contact with cellular antennae which are strategically placed throughout a calling area. Calling areas are divided into honeycomb-shaped cells, each measuring 10 miles wide or so and containing its own antennae. The antennae provide an interface with the regular public phone network via a switching office 288.

Figure 21:
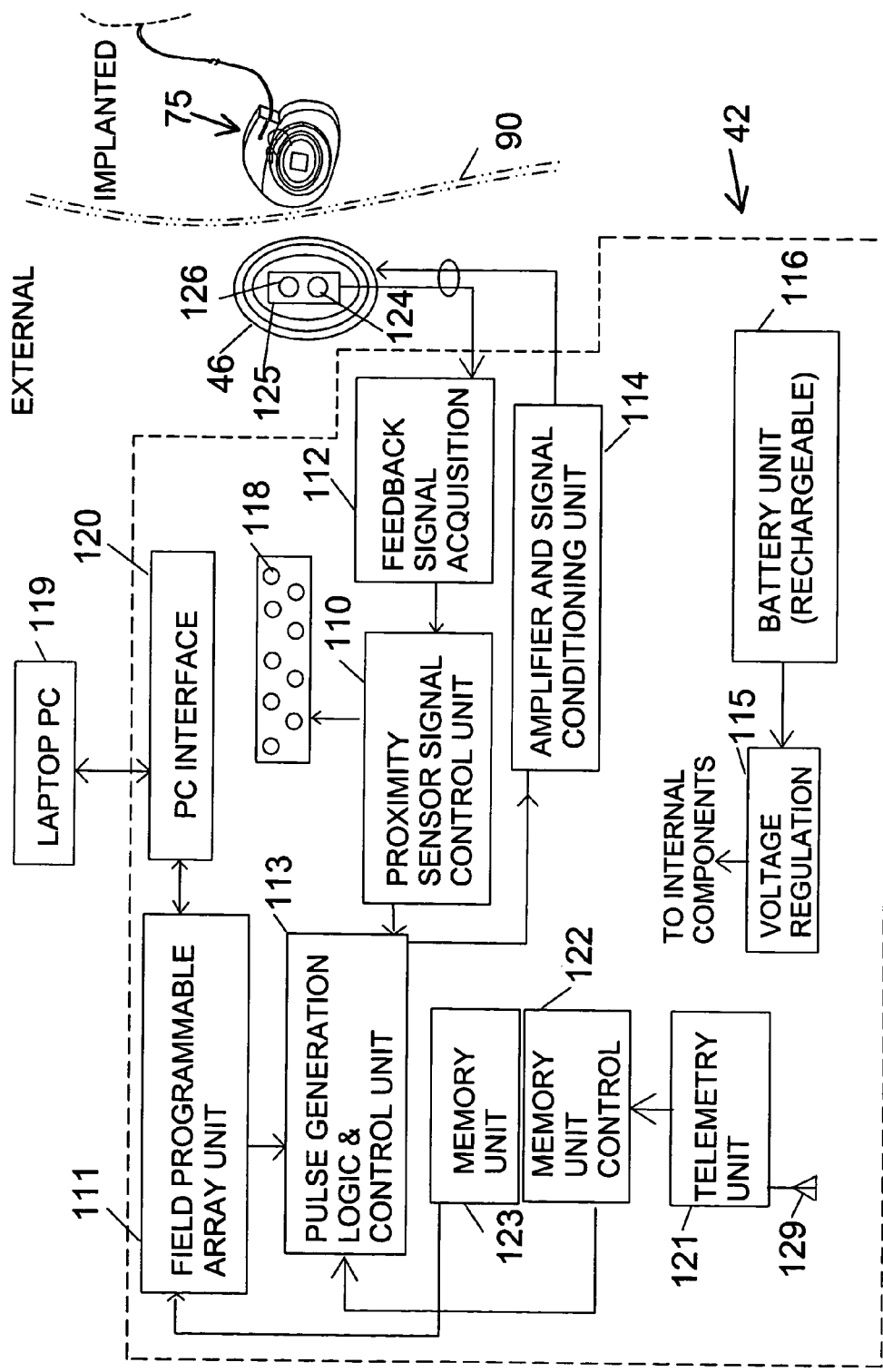
FIG. 21 is a diagram showing the primary and secondary coils separated by skin, and the components of the implantable stimulator.

The IU/stim 42 of the presently preferred embodiment, and its components are shown schematically in FIG. 21. The major components of the IU/stim 42 are the pulse generator subsystem 117, the battery unit 116, and the wireless unit (telemetry) 121. A replaceable battery 116 is used for providing power to all parts of the IU/stim 42 circuitry. The telemetry component 121 provides wireless communication with the modified PDA/cell phone 140 using Wireless Application Protocol (WAP). The telemetry component 121 supports making variations to the parameters of a program. A laptop PC 119 can also be connected by a cable connection to the IU/stim 42 to load data or update programs. The IU/stim 42 is inductively coupled to the implanted stimulator 75. The implanted stimulator 75 has a pair of electrodes in contact with the nerve tissue to be stimulated, at the distal end.

The IU/stim 42 is composed of various modules or sub-assemblies, as shown in FIG. 21. The first sub-assembly is the pulse generation and signal conditioning components 113, 114, the second is the battery 116, and the third is the telemetry 121 and memory unit 123. The presently preferred embodiment, comprises an optional proximity sensing and feedback circuitry. The pulse generator is able to function as supplier of electric pulses to the nerve tissue without the proximity feedback loop. In the telemetry module, a wireless antenna 129 provides a means for communication to the IU/stim 42 and the wireless remote server 130. In one embodiment, a laptop PC 119 can be physically connected to the IU/stim 42 in a tethered manner for loading of new program parameters.

Also shown in conjunction with FIG. 21, several pre-packaged programs can also be stored in the memory unit 123. This represents memory with a readable and writeable portion and a non-volatile pre-programmable portion. A Field Programmable Array Unit (FPGA) 111 and a random access component (RAM) and Random addressable storage logic, facilitates the application of logic to edit and change the "current" parameters being utilized for pulse generation. The PC interface 120 provides an interface to portable computer system 119, which allows re-loading of a new set of programs. The pulse generation component 113 generates pulses of well-defined parameters, which are amplified and conditioned at the amplifier and signal conditioning unit 114, which then provides these signals to the primary (external) inductive coil 46. In one embodiment, the sensor unit 126 has a pair of sensors which sense the position of an implanted magnet, and the sensor signal is fed back to the proximity sensor control block 110 via the feedback signal conditioning unit 112. The feedback signal provides a proportional signal for modification of the frequency, amplitude and pulse-width of the pulse being generated by the pulse signal generator unit 113. The sensor unit 126 has two sensors 124, 125 that sense the location of the implanted magnet. In one embodiment, the implanted (secondary) coil 48 is rigidly connected to the stimulus-receiver circuitry and a magnet, which are implanted under the skin 90.

Figure 22:
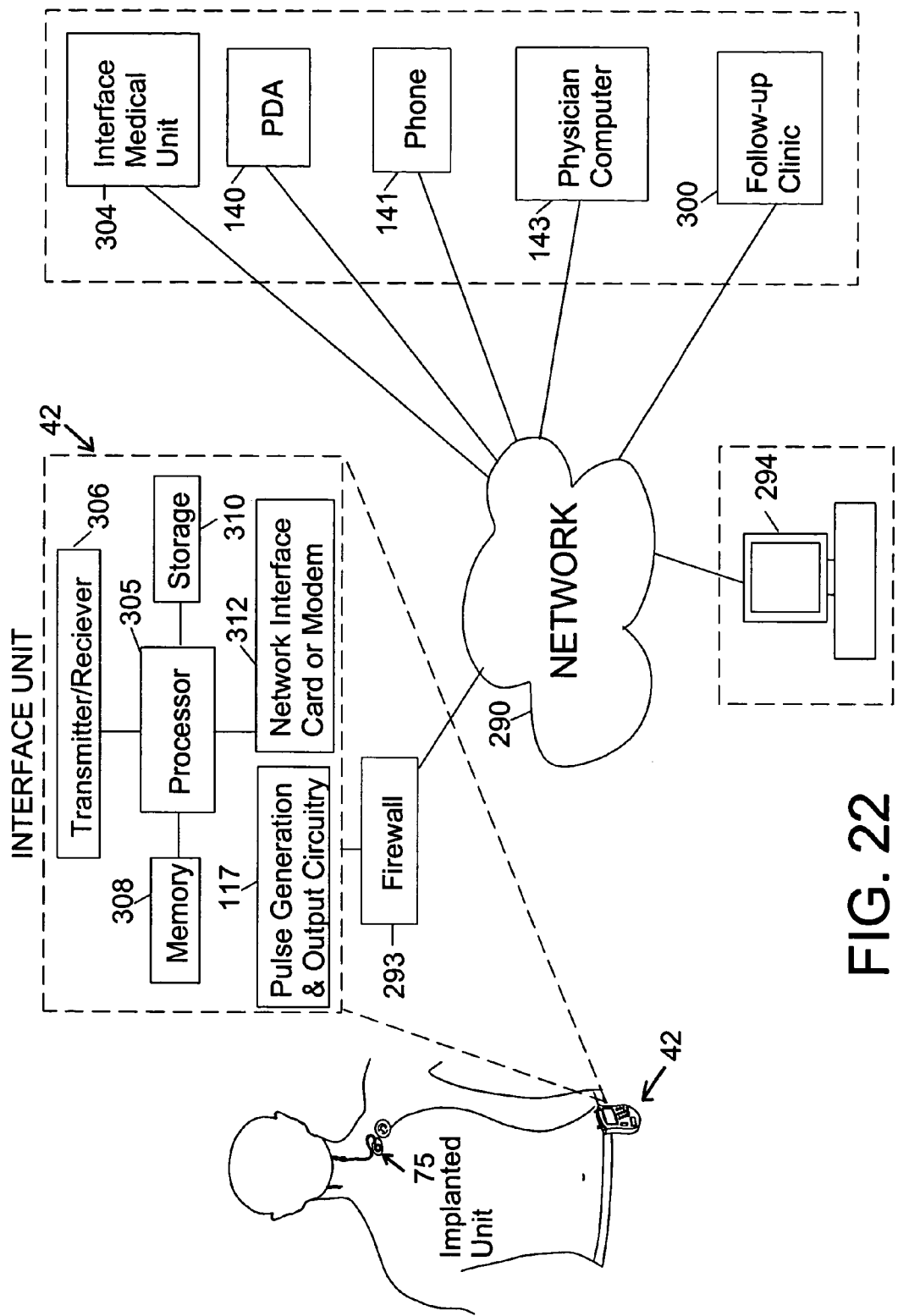
FIG. 22 is a diagram showing networking of various devices with the patient through an interface unit.

The implanted unit 75 communicates with the IU/stim 42 via inductive coupling between a primary coil 46 and secondary coil 48 (FIG. 15). As shown in FIG. 22, the IU/stim 42 and a programmer 85 (not shown) are capable of being networked 290 to other devices such as a remote computer 294, PDA 140, phone 141, physician computer 143. This minimizes situations in which the physical transport of a patient to a particular clinical setting is required.

The standard components of interface unit shown in block 42 are processor 305, storage 310, memory 308, transmitter/receiver 306, and a communication device such as network interface card or modem 312. In the preferred embodiment these components are embedded in the IU/stim 42 and can also be embedded in a programmer. These can be connected to the network 290 through appropriate security measures (Firewall) 293.

Another type of remote unit that may be accessed via central collaborative network 290 is remote computer 294. This remote computer 294 may be used by an appropriate attending physician to instruct or interact with IU/stim 42.

Figure 23A:
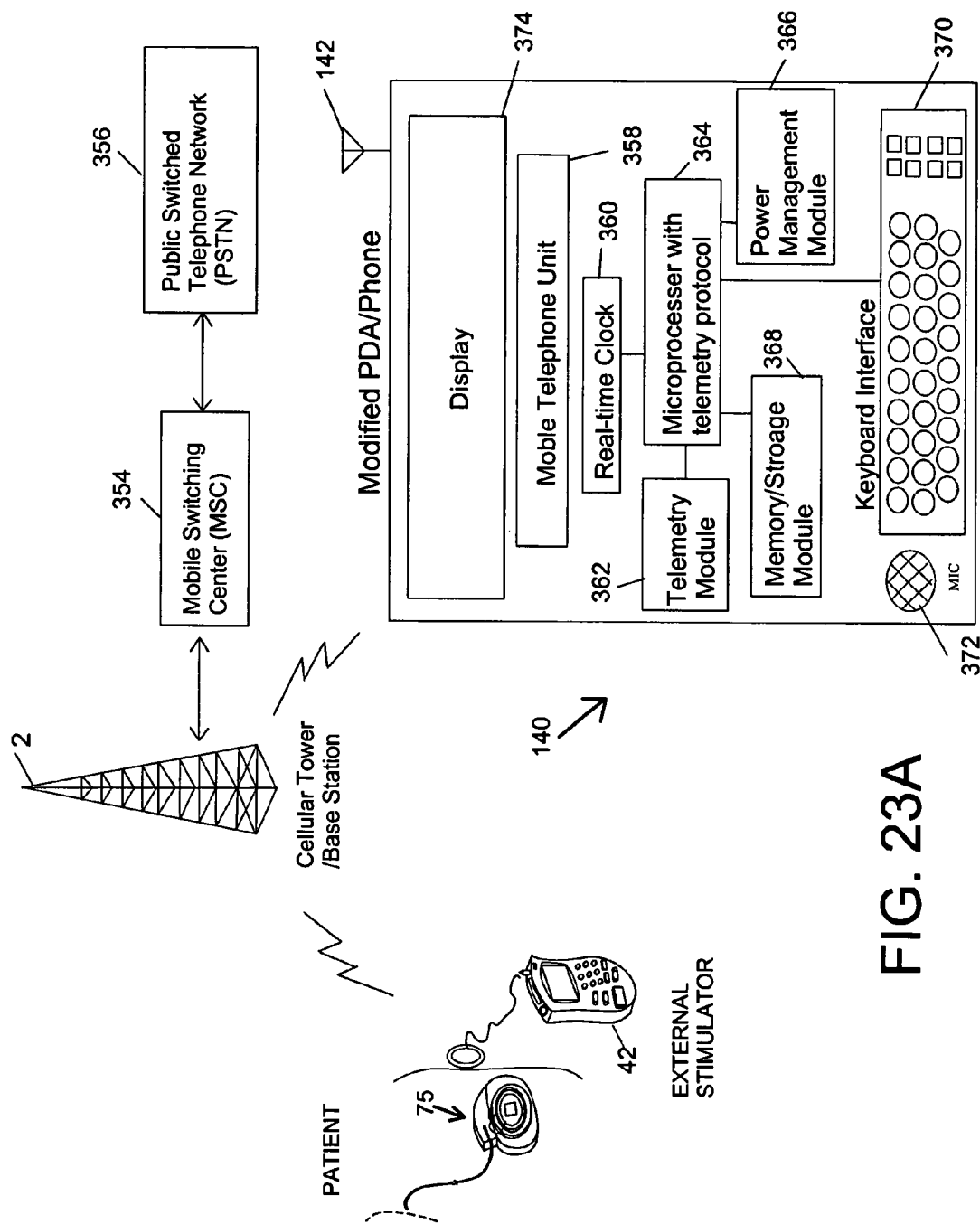
FIGS. 23A and 23B are simplified diagrams showing communication of modified PDA/cell phone with an interface device via a cellular tower/base station.
Figure 23B:
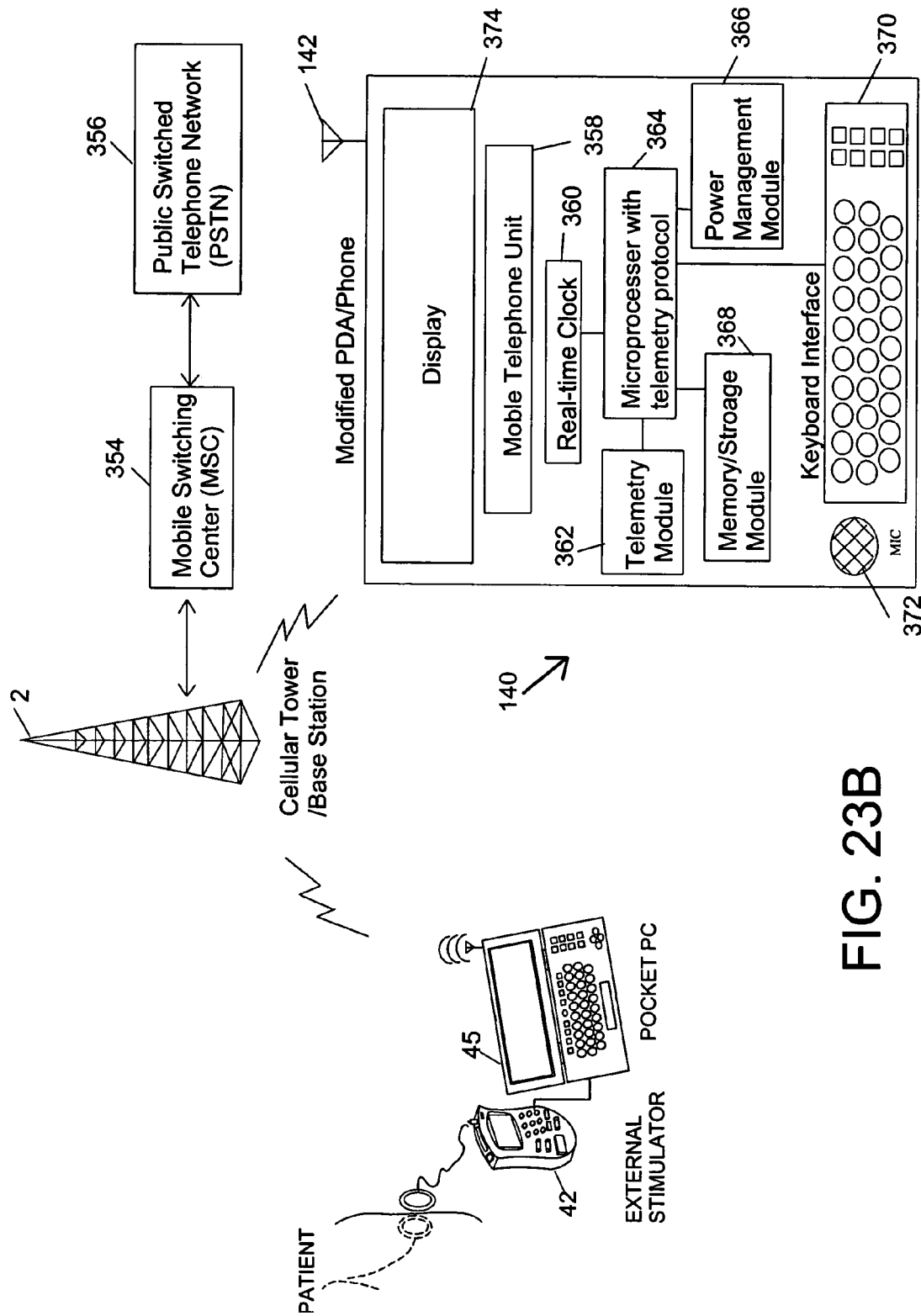

Shown in conjunction with FIGS. 23A and 23B the physician's remote communication's module is a modified PDA/cell phone 140 in this embodiment. The modified PDA/cell phone 140 is a microprocessor-based device as shown in a simplified block diagram in FIGS. 23A and 23B. The modified PDA/cell phone 140 is configured to accept PCM/CIA cards specially configured to fulfill the role of communication module of the present invention. The Modified PDA/Phone 140 may operate under any of the useful software including Microsoft Window's based, Linux, Palm OS, Java OS, SYMBIAN, or the like. The telemetry module 362 comprises an RF telemetry antenna 142 coupled to a telemetry transceiver and antenna driver circuit board which includes a telemetry transmitter and telemetry receiver. The telemetry transmitter and receiver are coupled to control circuitry and registers, operated under the control of microprocessor 364.

With reference to the telecommunications aspects of the invention, the communication and data exchange between modified PDA/cell phone 140 and IU/stim 42 operates on commercially available frequency bands. The 2.4-to-2.4853 GHz bands or 5.15 and 5.825 GHz, are the two unlicensed areas of the spectrum, and set aside for industrial, scientific, and medical (ISM) uses. Most of the technology today including this invention, use either the 2.4 or 5 GHz radio bands and spread-spectrum technology. The three types of spread-spectrum communication used in wireless networks are direct sequence spread spectrum (DSSS), frequency hopping spread spectrum (FHSS), and orthogonal frequency division multiplexing (OFDM). This invention contemplates using all three types of spread-spectrum communications, depending on the patient's circumstances. In an FHSS environment, signals hop among a series of subchannels in a random pattern understood by both transmitter and receiver. Each hop consists of short burst of data, and the amount of time between hops is referred to as dwell time. Although DSSS also spreads transmissions over multiple channels with a given frequency range, no hopping occurs between frequencies. Instead, a binary string called a spreading code creates redundant transmissions, increasing the chances that signals and data will reach the intended receiver intact. The sending wireless device must use the same spreading code as the sender for signals to pass between them. Restricting the devices to a particular code, rather than using several, reduces the interference potential on the channel used by the two devices. OFDM makes efficient use of available spectrum by dividing it into subchannels and sending a portion of a given data transmission over each one.

The telecommunications technology, especially the wireless Internet technology, which this invention utilizes, is constantly improving and evolving at a rapid pace, due to advances in RF and chip technology as well as software development. Therefore, one of the intents of this invention is to utilize "state of the art" technology available for data communication between Modified PDA/Phone 140 and IU/stim 42.

In the United states, the CDMA technology that is available today (2.5G) will go through a series of CDMA upgrades. The 2.5G version is called cdma20001× while the 3G version is called cdma20003×. Each of these represents an increase or improvement in signal processing, bandwidth, and/or modulation. In Europe a path to 3G consists of several intermediate steps. The first of these intermediate steps (2.5G) is General Packet Radio Services or GPRS, which overlays packet switching on the existing GSM system. The next intermediate step is the Enhanced Data GSM Environment or EDGE. Among other things, EDGE incorporates a modulation improvement to GPRS. From there the official "3G" system for Europe is Universal Mobile Telecommunications System or UMTS, which is a true packet switched network. In Japan, the first two generation pretty much worked in isolation with their 1G analog system (JTACS) and their 2G digital system (PDC based on a TDMA air interface ). Because of all this uniformity, it was possible for Japan to essentially jump over 2.5G and go right to a 3G system. In Japan, which is the first country to deploy a system with 3G capabilities, the system is based on a WCDMA air interface similar to that in UTMS.

For the system of the current invention, the use of any of the "3G" technologies for communication for the Modified PDA/Phone 140, is considered within the scope of the invention. Further, it will be evident to one of ordinary skill in the art, that as future 4G systems, which will include new technologies such as improved modulation and smart antennas, can be easily incorporated into the system and method of current invention, and are also considered within the scope of the invention.

Shown in conjunction with FIGS. 23A, 23B, the modified PDA/cell phone 140 is a microprocessor-based device. Attached to the microprocessor 364 are a number of peripheral devices such as the touch screen, IR port, speaker, memory modules etc, as is well known to one skilled in the art.

Figure 24A:
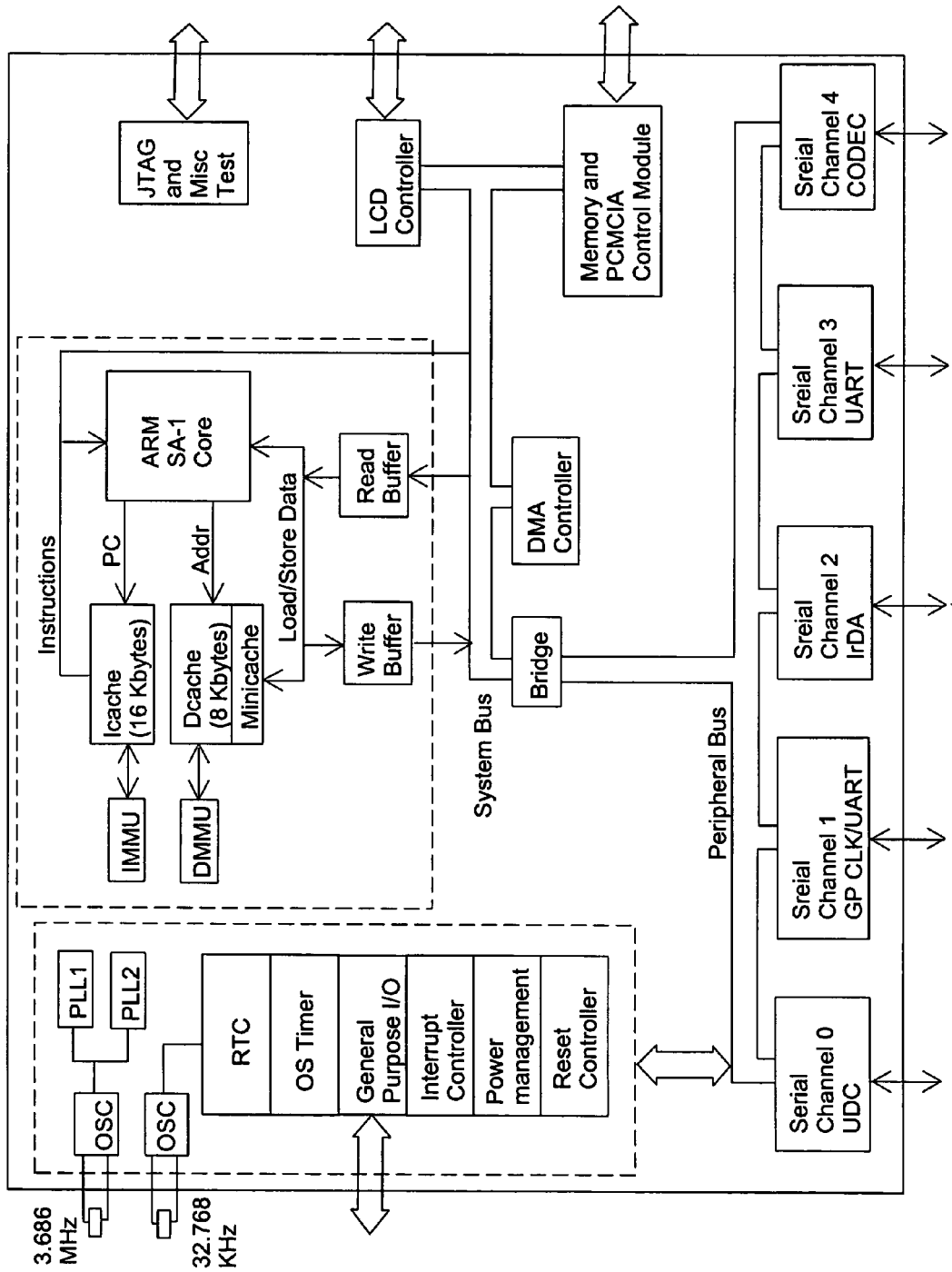
FIG. 24A is a block diagram of an Intel strongARM processor.

One preferred embodiment uses the Intel StrongARM PDA microprocessor, however, another popular PDA microprocessor, the Motorolla DragonBall may also be used. A block diagram of the Intel StrongARM microprocessor is shown in FIG. 24A. The Intel microprocessor is typically used in devices running Windows CE, and the Motorola is used with devices running the Palm OS operating system. The ARM microprocessor core has a very well accepted architecture and numerous key semiconductor and system partners.

Shown in conjunction with FIG. 24A, the StrongARM has five serial channels used to communicate with peripheral devices.

Channel 0: User datagram protocol (UDP) is a connectionless protocol that, like transmission control protocol (TCP), runs on top of Internet protocol (IP) networks. Unlike TCP/IP, UDP/IP provides very few error recovery services, offering instead a direct way to send and receive datagrams over an IP network. It is used primarily for broadcasting messages over a network. A datagram is a piece of a message transmitted over a packet-switching network, and is a packet of information that contains the destination address in addition to data.

Channel 1: GPCLK/UART—This channel can be used as a general purpose clock (GPCLK) or universal asynchronous receiver-transmitter (UART).

Channel 2: Infrared Data Association (IrDA) is a group of device manufacturers that developed a standard for transmitting data via IR light waves. IrDA ports support roughly the same transmission rates as traditional parallel ports. The only restrictions on their use are that the two devices must be within a few feet of each other, and there must be a clear line of sight between them.

Figure 24B:
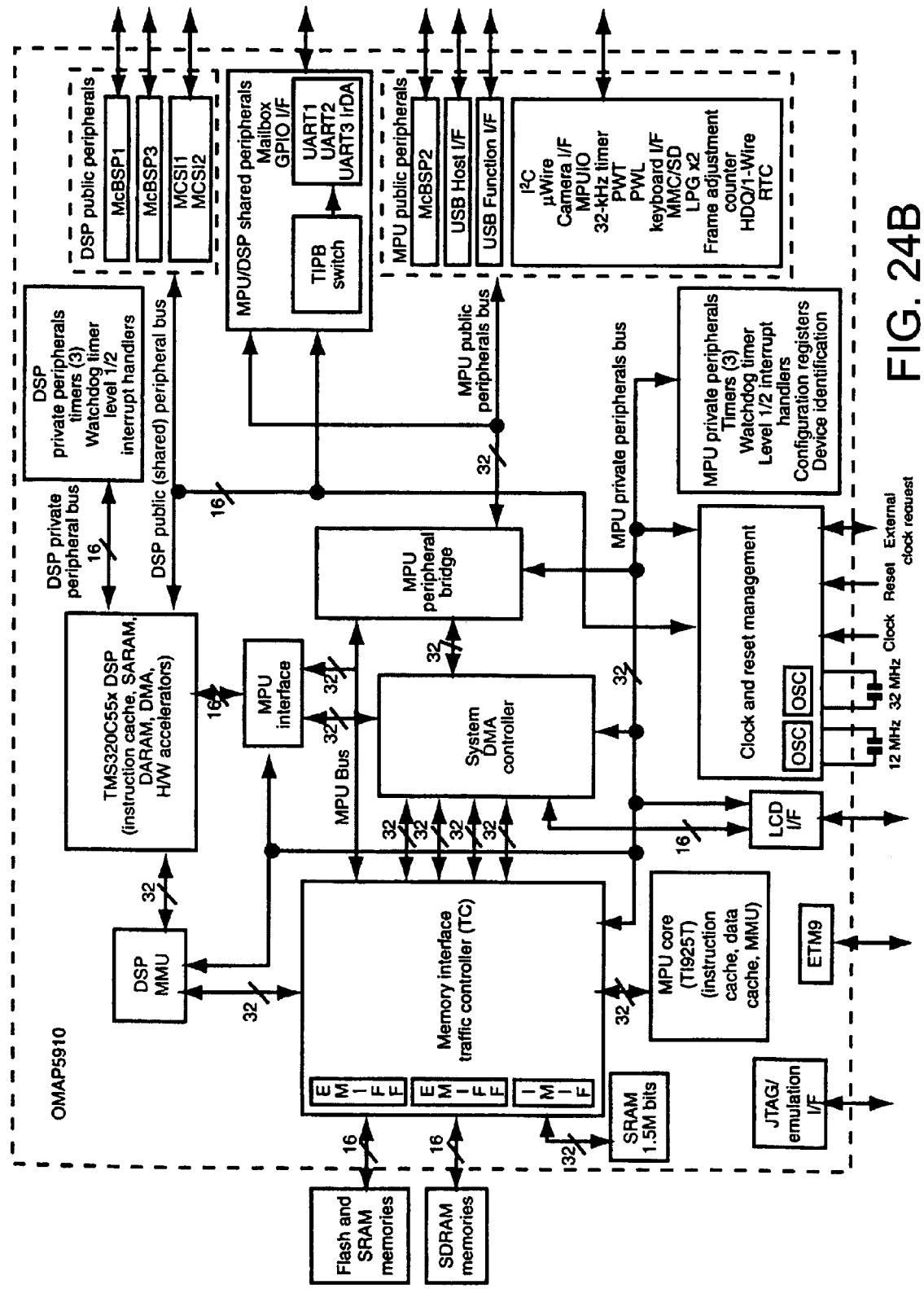
FIG. 24B is a block diagram of an extensively integrated OMAP chip.

Channel 3: Universal asynchronous receiver-transmitter (UART):

Example of another microprocessor that may be used is OMAP processor from Texas Instruments. It is an enhanced ARM-based processor, and FIG. 24B shows a block diagram of this extensively integrated OMAP microchip. ARM-based microprocessors can also be used in Palm OS devices. The OMAP processor includes, TI-enhanced ARM9 up to 175 MHz TMS 320C55×DSP up to 200 MHz Optimized software architecture that allows designers to leverage dual processing, and provides a complete and seamless software foundation.

DSP/BIOS Bridge that provides a seamless interface to the DSP using standard APIs allowing easy access to DSP multimedia algorithms.

Open platform that enables a large network of independent developers to provide a broad range of OMAP compatible software solutions.

MMC-SD support

Blutooth interface, and

Small, 289-pin MicroStar BGA package eases design in space-constrained devices.

Figure 25:
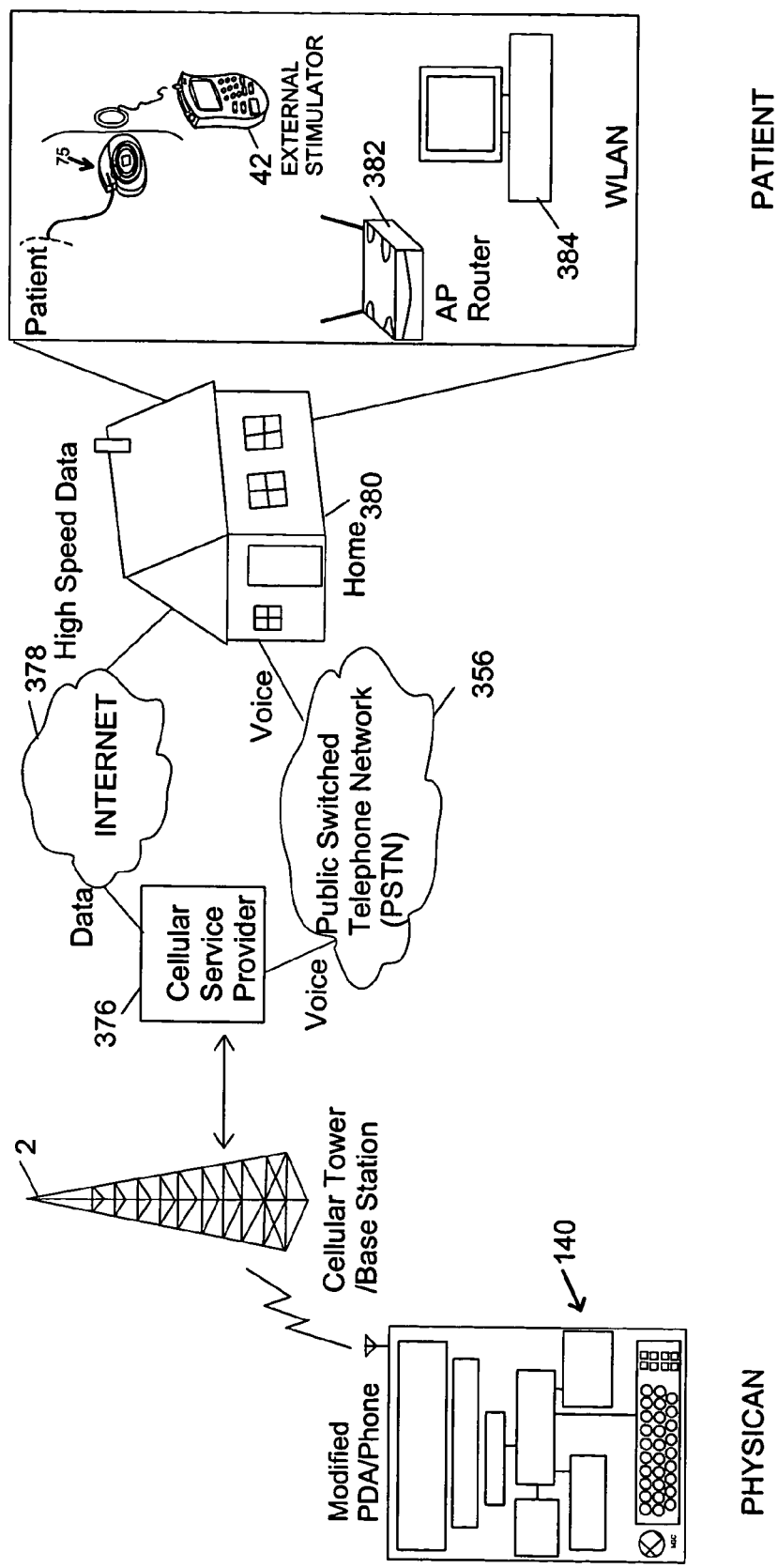
FIG. 25 depicts wireless communication of an interface unit with modified PDA/cell phone via an access point (AP) router.

One aspect of the invention also takes advantage of wireless networking, specifically the WLAN connection as defined by the IEEE 802.11 standard. The WLANs currently operate on the 2.4 GHz and 5.2-5.8 GHz frequency bands. For example as shown in FIG. 25, a wireless Access Point (AP) is set up in patient's home which already has a High Speed Data Connection, either via cable modem, high speed telephone line, or satellite based connection. When the patient is in his/her home, within the communication range of the AP Router 382, High Speed data communication via the Internet occurs with the IU/stim 42. Typically the operating distances are in the order of 300 to 1,500 feet, but can be extended by the use of high-gain antennas and amplifiers to more than 10 miles. Since the WLAN connections are in the order of 11 to 54 Mbps or higher, the speed of data exchange will be limited by the speed of the Internet connection.

Figure 26:
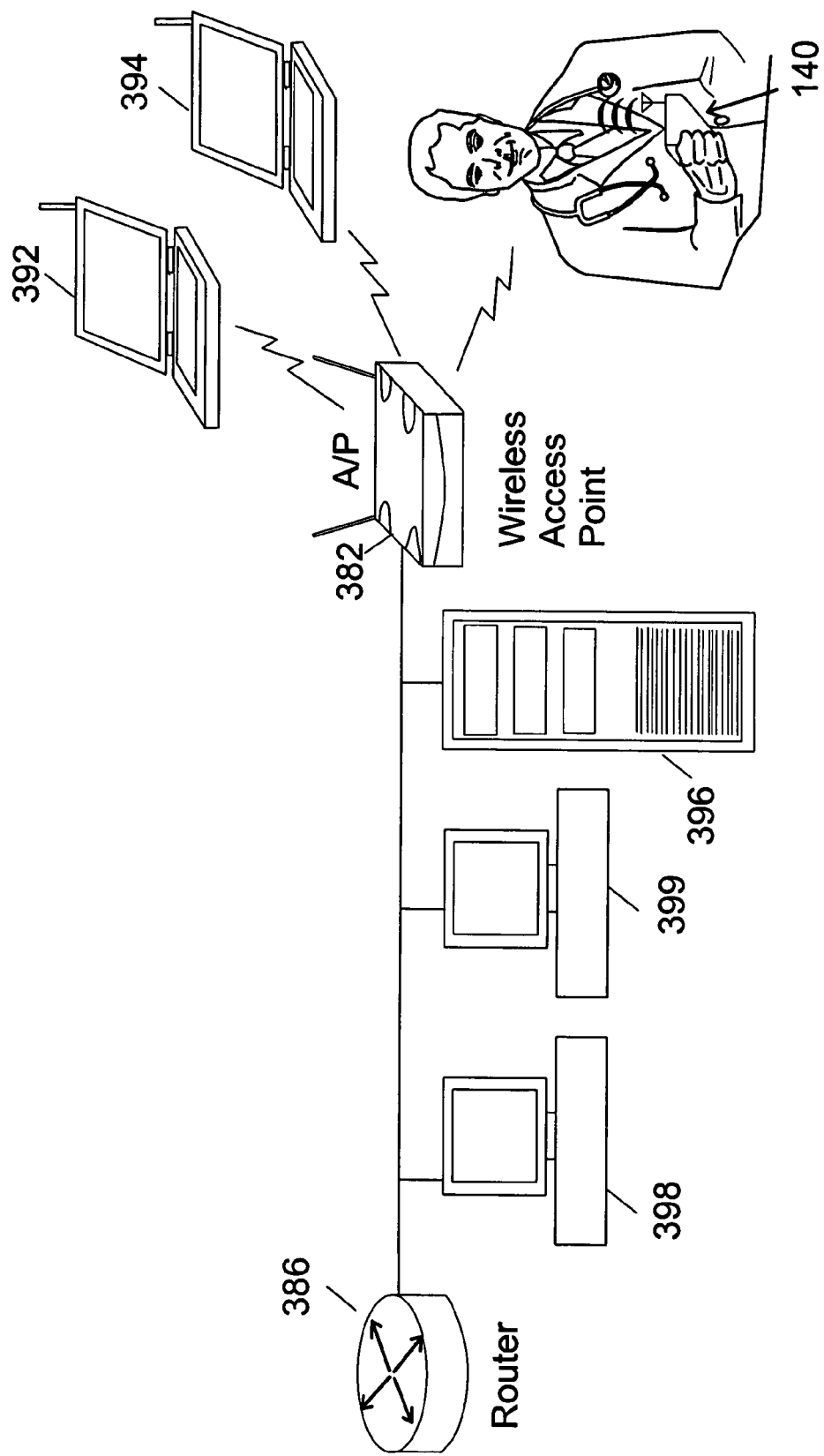
FIG. 26 shows a physician communicating and exchanging data with a modified PDNphone using wireless access point.

Similarly, a physician using the Modified PDA/Phone 140 may gain access to the high speed wireless Internet by being within the communication distance of an AP 382, whether in the office or any other place where an AP is available. FIG. 26 shows a configuration of a physician or physician group where a modified PDA/cell phone 140 or other wireless computers gain access to high speed Internet using an access point 382.

Figure 27:
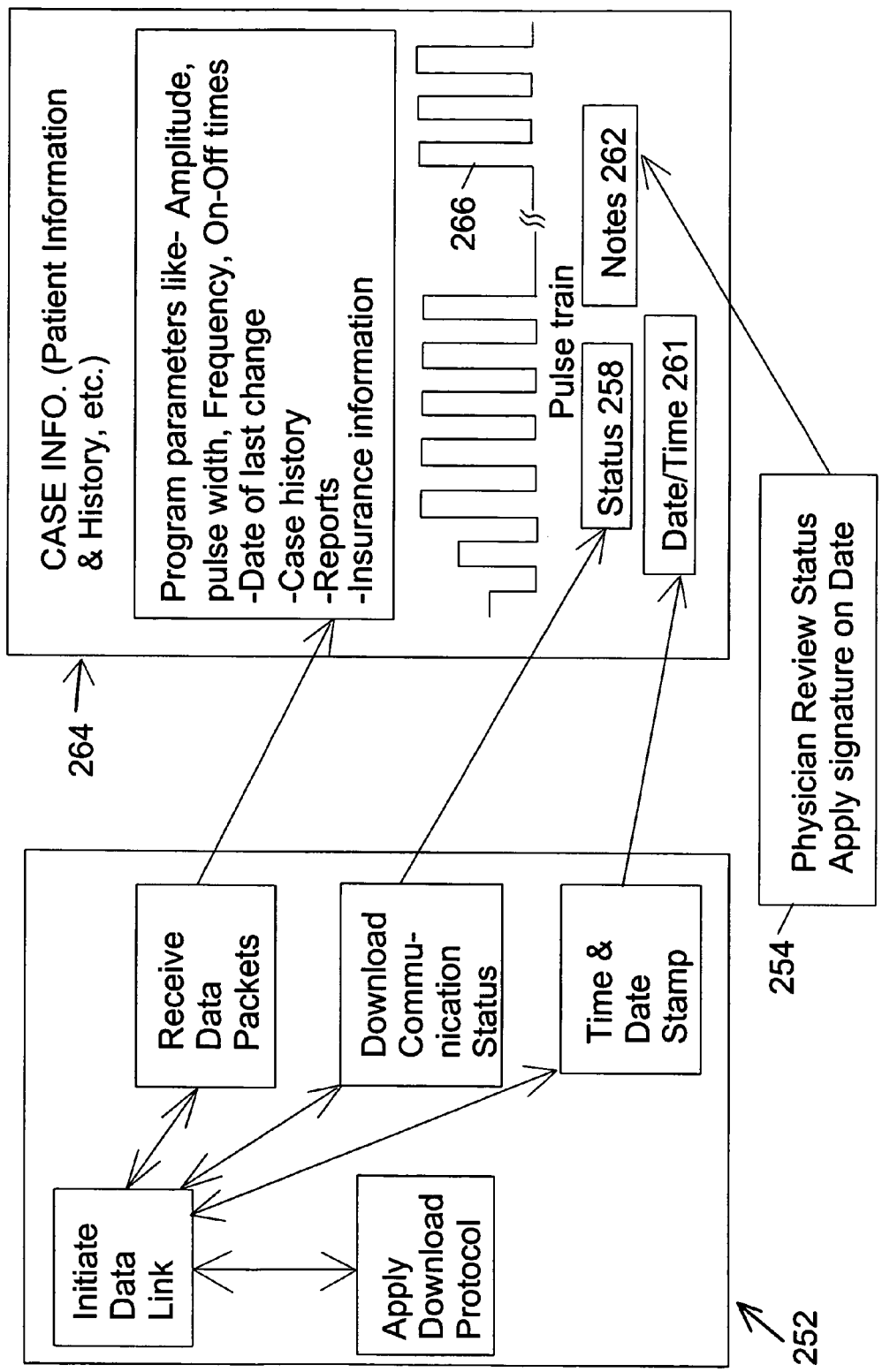
FIG. 27 is a diagram which shows the information available on a web-page at the server or mobile device.

FIG. 27 shows visualization process of the data received on the modified PDA/cell phone 140 from the IU/stim 42. This data is also available on a server at the office. The Web pages 264, either on the modified PDA/cell phone 140 or on the server provide ability of the health care provider, with proper authorization, to select new pulse generation programs or edit existing ones. The parameters of an existing program can be edited, and a schedule can be prepared for application to the pulse generator of a particular patient. The parameters such as, program number, amplitude, pulsewidth and frequency etc. are maintained and modified. A graphical plot of the pulse signal can also be visualized as an optional plot 266. The appropriate individual, such as the physician, can review the above information 264 and examine status 258, 260 make changes, apply notes and his/her signature 262 to the patient record.

In addition to interrogating and programming the implantable stimulator 75 via an IU/stim 42 via a modified PDA/cell phone 140, a physician 5 may also access and manipulate patient's clinical and billing information on the modified PDA/cell phone 140. This is shown in conjunction with FIGS. 28 and 29. In the presently preferred embodiment, the software utilized is based on Microsoft Windows platform and Palm OS platform. Other computer operating environment such as LINUX, UNIX, MAC, Java OS or SYMBIAN may be used and is considered within the scope of the invention.

Figure 28:
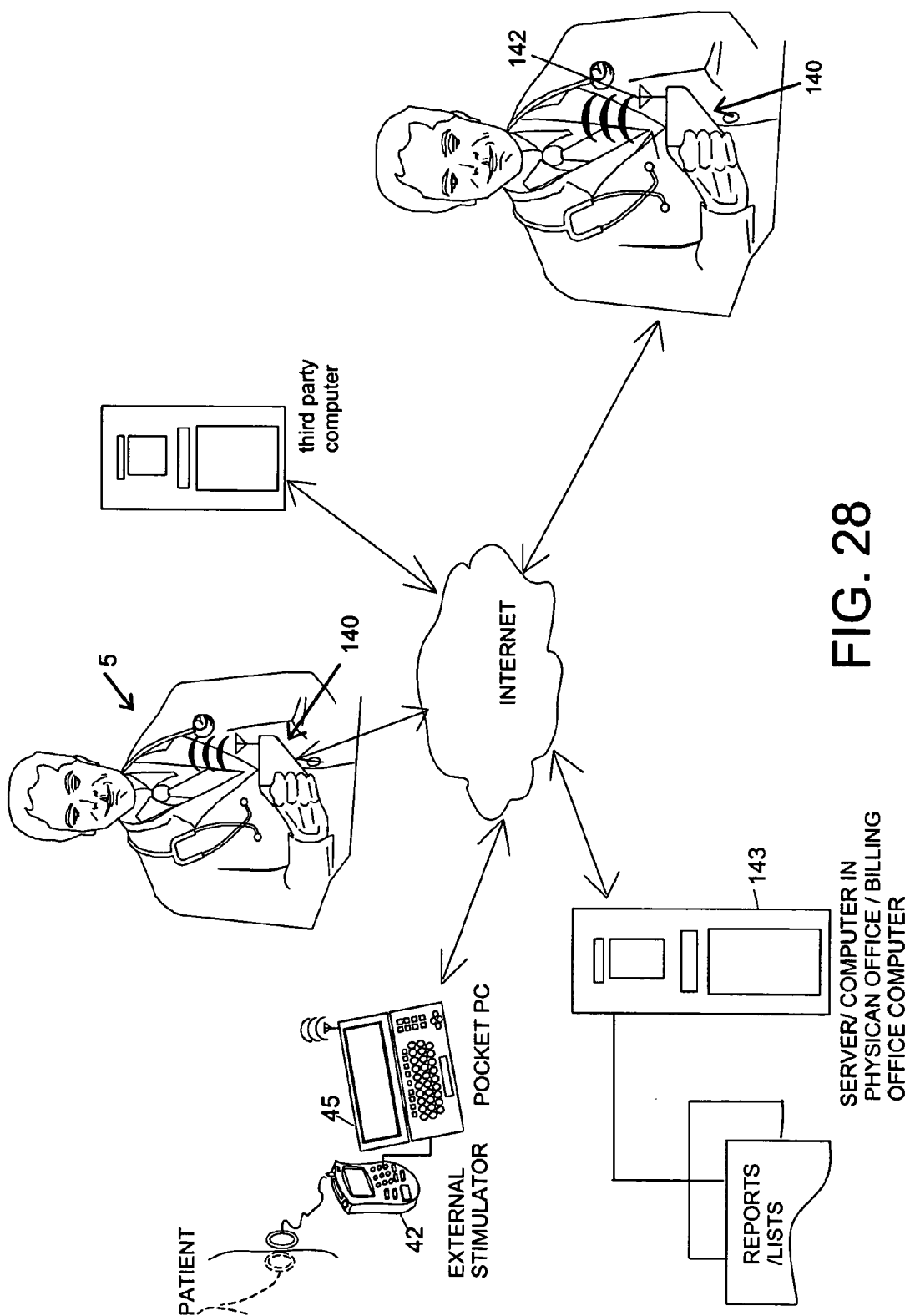
FIG. 28 depicts networking of the modified PDA/cell phone with third party computer, billing office computer, and patient.

For the billing and patient management aspect of the invention, shown in conjunction with FIG. 28, a physician 5 connects to Internet utilizing his/her modified PDA/cell phone 140 and password. The physician 5 may review patient's medical information as stored in the modified PDA/cell phone 140, or from the server 130 in physician's office via the Internet. Based on patient's device interrogation, and review of patient's clinical information, the physician 5 may re-program the device over the Internet. Upon verification of programming the physician 5 may enter the invoicing information on the modified PDA/cell phone 140 and may send to sever in the office over the Internet.

The modified PDA/cell phone 140 has the capabilities and software to make remotely available, patient data and information necessary to make an informed patient decision. For example, the physician can connect to the office computer to obtain patient history and nerve stimulation parameter information via server over wireless Internet before remotely making changes to patient's stimulation schedules. Furthermore, the physician can edit the information and data downloaded to the modified PDA/cell phone 140 for changes and updates, and add additional information before storing it on modified PDA/cell phone 140 or sending it to the server 130, or office computer.

Figure 29:
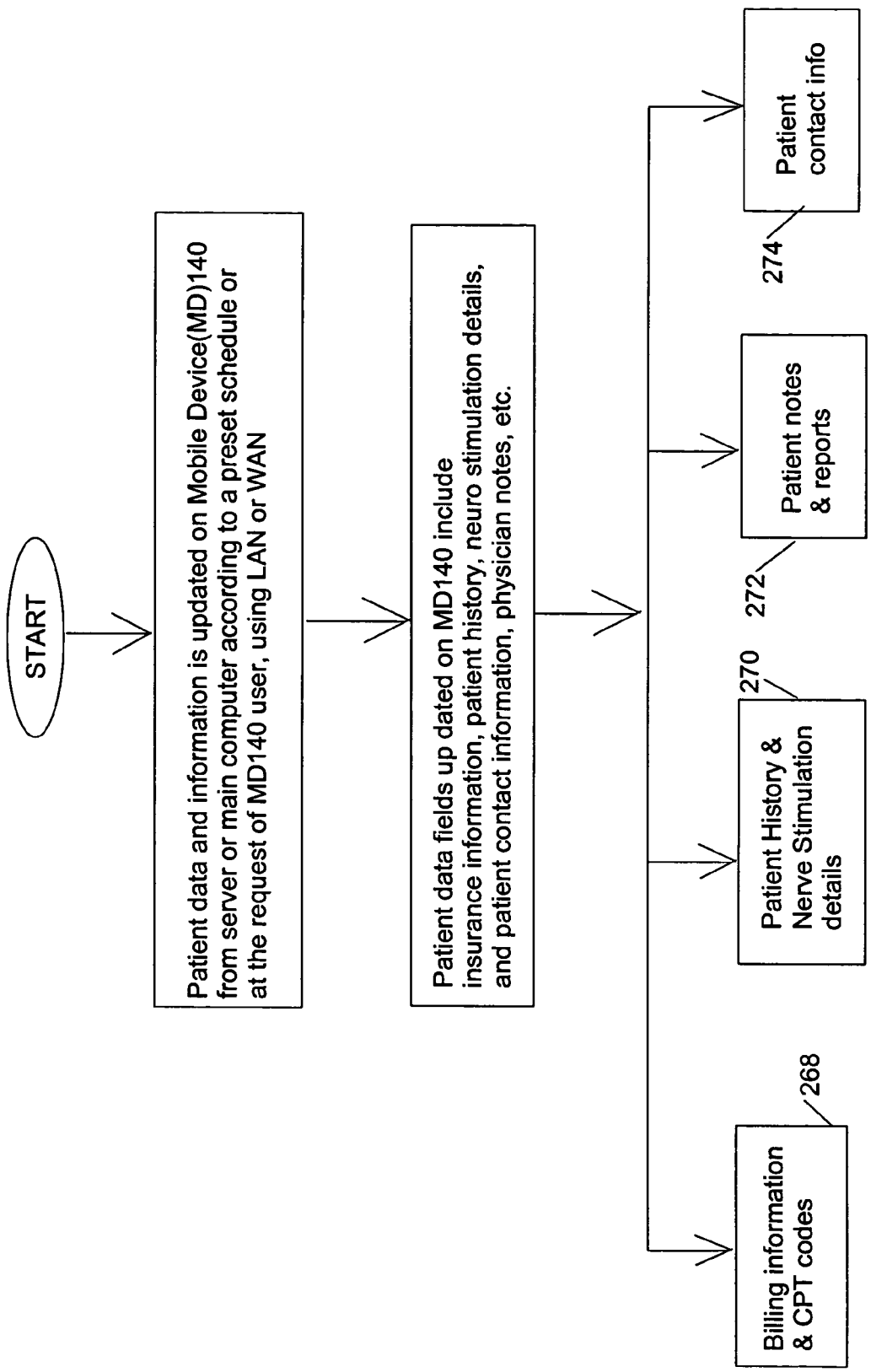
FIG. 29 is a block diagram illustrating type of information available to the physician on a modified PDA/cell phone.

Shown in conjunction with FIG. 29, when a physician is logged-on to the Internet, with the appropriate connections a physician can do any of the following things: a) retrieve patient data and information from the office computer, b) interrogate and make programming changes to the patients stimulation parameters, c) communicate with third party, d) do patient billing/invoicing and send bills to paying party, and e) update patient information or write reports on the server via the network connection.

The modified PDA/cell phone 140 software is programmed to receive updated information on relevant and necessary patient history, nerve stimulation program parameter details, patient contact information and patient billing information. Patient's relevant data can be retrieved from the data maintained on the server, office computer, or another third party source, with the appropriate password. Furthermore, the modified PDA/cell phone 140 has capabilities to allow the physician to make patient notes, write patient reports and complete patient billing.

Figure 30:
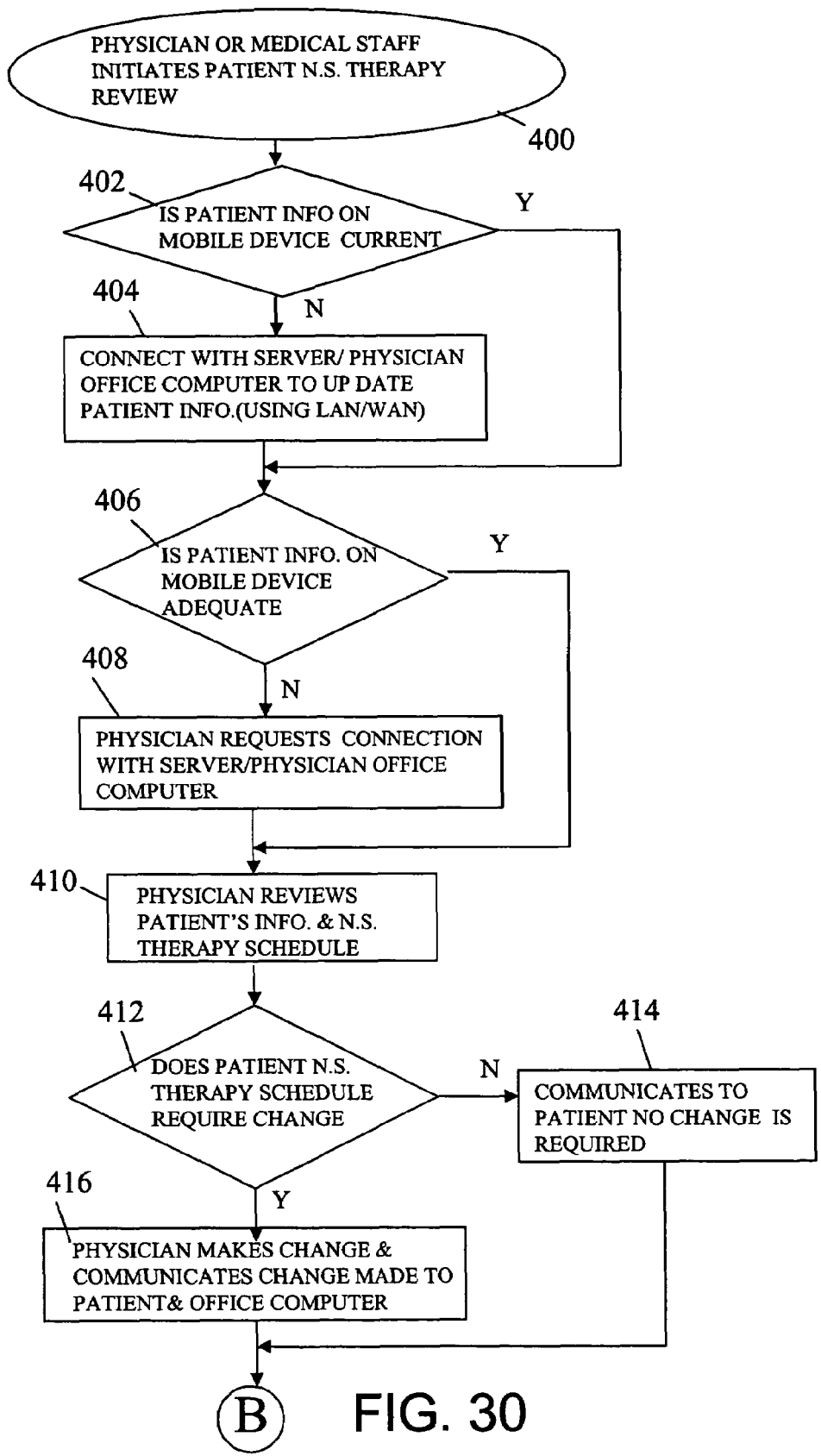
FIG. 30 is a flow diagram for physician initiated nerve stimulation therapy review.

The remote interrogation and programming of the IU/stim 42 may be initiated at the request of the patient 32 or may be initiated by the physician 5 as shown in step 400 of FIG. 30. The physician's checking up on the patient and the device, may be a scheduled activity or be triggered by an event. The physician 5 or medical personnel may look at the patient's history and IU/stim 42, device history either on the modified PDA/cell phone 140 if available, or by connecting to the office computer as shown in steps 402-410. Once the information is reviewed, the physician decides if the active stimulation parameters of the IU/stim 42 need to be altered (step 412). If required, the changes are made and recorded in the office computer records. This information is also communicated to the patient, steps 414 and 416.

In one aspect of the invention the modified PDA/cell phone 140 software has a limited number of current procedural terminology (CPT) codes for diagnosis and procedures. These limited number of codes are stored in the modified PDA/cell phone 140, and can range from one to several hundred. The CPT codes are initially loaded (or entered) into the modified PDA/cell phone 140, and the software is customized and configured, such that one single command brings up one procedure or diagnosis code or a group of procedure codes. The codes entered in the modified PDA/cell phone 140 will of course differ according to the specialty of the physician. The physician can also add/delete codes into the modified PDA/cell phone 140. Additionally some codes can be automatically activated after a procedure is performed and a bill is generated which can be sent to the physician's office or sent to third party for payment. For example, after the physician reviews a patient nerve stimulation schedule remotely, an automatic bill is generated on the server and either sent to physician's office for further action or sent to third party computers. Additionally, the modified PDA/cell phone 140 keeps a log and notes of all patient seen and patients nerve stimulation schedules reviewed during the day.

Figure 32:
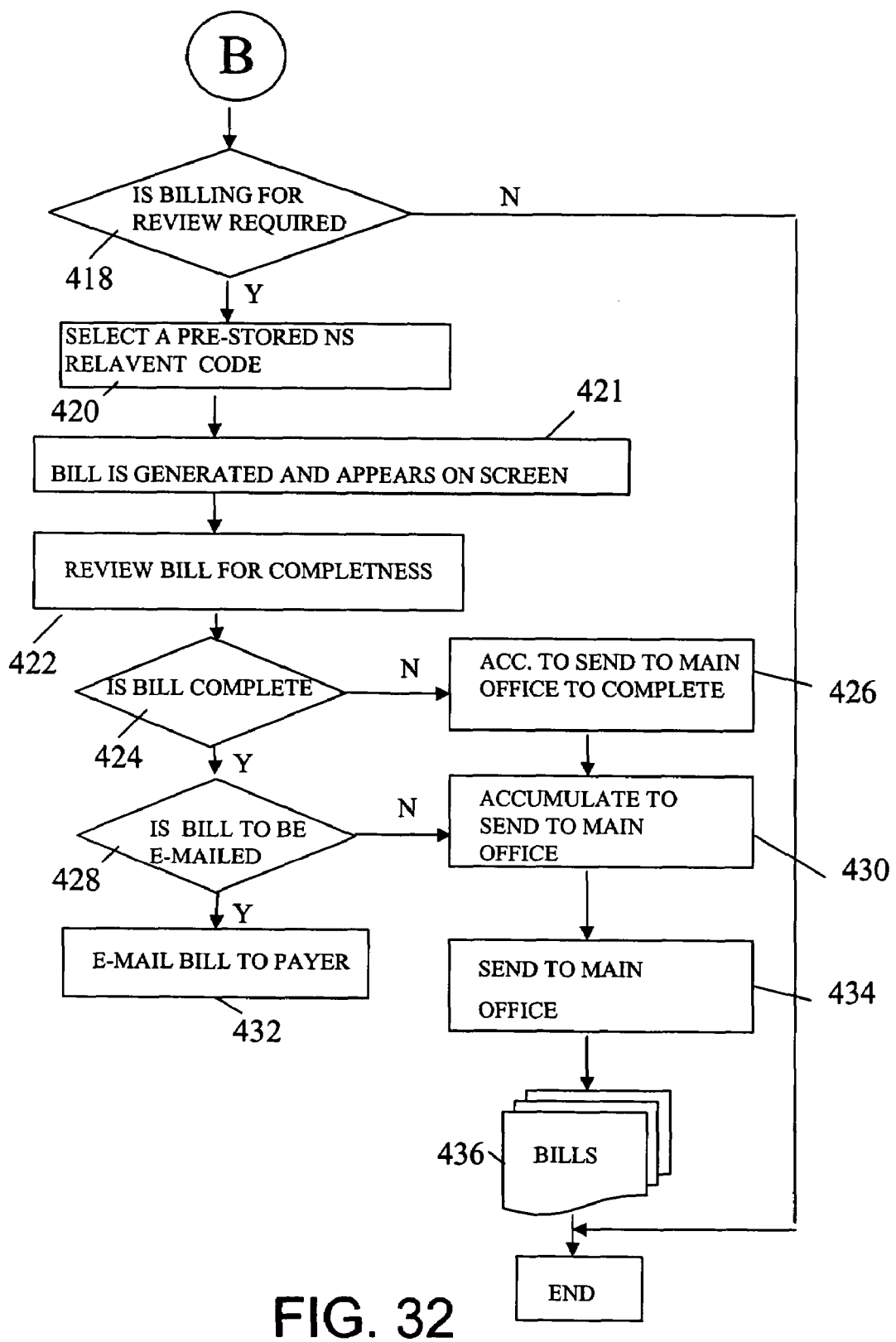
FIG. 32 is a flow diagram for billing, using the modified PDA/cell phone.

As shown in conjunction with FIG. 32, the physician determines if billing for the session is required, step 418. In case billing is required, the modified PDA/cell phone 140 has stored in its memory, all the selected subset of appropriate billing codes and templates. Once the generated bill appears on the screen as shown in step 421, the physician reviews the bill for completeness, step 422. If the bill is complete, it may be e-mailed to payer as shown in step 432, or alternatively sent to main computer 436 for billing department to handle.

Figure 31:
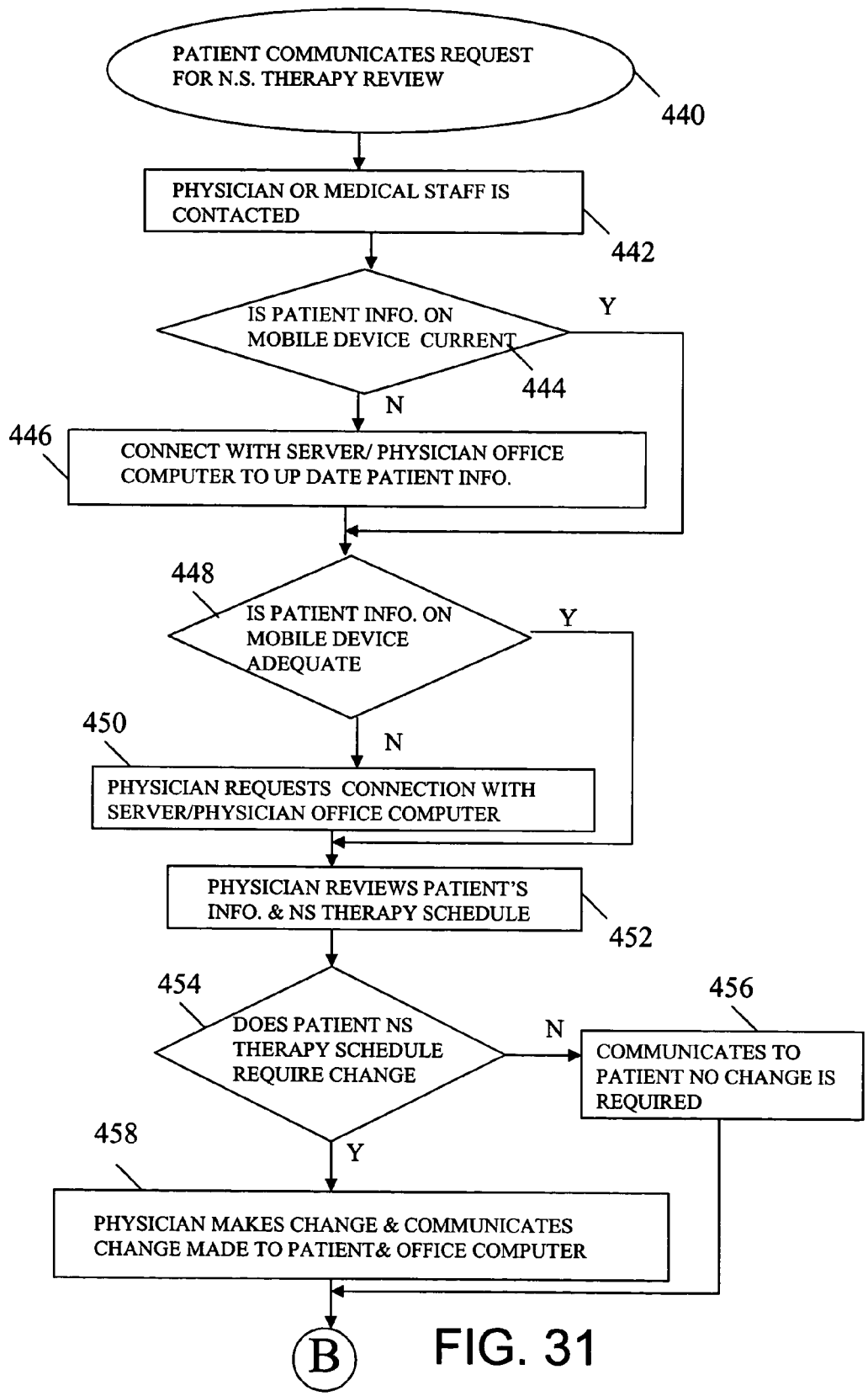
FIG. 31 is a flow diagram for patient initiated nerve stimulation therapy review.

When a patient initiates request for therapy review as in step 440, shown in conjunction with FIG. 31, the physician or medical staff is contacted 442. The physician again looks to see if the patient information on the Modified PDA/Phone 140 is current, if not, then retrieves it from the server in physician's office 446. Then in a series of steps, similar to as described earlier, the physician reviews records, makes changes to the program if needed, contacts patient, and bills for the services if required, as shown in steps 444-458 and steps 418-436.

The physician can also write or dictate through voice recognition, a patient report on the modified PDA/cell phone 140 and send it to his/her office of third party. Alternatively, the modified PDA/cell phone 140 can be programmed to have a report template screen wherein the physician can enter the variable fields like diagnosis or results or findings in order to complete the report.

Figure 33:
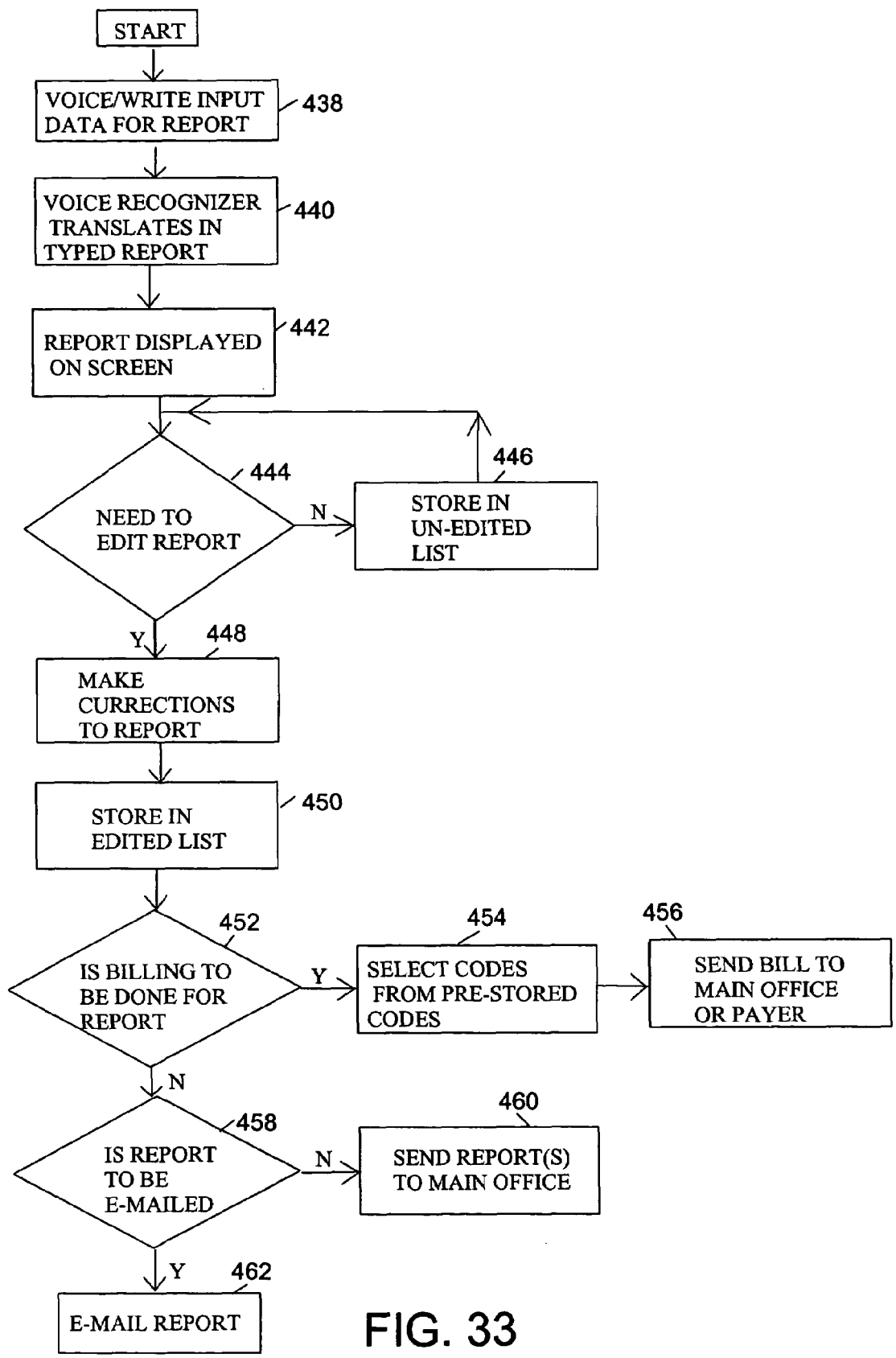
FIG. 33 is a flow diagram for writing a report on the modified PDA/cell phone.

Shown in conjunction with FIG. 33, after a patient record has been reviewed a report screen automatically appears asking if a report is to be written. The physician 5 can write/dictate by using voice recognition software on the modified PDA/cell phone 140. Alternately a pre-packaged template is stored in the modified PDA/cell phone 140 memory where only the variable fields need to be entered, like diagnosis, findings, or results to complete the report and can be e-mailed to the server, or office computer, or third party, or may be accumulated for downloading later, shown in steps 438-462.

Figure 34:
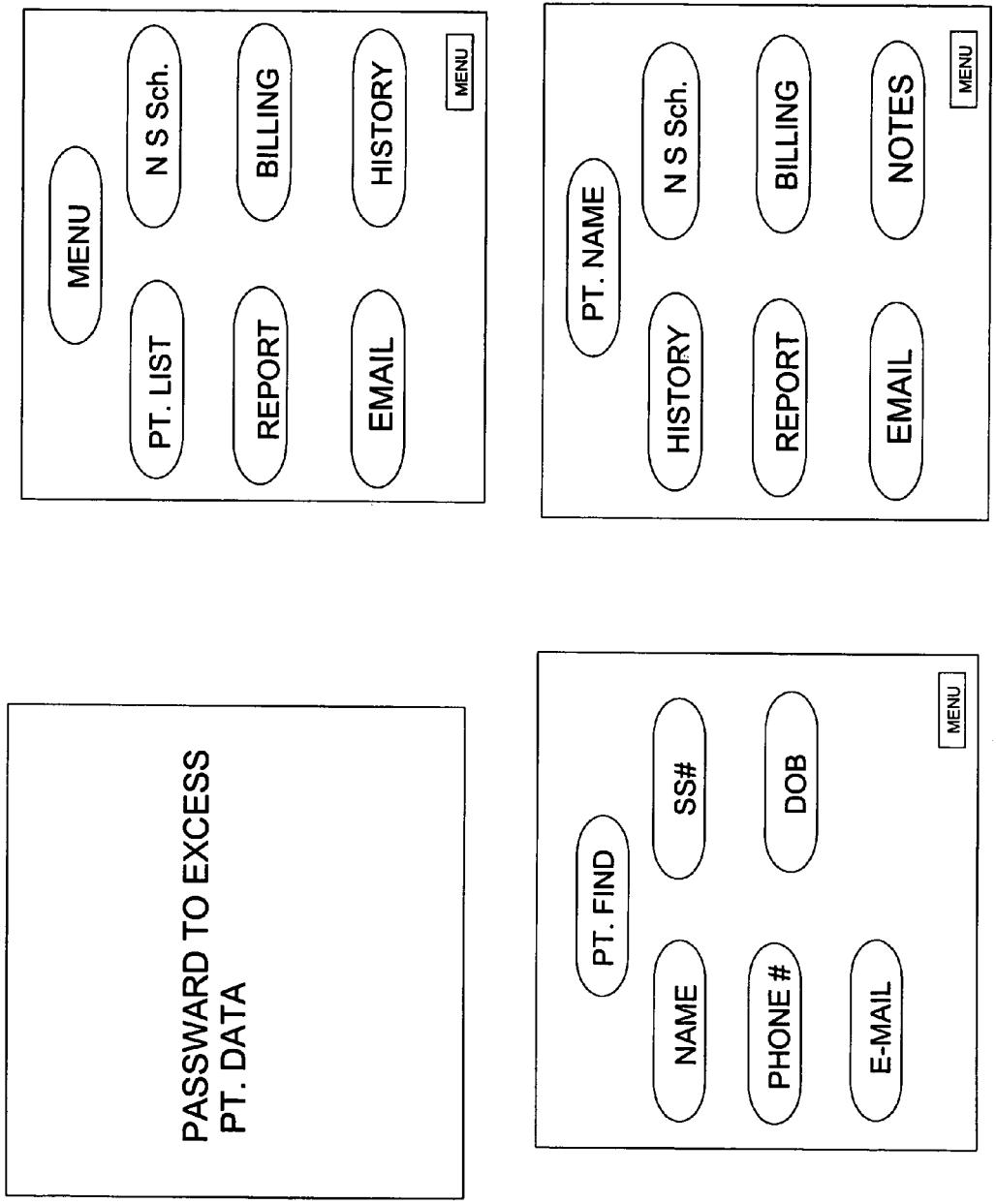
Figure 35:
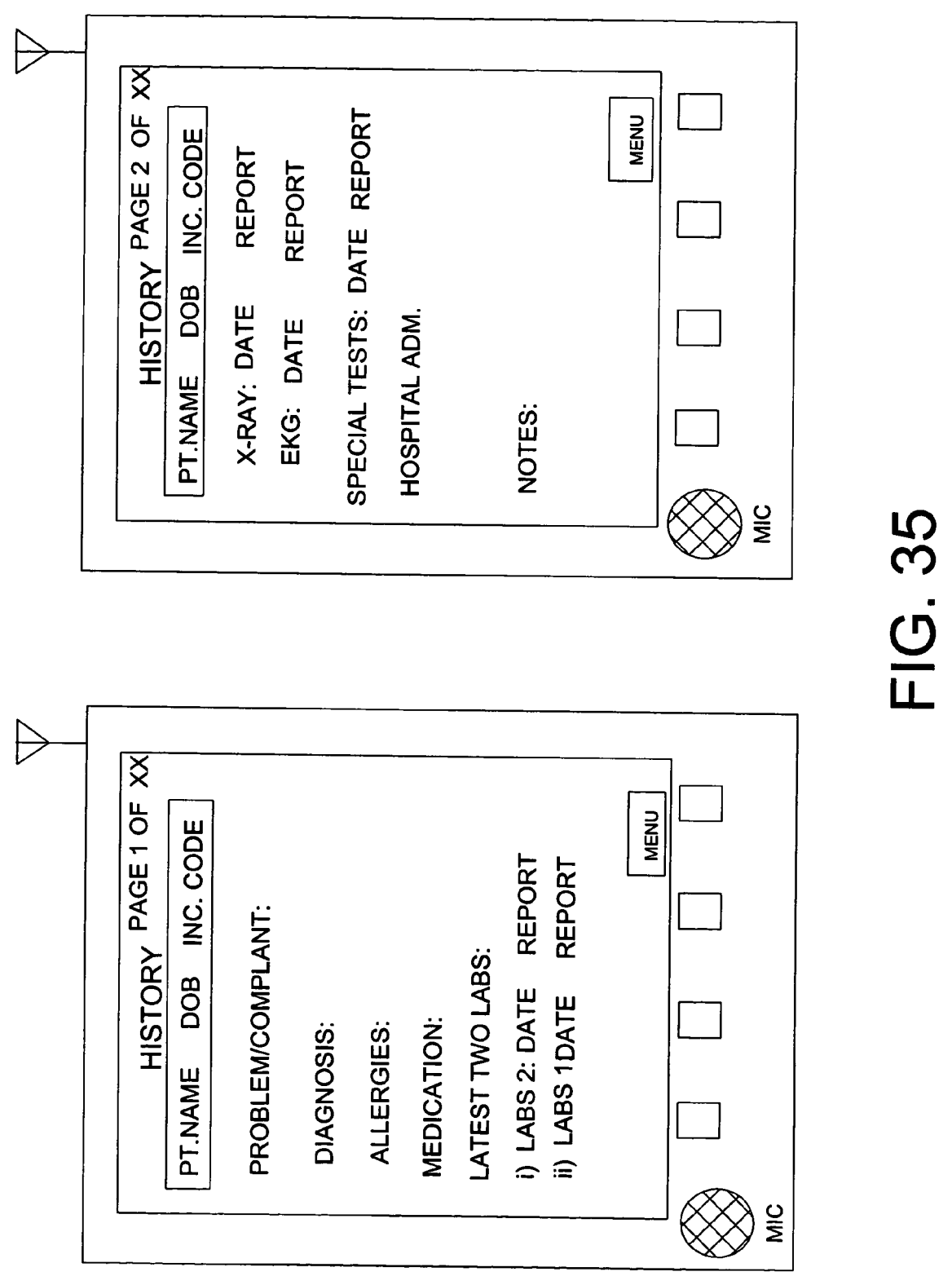

FIG. 34 shows examples of top level menus for patient management screens that appear on the modified PDA/cell phone 140. FIG. 35 show examples of the patient history screens appear on the modified PDA/cell phone 140 comprising patient history, information, complaint, diagnosis, allergies, medication, lab test dates and reports, x-ray dates and report, EKG dates and report, special test dates and report, hospital admission, and the like.

It will be clear to one skilled in the art, that many different embodiments of this invention are possible. For example, the communication link can be configured to be set up such that, a server located in a group's office may communicate and exchange data with IU/stim 42. In this scenario, the modified PDA/cell phone 140 links to the server, and updates and exchanges data through the server. The server initiates an upload of the actual parameters being applied to the patient, receives these from the IU/stim 42, and stores these in its memory, accessible to the authorized user as a dedicated content driven web page. The web page is managed with adequate security and password protection. The physician or authorized user can make alterations to the actual parameters, as available on the server, and then initiate a communication session with the IU/stim 42 to download these parameters.

The physician is also able to set up long-term schedules of stimulation therapy for their patient population, through wireless communication with the server. The server in turn communicates these programs to the neurostimulator via IU/stim 42. For instance, a physician may program an Alzheimer's patient to a stimulation program for two weeks, and program an epilepsy patient to a selected long-term "on", "off" stimulation therapy. Each schedule is securely maintained on the server, and is editable by the physician and can get uploaded to the patient's stimulator device at a scheduled time. Thus, therapy can be customized for each individual patient. Each device issued to a patient has a unique identification key in order to guarantee secure communication between the wireless server 130 and IU/stim 42.

Figure 36:
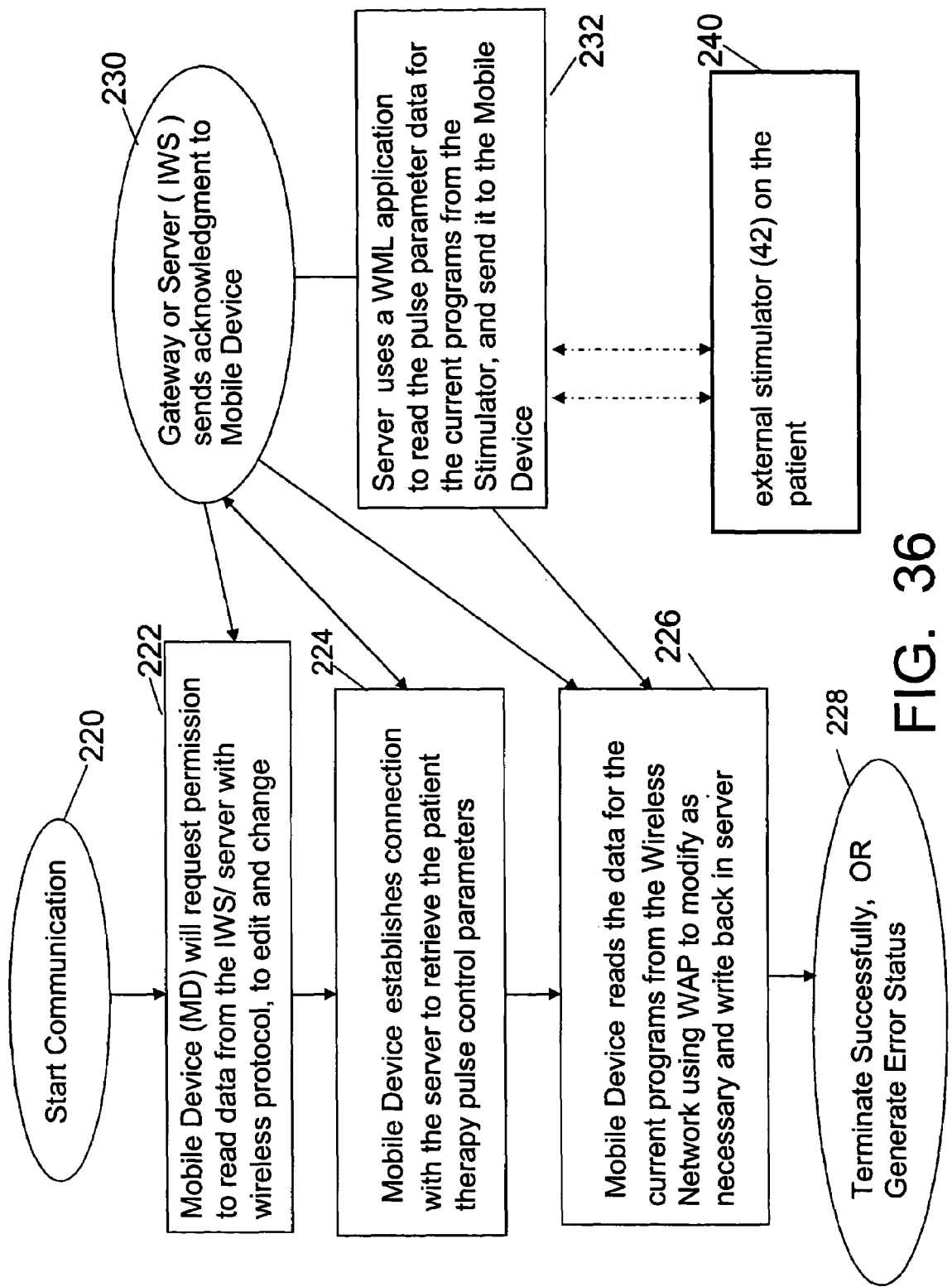
FIG. 36 is a flowchart showing the algorithm for wireless communication between the physician's mobile device and the long-term storage at a server.
Figure 37:
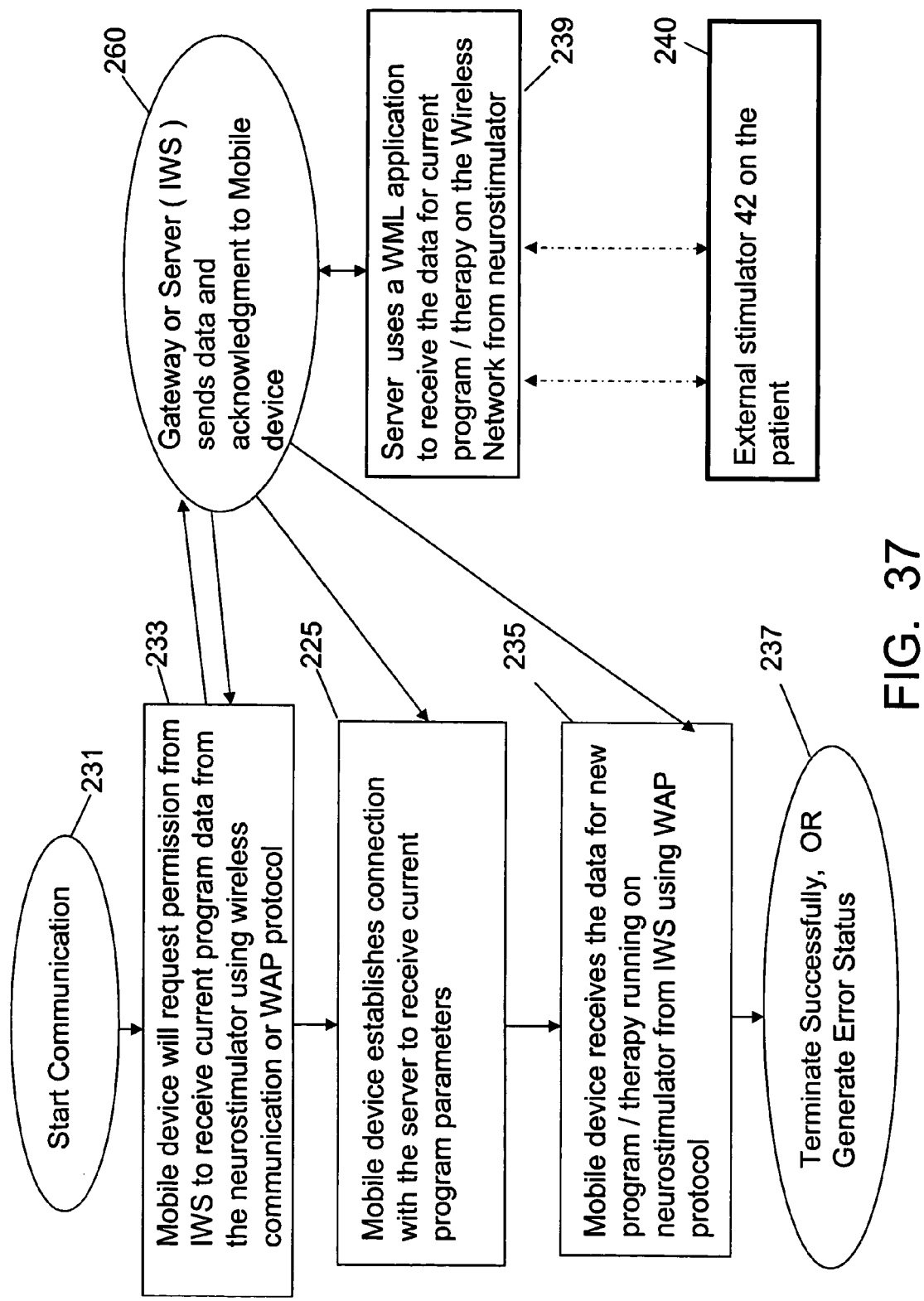
FIG. 37 is a flowchart showing the algorithm of wireless communication between the physician's handheld device and the interface device (external stimulator).

The algorithms for this remote wireless communication are shown in FIGS. 36 and 37. In FIG. 36 the mobile device device (modified PDA/cell phone 140) initiates communication with the server (IWS) 130 using the steps in method 222. The server (IWS) 130 sends acknowledgment 230 back to the mobile device indicating a successful communication link. The program-selection data can be pre-loaded in the mobile device or loaded on request from the database on the IWS 130, and the IWS 130 and mobile device communicate for this purpose. The IWS 130 sends acknowledgment on successful communication of data stream to the mobile device 140. The purpose of this algorithm is to provide a scheme for communication between the mobile device and the server (IWS) 130. This scheme provides for the program parameters, resident at the IWS 130, to be uploaded to the mobile device 140. The parameter and patient history information changes get made at the mobile device and these changes are downloaded back to the IWS 130. The IWS 130 performs some error checking at this point to verify that the selection and changes are feasible. A patient database is maintained at the IWS 130 and it is updated as patients are inserted there 226. The IWS 130 then sends the program parameters to the IU/stim 42 based on a different algorithm. A successful termination of a communication session between the mobile device 140 and IWS 130 is made after all relevant data is communicated 228.

FIG. 37 shows the ability of the wireless network to retrieve parameters from the IU/stim 42, which is physically on the patient. This algorithm supports the communication between the IU/stim 42 and the IWS 130. The IWS 130 can read from the IU/stim 42 This includes a request for data, sent to the IWS 130 from mobile device 140 (step 233), and then a request is sent to the IU/stim 42 from IWS 130, followed by IU/stim 42 sending the parameters for the current program back to the IWS 130. The parameters utilized for the current therapy cycle, can be queried by the server (IWS) 130 with wireless communication provided by WAP based algorithms. These parameters can then be communicated to the mobile device device 140, shown as steps 225, 235. The mobile device 140 can select a new program, which comes with its own set of parameters. This step is not shown in the algorithm, but is implied as an intuitive extension. These changes are communicated to the IWS 130 with method 235 and then the data provided back to the mobile device 140.

The algorithms on the IWS 130 checks for the validity of the modified parameters prior to downloading them to the IU/stim 42 attached on the patient (step 240) for a new version of the program. Since it is important to verify the validity of the parameters used for pulse generation, it is done at two levels. The first and most important level of checking is done at the IWS 130. Any change being made to the parameters by the mobile device user, has to be verified prior to being committed in the patient database. The second level of error checking is done when the parameters at the IU/stim 42 are queried by the IWS 130 and these parameters should match the values in the IWS 130 database for the particular patient.

While the invention herein disclosed has been described by means of specific embodiments and applications thereof, numerous modifications and variation could be made thereto by those skilled in the art without departing from the scope of the invention set forth in the claims.

What is claimed is:

1. A method to remotely control the electrical pulses supplied to a nerve tissue by an implantable neurostimulator, using a mobile device capable of communicating and exchanging data over a wide area network, comprising the steps of:

providing an implantable neurostimulator comprising circuitry, at least one lead adapted to be in contact with nerve tissue, and coil for communication; wherein said implantable neurostimulator comprises an implantable pulse generator module and a stimulus-receiver module that receives external stimulus signals and is capable of applying said electrical pulses independently of said pulse generator module;

providing an external interface means for networking over a wide area network to exchange data, and in communication with said implantable neurostimulator;

providing software applications means to said mobile device to communicate and exchange said data;

establishing a communication connection between said mobile device and said implantable neurostimulator via said external interface; wherein
   said communication may be initiated by a physician or a patient;

interrogating said implantable neurostimulator;

transmitting new programming information or data related to neurostimulation programs; and updating said transmitted information on said mobile device or on a remote computer using said mobile device, whereby said remote mobile device controls said implantable neurostimulator.

2. The method of claim 1, wherein said external interface further comprises an external stimulator inductively coupled to the said implanted stimulator.

3. The method of claim 1, wherein further said remote mobile device is at least one of a modified PDA/cell phone, a desk lop computer, a lap-top computer, a pocket PC/cell phone, a hand-held device.

4. The method of claim 1, wherein said data exchange is exchange of data relevant to nerve stimulation patients comprising, patient history, nerve stimulation parameters, stimulation schedules, patient reports, patient contact information, and patient insurance information.

5. The method of claim 1, wherein controlling remotely said electric pulses, comprises at least one of monitoring, interrogating, programming, or scheduling said pulses.

6. The method of claim 1, wherein said data exchange and remotely control of electrical pulses supplied to a nerve tissue are for providing therapy for at least one of neurological, neuropsychiatric, urological, cardiac disorders, or intractable pain treated by spinal cord stimulation.

7. The method of claim 1, wherein said remote mobile device further comprises software to store, edit, add, download, or upload said data.

8. A method of communicating and exchanging nerve stimulation patient related data, remotely over a wide area network for at least one of monitoring, or programming an implantable neurostimulator comprising the steps of:

providing an external interface means for networking over said wide area network;

providing said remote mobile device with means for networking over said wide area network; and providing software application means for exchanging said nerve stimulation patient related data;

establishing a communication connection between said mobile device and said implantable neurostimulator via said external interface; wherein said communication may be initiated by a physician or a patient;

interrogating said implantable neurostimulator, wherein said implantable neurostimulator comprises an implantable pulse generator module and a stimulus-receiver module that receives external stimulus signals and is capable of applying said electrical pulses independently of said pulse generator module;

transmitting new patient information or data related to neurostimulation programs;

updating said transmitted information on said mobile device or on a remote computer using said mobile device; and updating billing and/or patient information on a remote computer using said mobile device.

9. The method of claim 8, wherein further said implantable nerve stimulation device is adapted to be in contact with a nerve tissue, and comprises an implanted stimulus-receiver module and an implanted pulse generator (IPG) module.

10. The method of claim 8, wherein said external interface is an external stimulator inductively coupled to the said implanted stimulator.

11. The method of claim 8, wherein further said remote mobile device is at least one of a modified PDA cell phone, a desk lop computer, a lap-top computer, or a pocket PC/cell phone.

12. The method of claim 8, wherein said data exchange is exchange of data for nerve stimulation patients, comprising patient history, nerve stimulation parameters, stimulation schedules, patient reports, patient contact information, and patient insurance information.

13. The method of claim 8, wherein said mobile device further comprises pre-stored diagnostic codes and current procedural terminology (CPT) codes for billing, automatic invoicing, or invoice templates.

14. The method of claim 8, wherein further said implanted nerve stimulator device is used for providing therapy for at least one of neurological, neuropsychiatric, urological, and cardiac disorders, or intractable pain treated by spinal cord stimulation.

15. A system for at least one of monitoring and programming an implanted neurostimulator device, with a remote device over a wide area network, comprising:

said implantable neurostimulator comprising circuitry, at least one lead adapted for providing electrical pulses to the nerve tissue, and a coil for communication, wherein said implantable neurostimulator comprises an implantable pulse generator module and a stimulus-receiver module that receives external stimulus signals and is capable of applying said electrical pulses independently of said pulse generator module;

an external interface means for networking over a wide area network and in communication with said implantable neurostimulator;

a remote mobile device adapted with means for networking over a wide area network;

software applications means for said mobile device, configured for communicating and exchanging data over said wide area network, and to remotely change parameters of said electric pulses provided by said neurostimulator;

a software configured and adapted for storing updated patient information in said remote mobile device; and a software configured and adapted for updating and storing billing information in a remote computer using said remote mobile device.

16. The system of claim 15, wherein further said neurostimulator is utilized for providing therapy for at least one of neurological, neuropsychiatric, urological, and cardiac disorders, or intractable pain treated by spinal cord stimulation.

17. The system of claim 15, wherein said external interface means is adapted to be inductively coupled to said implanted neurostimulator.

18. The system of claim 15, wherein said implantable nerve stimulation device further comprises an implanted stimulus-receiver module and an implanted pulse generation module (IPG).

19. The system of claim 15, wherein said external interface means further comprises an external stimulator.

20. The system of claim 15, wherein further said remote mobile device is at least one of a modified PONcell phone, a desk-top computer, a lap-top computer, an internet ready pocket PC, or an internet ready personal digital assistant.

21. The system of claim 15, wherein said data exchange is exchange of data relevant to nerve stimulation patients, comprising patient history, nerve stimulation parameters, stimulation schedules, patient reports, patient contact information, or patient insurance information.

22. The system of claim 15, wherein further said remote mobile device can store, edit, add, download, and upload said data.

23. The system of claim 15, wherein said mobile device further comprises pre-stored diagnostic codes and current procedural terminology (OPT) codes for billing, automatic invoicing, or invoice templates.

24. A system of remotely accessing patient data on a mobile device and utilizing said data to remotely control an implantable neurostimulator providing electrical pulses to a nerve tissue, comprising:

said implantable neurostimulator comprising circuitry, at least one lead adapted for providing electrical pulses to said nerve tissue, and a coil for communication; wherein said implantable neurostimulator comprises an implantable pulse generator module and a stimulus-receiver module that receives external stimulus signals and is capable of applying said electrical pulses independently of said pulse generator module;

an external interface means for networking over a wide area network, and in communication with said implantable neurostimulator;

a remote mobile device with means for networking over a wide area network;

software applications means for said mobile device configured for:
  i) communicating and exchanging data over said wide area network, ii) for remotely changing parameters of said electric pulses provided by said neurostimulator, and iii) for storing, editing, adding, downloading, and uploading said data; and means for interrogating and remotely altering neurostimulation therapy programs over said wide area network.

25. The system of claim 24, wherein further said neurostimulator is utilized for providing therapy for at least one of neurological, neuropsychiatric, urological, and cardiac disorders, or intractable pain treated by spinal cord stimulation.

26. The system of claim 24, wherein said external interface means is adapted to be inductively coupled to said implanted neurostimulator.

27. The system of claim 24, wherein said implantable nerve stimulation device further comprises an implanted stimulus receiver module and an implanted pulse generation module (IPG).

28. The system of claim 24, wherein said external interface means further comprises an external stimulator.

29. The system of claim 24, wherein further said remote mobile device is at least one of a modified PDA/cell phone, a desk-top computer, a lap-top computer, an internet ready pocket PC, or an internet ready personal digital assistant.

30. The system of claim 24, wherein said data exchange is exchange of data for nerve stimulation patients, comprising patient history, nerve stimulation parameters, stimulation schedules, patient reports, patient contact information, and patient insurance information.

31. The system of claim 24, wherein said mobile device further comprises pre-stored diagnostic codes and current procedural terminology (CPT) codes for billing, automatic invoicing, or invoicing templates.

* * * * *